US008263368B2

(12) United States Patent
Svendsen et al.

(10) Patent No.: US 8,263,368 B2
(45) Date of Patent: *Sep. 11, 2012

(54) ALPHA-AMYLASE MUTANTS

(75) Inventors: Allan Svendsen, Birkerod (DK); Torben Vedel Borchert, Copenhagen (DK); Henrik Bisgard-Frantzen, Bagsvaerd (DK); Helle Outtrup, Ballerup (DK); Bjarne Ronfeldt Nielsen, Virum (DK); Vibeke Skovgaard Nielsen, Bagsvaerd (DK); Lisbeth Hedegaard, Skodsborg (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/493,860

(22) Filed: Jun. 29, 2009

(65) Prior Publication Data
US 2009/0317864 A1 Dec. 24, 2009

Related U.S. Application Data

(62) Division of application No. 10/327,837, filed on Dec. 23, 2002, now Pat. No. 7,566,561, which is a division of application No. 09/545,586, filed on Apr. 7, 2000, now Pat. No. 6,528,298, which is a division of application No. 09/290,734, filed on Apr. 13, 1999, now Pat. No. 6,361,989, which is a division of application No. 09/170,670, filed on Oct. 13, 1998, now Pat. No. 6,187,576.

(60) Provisional application No. 60/063,306, filed on Oct. 28, 1997.

(30) Foreign Application Priority Data

Oct. 13, 1997 (DK) .................................. 1172/97
Mar. 31, 1999 (DK) ............................. 1999 00439

(51) Int. Cl.
*C12N 9/28* (2006.01)
*C12S 11/00* (2006.01)
*C12P 19/14* (2006.01)

(52) U.S. Cl. ........... 435/99; 435/202; 435/201; 435/263

(58) Field of Classification Search ........................ None
See application file for complete search history.

(56) References Cited

U.S. PATENT DOCUMENTS

| 6,143,708 | A | 11/2000 | Svendsen |
| 6,204,232 | B1 | 3/2001 | Borchert et al. |
| 6,361,989 | B1 | 3/2002 | Svendsen et al. |
| 6,436,888 | B1 | 8/2002 | Svendsen |

FOREIGN PATENT DOCUMENTS

| WO | WO 90/11352 A1 | 10/1990 |
| WO | WO 91/00353 A2 | 1/1991 |
| WO | WO 95/10603 A1 | 4/1995 |
| WO | WO 95/26397 A1 | 10/1995 |
| WO | WO 95/35382 A2 | 12/1995 |
| WO | WO 96/23873 A1 | 8/1996 |
| WO | WO 96/23874 A1 | 8/1996 |
| WO | WO 97/41213 A1 | 11/1997 |

OTHER PUBLICATIONS

Bisgaard-Frantzen et al., Database GenBank, Accession No. W12956 (1996).
Tsukamoto et al., Biochemical and Biophysical Research Communications, vol. 151, No. 1, pp. 25-31 (1988).
Tsukamoto et al. (Gen Bank Accession No. P19571) 1991.
Marcel T (Gen Bank Accession No. S15713) 1991.
H. Guo et al., "Protein Tolerance to Random Amino Add Change", PNAS 101(25): 9205-9210. (Jun. 2004).
Gray et al., "Structural Genes Encoding the Thermophilic Alpha-Amylases of *Bacillus stearothermophilus* and *B. liceniformis*", Journal of Bacteriology, vol. 166, No. 2, pp. 635-643 (1986).
Lin et al., GenBank Database, Accession No. Q59222 (1996).
Nakajima et al., GenBank Database, Accession No. P06279 (1985).
Tsukamoto et al., GenBank Database, Accession No. M18862 (1988).

*Primary Examiner* — Rebecca Prouty
(74) *Attorney, Agent, or Firm* — Elias Lambiris

(57) ABSTRACT

The invention relates to a novel Termamyl-like alpha-amylase, and Termamyl-like alpha-amylases comprising mutations in two, three, four, five or six regions/positions. The variants have increased thermostability at acidic pH and/or at low $Ca^{2+}$ concentrations (relative to the parent). The invention also relates to a DNA construct comprising a DNA sequence encoding an alpha-amylase variant of the invention, a recombinant expression vector which carries a DNA construct of the invention, a cell which is transformed with a DNA construct of the invention, the use of an alpha-amylase variant of the invention for washing and/or dishwashing, textile desizing, starch liquefaction, a detergent additive comprising an alpha-amylase variant of the invention, a manual or automatic dishwashing detergent composition comprising an alpha-amylase variant of the invention, a method for generating a variant of a parent Termamyl-like alpha-amylase, which variant exhibits increased thermostability at acidic pH and/or at low $Ca^{2+}$ concentrations (relative to the parent).

18 Claims, 9 Drawing Sheets

```
         1                                                            50
1   HHNGTNGTMM  QYFEWHLPND  GNHWNRLRDD  ASNLRNRGIT  AIWIPPAWKG
2   HHNGTNGTMM  QYFEWHLPND  GNHWNRLRDD  AANLKSKGIT  AVWIPPAWKG
3   HHNGTNGTMM  QYFEWYLPND  GNHWNRLRDD  AANLKSKGIT  AVWIPPAWKG
4   ....VNGTLM  QYFEWYTPND  GQHWKRLQND  AEHLSDIGIT  AVWIPPAYKG
5   ..ANLNGTLM  QYFEWYMPND  GQHWRRLQND  SAYLAEHGIT  AVWIPPAYKG
6   .AAPFNGTMM  QYFEWYLPDD  GTLWTKVANE  ANNLSSLGIT  ALWLPPAYKG
7   ..NGTNGTMM  QYFEWYLPND  GNHWNRLRSD  ASNLKDKGIS  AVWIPPAWKG
8   HHNGTNGTMM  QYFEWYLPND  GNHWNRLRSD  ASNLKDKGIS  AVWIPPAWKG
9   HHNGTNGTMM  QYFEWYLPND  GNHWNRLRSD  ASNLKDKGIS  AVWIPPAWKG 51                                                           100
1   TSQNDVGYGA  YDLYDLGEFN  QKGTVRTKYG  TRSQLESAIH  ALKNNGVQVY
2   TSQNDVGYGA  YDLYDLGEFN  QKGTVRTKYG  TRSQLQGAVT  SLKNNGIQVY
3   TSQNDVGYGA  YDLYDLGEFN  QKGTVRTKYG  TRNQLQAAVT  SLKNNGIQVY
4   LSQSDNGYGP  YDLYDLGEFQ  QKGTVRTKYG  TKSELQDAIG  SLHSRNVQVY
5   TSQADVGYGA  YDLYDLGEFH  QKGTVRTKYG  TKGELQSAIK  SLHSRDINVY
6   TSRSDVGYGV  YDLYDLGEFN  QKGTVRTKYG  TKAQYLQAIQ  AAHAAGMQVY
7   ASQNDVGYGA  YDLYDLGEFN  QKGTIRTKYG  TRNQLQAAVN  ALKSNGIQVY
8   ASQNDVGYGA  YDLYDLGEFN  QKGTIRTKYG  TRNQLQAAVN  ALKSNGIQVY
9   ASQNDVGYGA  YDLYDLGEFN  QKGTIRTKYG  TRNQLQAAVN  ALKSNGIQVY 101                                                          150
1   GDVVMNHKGG  ADATENVLAV  EVNPNNRNQE  ISGDYTIEAW  TKFDFPGRGN
2   GDVVMNHKGG  ADGTEMVNAV  EVNRSNRNQE  ISGEYTIEAW  TKFDFPGRGN
3   GDVVMNHKGG  ADGTEIVNAV  EVNRSNRNQE  TSGEYAIEAW  TKFDFPGRGN
4   GDVVLNHKAG  ADATEDVTAV  EVNPANRNQE  TSEEYQIKAW  TDFRFPGRGN
5   GDVVINHKGG  ADATEDVTAV  EVDPADRNRV  ISGEHLIKAW  THFHFPGRGS
6   ADVVFDHKGG  ADGTEWVDAV  EVNPSDRNQE  ISGTYQIQAW  TKFDFPGRGN
7   GDVVMNHKGG  ADATEMVRAV  EVNPNNRNQE  VSGEYTIEAW  TKFDFPGRGN
8   GDVVMNHKGG  ADATEMVRAV  EVNPNNRNQE  VSGEYTIEAW  TKFDFPGRGN
9   GDVVMNHKGG  ADATEMVRAV  EVNPNNRNQE  VSGEYTIEAW  TKFDFPGRGN 151                                                          200
1   TYSDFKWRWY  HFDGVDWDQS  RQFQNRIYKF  RGDGKAWDWE  VDSENGNYDY
2   THSNFKWRWY  HFDGTDWDQS  RQLQNKIYKF  RGTGKAWDWE  VDIENGNYDY
3   NHSSFKWRWY  HFDGTDWDQS  RQLQNKIYKF  RGTGKAWDWE  VDTENGNYDY
4   TYSDFKWHWY  HFDGADWDES  RKI.SRIFKF  RGEGKAWDWE  VSSENGNYDY
5   TYSDFKWHWY  HFDGTDWDES  RKL.NRIYKF  ..QGKAWDWE  VSNENGNYDY
6   TYSSFKWRWY  HFDGVDWDES  RKL.SRIYKF  RGIGKAWDWE  VDTENGNYDY
7   THSNFKWRWY  HFDGVDWDQS  RKLNNRIYKF  RGDGKGWDWE  VDTENGNYDY
8   THSNFKWRWY  HFDGVDWDQS  RKLNNRIYKF  RGDGKGWDWE  VDTENGNYDY
9   THSNFKWRWY  HFDGVDWDQS  RKLNNRIYKF  RGDGKGWDWE  VDTENGNYDY
```

Fig. 1

```
      201                                                            250
1   LMYADVDMDH  PEVVNELRRW  GEWYTNTLNL  DGFRIDAVKH  IKYSFTRDWL
2   LMYADIDMDH  PEVINELRNW  GVWYTNTLNL  DGFRIDAVKH  IKYSYTRDWL
3   LMYADVDMDH  PEVIHELRNW  GVWYTNTLNL  DGFRIDAVKH  IKYSFTRDWL
4   LMYADVDYDH  PDVVAETKKW  GIWYANELSL  DGFRIDAAKH  IKFSFLRDWV
5   LMYADIDYDH  PDVAAEIKRW  GTWYANELQL  DGFRLDAVKH  IKFSFLRDWV
6   LMYADLDMDH  PEVVTELKNW  GKWYVNTTNI  DGFRLDAVKH  IKFSFPPDWL
7   LMYADIDMDH  PEVVNELRNW  GVWYTNTLGL  DGFRIDAVKH  IKYSFTRDWS
8   LMYADIDMDH  PEVVNELRNW  GVWYTNTLGL  DGFRIDAVKH  IKYSFTRDWI
9   LMYADIDMDH  PEVVNELRNW  GVWYTNTLGL  DGFRIDAVKH  IKYSFTRDWI 251                                                            300
1   THVRNATGKE  MFAVAEFWKN  DLGALENYLN  KTNWNHSVFD  VPLHYNLYNA
2   THVRNTTGKP  MFAVAEFWKN  DLAAIENYLN  KTSWNHSVFD  VPLHYNLYNA
3   THVRNTTGKP  MFAVAEFWKN  DLGAIENYLN  KTSWNHSAFD  VPLHYNLYNA
4   QAVRQATGKE  MFTVAEYWQN  NAGKLENYLN  KTSFNQSVFD  VPLHFNLQAA
5   NHVREKTGKE  MFTVAEYWQN  DLGALENYLN  KTNFNHSVFD  VPLHYQFHAA
6   SYVRSQTGKP  LFTVGEYWSY  DINKLHNYIT  KTDGTMSLFD  APLHNKFYTA
7   IHVRSATGKN  MFAVAEFWKN  DLGAIENYLN  KTNWNHSVFD  VPLHYNFYNA
8   NHVRSATGKN  MFAVAEFWKN  DLGAIENYLN  KTNWNHSVFD  VPLHYNLYNA
9   NHVRSATGKN  MFAVAEFWKN  DLGAIENYLN  KTNWNHSVFD  VPLHYNLYNA 301                                                            350
1   SNSGGNYDMA  KLLNGTVVQK  HPMHAVTFVD  NHDSQPGESL  ESFVQEWFKP
2   SNSGGYFDMR  NILNGSVVQK  HPIHAVTFVD  NHDSQPGEAL  ESFVQSWFKP
3   SNSGGYYDMR  NILNGSVVQK  HPTHAVTFVD  NHDSQPGEAL  ESFVQQWFKP
4   SSQGGGYDMR  RLLDGTVVSR  HPEKAVTFVE  NHDTQPGQSL  ESTVQTWFKP
5   STQGGGYDMR  KLLNGTVVSK  HPLKSVTFVD  NHDTQPGQSL  ESTVQTWFKP
6   SKSGGAFDMR  TLMTNTLMKD  QPTLAVTFVD  NHDTEPGQAL  QSWVDPWFKP
7   SKSGGNYDMR  QIFNGTVVQR  HPMHAVTFVD  NHDSQPEEAL  ESFVEEWFKP
8   SKSGGNYDMR  QIFNGTVVQR  HPMHAVTFVD  NHDSQPEEAL  ESFVEEWFKP
9   SKSGGNYDMR  QIFNGTVVQR  HPMHAVTFVD  NHDSQPEEAL  ESFVEEWFKP 351                                                            400
1   LAYALILTRE  QGYPSVFYGD  YYGIPTHS..  .VPAMKAKID  PILEARQNFA
2   LAYALILTRE  QGYPSVFYGD  YYGIPTHG..  .VPSMKSKID  PLLQARQTYA
3   LAYALVLTRE  QGYPSVFYGD  YYGIPTHG..  .VPAMKSKID  PLLQARQTFA
4   LAYAFILTRE  SGYPQVFYGD  MYGTKGTSPK  EIPSLKDNIE  PILKARKEYA
5   LAYAFILTRE  SGYPQVFYGD  MYGTKGDSQR  EIPALKHKIE  PILKARKQYA
6   LAYAFILTRQ  EGYPCVFYGD  YYGIPQYN..  .IPSLKSKID  PLLIARRDYA
7   LAYALTLTRE  QGYPSVFYGD  YYGIPTHG..  .VPAMKSKID  PILEARQKYA
8   LAYALTLTRE  QGYPSVFYGD  YYGIPTHG..  .VPAMKSKID  PILEARQKYA
9   LAYALTLTRE  QGYPSVFYGD  YYGIPTHG..  .VPAMKSKID  PILEARQKYA
```

Fig. 1A

```
      401                                                              450
1  YGTQHDYFDH  HNIIGWTREG  NTTHPNSGLA  TIMSDGPGGE  KWMYVGQNKA
2  YGTQHDYFDH  HDIIGWTREG  DSSHPNSGLA  TIMSDGPGGN  KWMYVGKHKA
3  YGTQHDYFDH  HDIIGWTREG  NSSHPNSGLA  TIMSDGPGGN  KWMYVGKNKA
4  YGPQHDYIDH  PDVIGWTREG  DSSAAKSGLA  ALITDGPGGS  KRMYAGLKNA
5  YGAQHDYFDH  HDIVGWTREG  DSSVANSGLA  ALITDGPGGA  KRMYVGRQNA
6  YGTQHDYLDH  SDIIGWTREG  GTEKPGSGLA  ALITDGPGGS  KWMYVGKQHA
7  YGRQN.....  ..........  ..........  ..........  ..........
8  YGRQNDYLDH  HNIIGWTREG  NTAHPNSGLA  TIMSDGAGGN  KWMFVGRNKA
9  YGRQNDYLDH  HNIIGWTREG  NTAHPNSGLA  TIMSDGAGGN  KWMFVGRNKA 451                                                              500
1  GQVWHDITGN  KPGTVTINAD  GWANFSVNGG  SVSIWVKR..  ..........
2  GQVWRDITGN  RSGTVTINAD  GWGNFTVNGG  AVSVWVKQ..  ..........
3  GQVWRDITGN  RTGTVTINAD  GWGNFSVNGG  SVSVWVKQ..  ..........
4  GETWYDITGN  RSDTVKIGSD  GWGEFHVNDG  SVSIYVQ...  ..........
5  GETWHDITGN  RSEPVVINSE  GWGEFHVNGG  SVSIYVQR..  ..........
6  GKVFYDLTGN  RSDTVTINSD  GWGEFKVNGG  SVSVWVPRKT  TVSTIARPIT
7  ..........  ..........  ..........  ..........  ..........
8  GQVWTDITGN  RAGTVTINAD  GWGNFSVNGG  SVSIWVNK..  ..........
9  GQVWTDITGN  RAGTVTINAD  GWGNFSVNGG  SVSIWVNK..  ..........

501              519
1  ..........  ..........
2  ..........  ..........
3  ..........  ..........
4  ..........  ..........
5  ..........  ..........
6  TRPWTGEFVR  WTEPRLVAW
7  ..........  ..........
8  ..........  ..........
9  ..........  ..........
```

ALPHA-AMYLASE MUTANTS

CROSS-REFERENCE TO RELATED APPLICATIONS

This application is a divisional of application Ser. No. 10/327,837, filed Dec. 23, 2002 (now U.S. Pat. No. 7,566,561), which is a divisional of application Ser. No. 09/545,586, filed on Apr. 7, 2000 (now U.S. Pat. No. 6,528,298), which is a divisional of application Ser. No. 09/290,734 filed on Apr. 13, 1999 (now U.S. Pat. No. 6,361,989), which is a continuation-in-part of application Ser. No. 09/170,670 filed on Oct. 13, 1998 (now U.S. Pat. No. 6,187,576), and claims priority under 35 U.S.C. 119 of Danish application no. 1172/97, filed on Oct. 13, 1997, and Danish application no. PA 1999 00439, filed on Mar. 31, 1999, and U.S. application No. 60/063,306, filed on Oct. 28, 1997, and, the contents of which are fully incorporated herein by reference.

FIELD OF THE INVENTION

The present invention relates a novel alpha-amylase within the family of Termamyl-like alpha-amylases suitable for detergents. The invention also relates to variants (mutants) of parent Termamyl-like alpha-amylases, notably variants exhibiting increased thermostability at acidic pH and/or at low $Ca^{2+}$ concentrations (relative to the parent) which are advantageous with respect to applications of the variants in, industrial starch processing particularly (e.g., starch liquefaction or saccharification). Said alpha-amylase and alpha-amylase variants of the invention may advantageously also be used in detergents.

BACKGROUND OF THE INVENTION

Alpha-Amylases (alpha-1,4-glucan-4-glucanohydrolases, EC 3.2.1.1) constitute a group of enzymes which catalyze hydrolysis of starch and other linear and branched 1,4-glucosidic oligo- and polysaccharides.

There is a very extensive body of patent and scientific literature relating to this industrially very important class of enzymes. A number of alpha-amylase such as Termamyl-like alpha-amylases variants are known from, e.g., WO 90/11352, WO 95/10603, WO 95/26397, WO 96/23873 and WO 96/23874.

Among more recent disclosures relating to alpha-amylases, WO 96/23874 provides three-dimensional, X-ray crystal structural data for a Termamyl-like alpha-amylase which consists of the 300 N-terminal amino acid residues of the *B. amyloliquefaciens* alpha-amylase and amino acids 301-483 of the C-terminal end of the *B. licheniformis* alpha-amylase comprising the amino acid sequence (the latter being available commercially under the tradename Termamyl™), and which is thus closely related to the industrially important *Bacillus* alpha-amylases (which in the present context are embraced within the meaning of the term "Termamyl-like alpha-amylases", and which include, inter alia, the *B. licheniformis, B. amyloliquefaciens* and *B. stearothermophilus* alpha-amylases). WO 96/23874 further describes methodology for designing, on the basis of an analysis of the structure of a parent Termamyl-like alpha-amylase, variants of the parent Termamyl-like alpha-amylase which exhibit altered properties relative to the parent.

WO 95/35382 (Gist Brocades B. V.) concerns amylolytic enzymes derived from *B. licheniformis* with improved properties allowing reduction of the $Ca^{2+}$ concentration under application without a loss of performance of the enzyme. The amylolytic enzyme comprises one or more amino acid changes at positions selected from the group of 104, 128, 187, 188 of the *B. licheniformis* alpha-amylase sequence.

WO 96/23873 (Novo Nordisk) discloses Termamyl-like alpha-amylase variants which have increased thermostability obtained by pairwise deletion in the region R181*, G182*, T183* and G184* of the sequence shown in SEQ ID NO: 1 herein.

WO 97/00324 (KAO) disclose a gene encoding an alkaline liquefying alpha-amylase derived from *Bacillus* sp. strain KSM-AP1378 with the deposited no. FERM BP-3048 suitable for detergents.

BRIEF DISCLOSURE OF THE INVENTION

The present invention relates to a novel alpha-amylase and to novel alpha-amylolytic variants (mutants) of a Termamyl-like alpha-amylase, in particular variants exhibiting increased thermostability (relative to the parent) which are advantageous in connection with the industrial processing of starch (starch liquefaction, saccharification and the like). The novel alpha-amylase is suitable for laundry washing and dishwash as is has a high activity under wash conditions at alkaline pHs in the range 9-11.

The inventors have surprisingly found out that in case of combining two, three, four, five or six mutations (will be described below), the thermostability of Termamyl-like alpha-amylases is increased at acidic pH and/or at low $Ca^{2+}$ concentration in comparison to single mutations, such as the mutation disclosed in WO 96/23873 (Novo Nordisk), i.e., pairwise deletion in the region R181*, G182*, T183* and G184* of the sequence shown in SEQ ID NO: 1 herein.

The invention further relates to DNA constructs encoding variants of the invention, to composition comprising variants of the invention, to methods for preparing variants of the invention, and to the use of variants and compositions of the invention, alone or in combination with other alpha-amylolytic enzymes, in various industrial processes, e.g., starch liquefaction.

BRIEF DESCRIPTION OF THE DRAWING

FIG. 1 is an alignment of the amino acid sequences of nine parent Termamyl-like alpha-amylases. The numbers on the Extreme left designate the respective amino acid sequences as follows:

1: SEQ ID NO: 2,
2: *Bacillus* sp. strain KSM-AP1378 disclosed in WO 97/00324
3: SEQ ID NO: 1,
4: SEQ ID NO: 5,
5: SEQ ID NO: 4,
6: SEQ ID NO: 3.
7: Partial alpha-amylase sequence
8: SEQ ID NO: 24
9: SEQ ID NO: 26.

Figure 2:
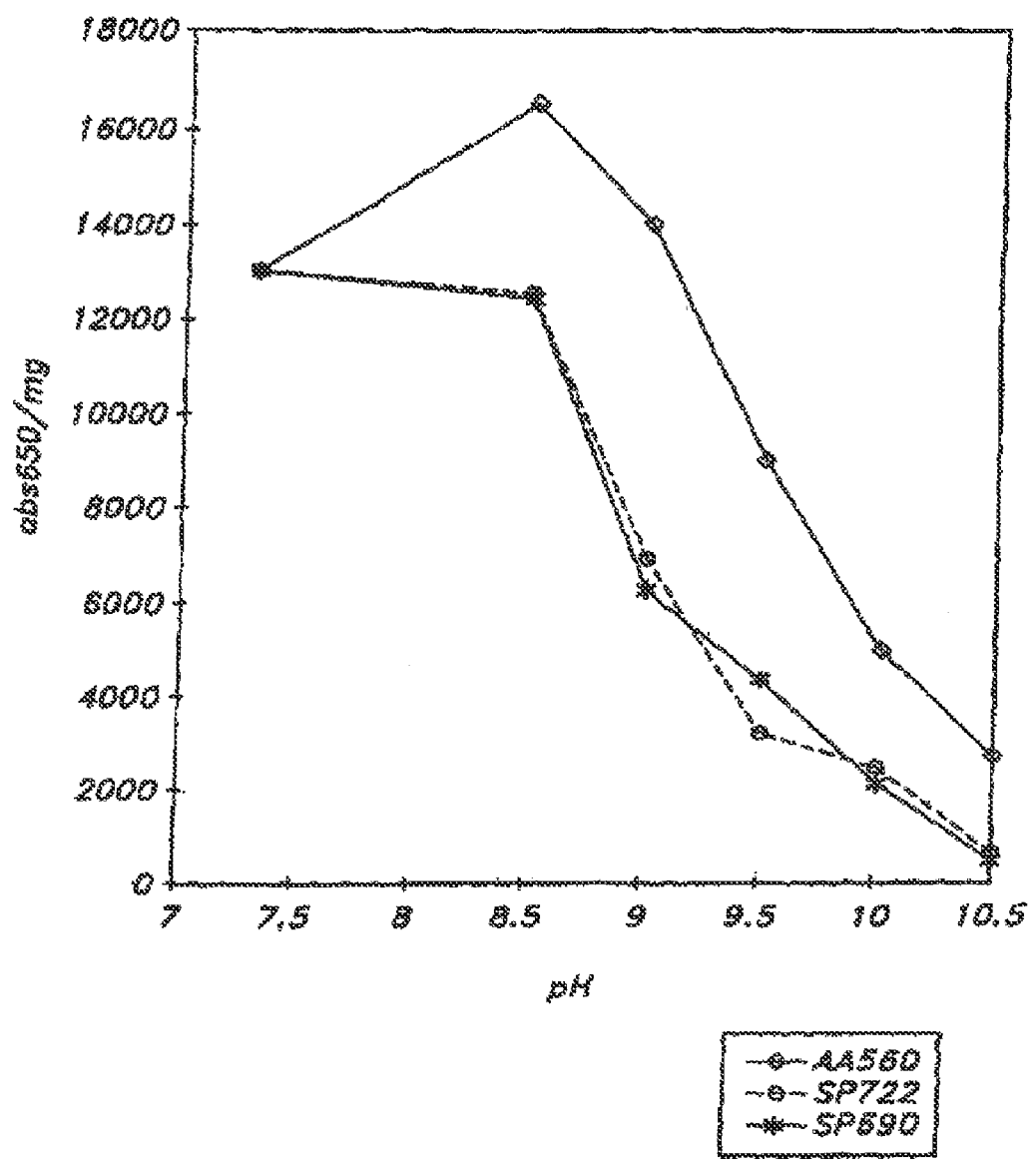

FIG. 2 shows the pH Profile of the AA560 a-amylase compared to the SP722 and SP690 alpha-amylases. The pH profile was measured at 37° C. The activity is shown in absolute values as Abs650/mg.

Figure 3:
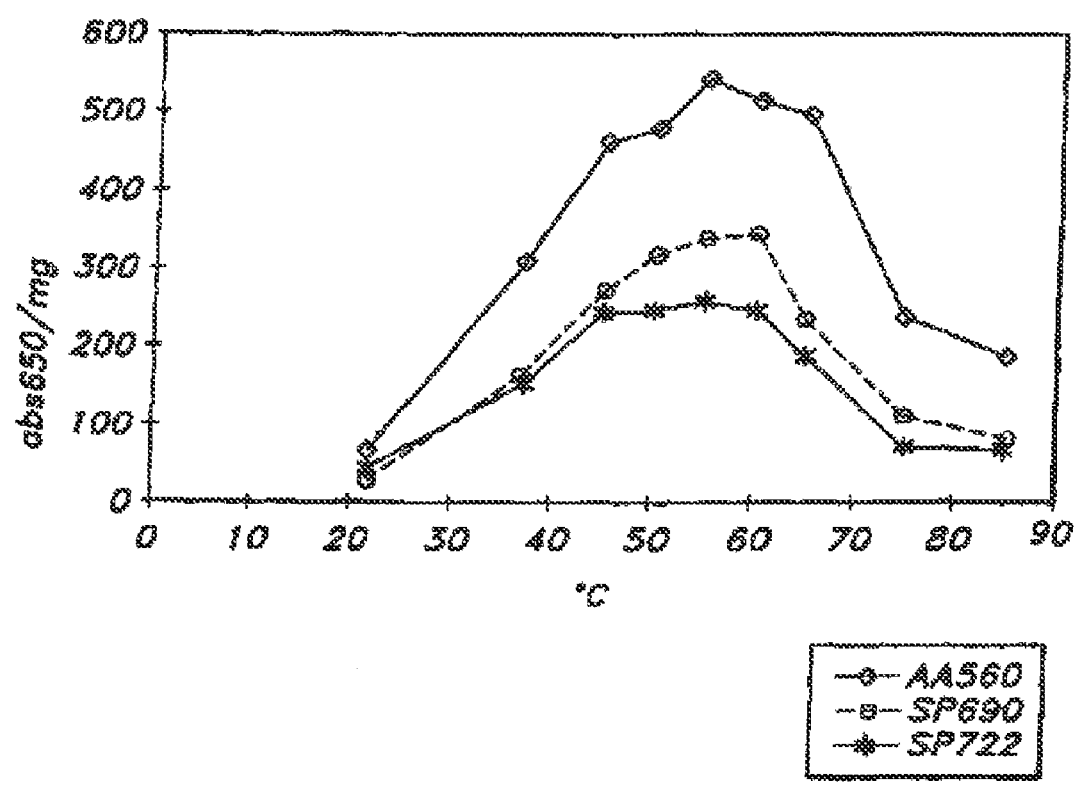

FIG. 3 shows the Temperature Profile of the AA560 alpha-amylase compared to the SP722 and SP690 alpha-amylases. The temperature profile shown as Abs650/mg.

Figure 4:
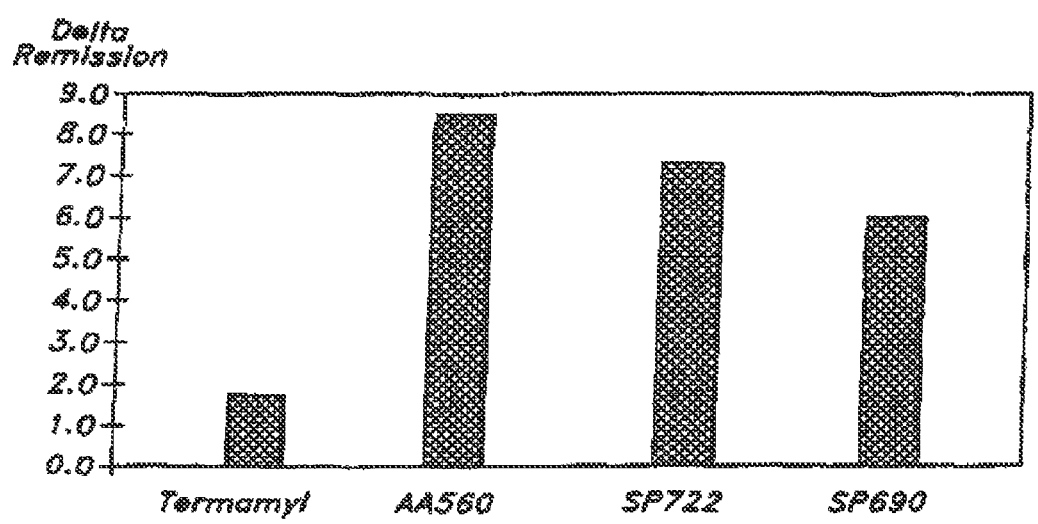

FIG. 4 shows the wash performance of AA560 in the AP Model Detergent 97 in comparison to SP722, SP690 and Termamyl®.

Figure 5:
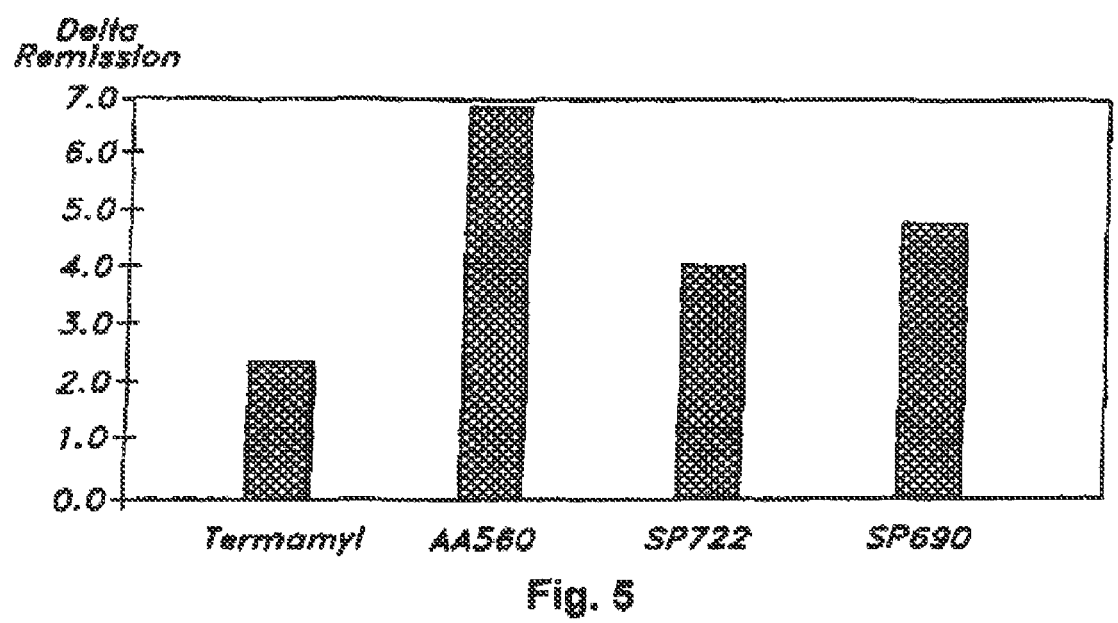

FIG. 5 shows the wash performance of AA560 in the Omo Multi Acao in comparison to SP722, SP690 and Termamyl®.

Figure 6:
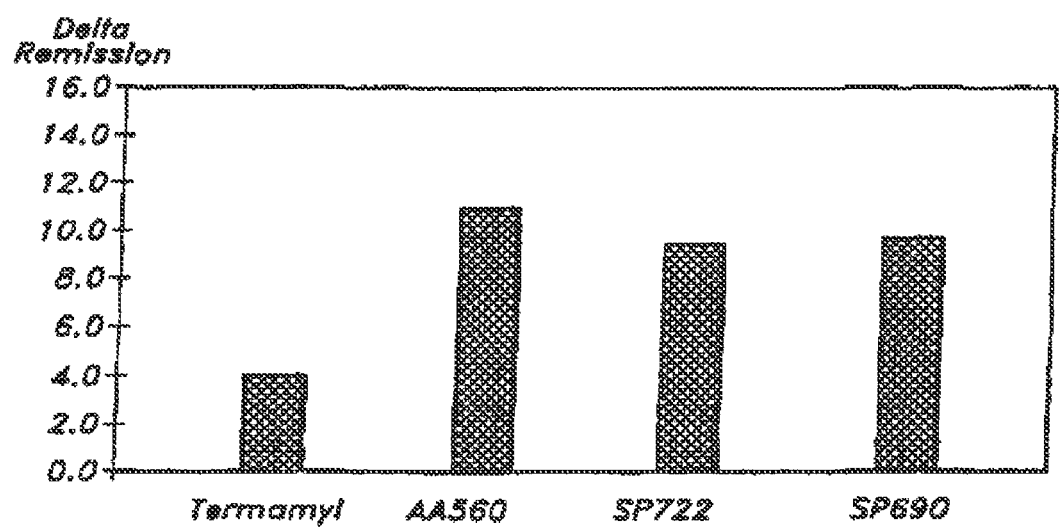

FIG. 6 shows the wash performance of AA560 in the Omo Concentrated in comparison to SP722, SP690 and Termamyl®.

Figure 7:
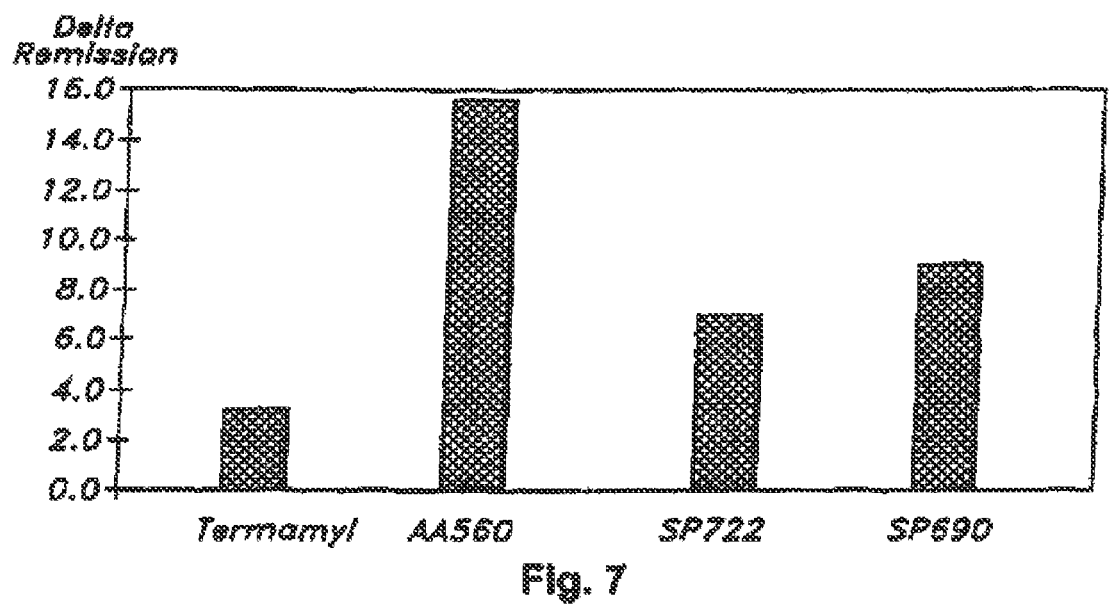

FIG. 7 shows the wash performance of AA560 in the Ariel Futur liquid in comparison to SP722, SP690 and Termamyl®.

DETAILED DISCLOSURE OF THE INVENTION

Alpha-Amylase Activity Determination

Alpha-Amylases (alpha-1,4-glucan-4-glucanohydrolases, EC 3.2.1.1) constitute a group of enzymes which catalyze hydrolysis of starch and other linear and branched 1,4-glucosidic oligo- and polysaccharides. For purposes of the present invention, alpha-amylase activity may be determined using the Phadebas assay, the pNPG7 assay and the BS-alpha-amylase activity assay described below in the "Materials and Methods" section.

The Novel Alpha-Amylase
Microbial Source

The novel alkaline alpha-amylase of the invention may be derived from a strain of *Bacillus*. Preferred strains are of *Bacillus* sp. DSM 12649 (the AA560 alpha-amylase) or *Bacillus* sp. DSM 12648 (the AA349 alpha-amylase). These strains were deposited on 25 Jan. 1999 by the inventors under the terms of the Budapest Treaty on the International Recognition of the Deposit of Microorganisms for the Purposes of Patent Procedure at Deutshe Sammmlung von Microorganismen und Zellkulturen GmbH (DSMZ), Mascheroder Weg 1b, D-38124 Braunschweig DE.

*Escherichia coli* strains termed NN049467 and NN049470 containing the alpha-amylase genes in plasmids pLiHl274 (AA349) and plasmid pTVB299 (AA560) have also been deposited on 7 Apr. 1999 under the terms of the Budapest Treaty with the Deutshe Sammmlung von Microorganismen und Zellkulturen GmbH (DSMZ), Mascheroder Weg 1b, D-38124 Braunschweig DE, and given the accession numbers DSM12761 and DSM12764, respectively.
Homology of Enzyme In a first embodiment, the present invention relates to isolated polypeptides having an amino acid sequence which has a degree of identity to amino acids 1 to 485 of SEQ ID NO: 24 or SEQ ID NO: 26 (i.e., the mature polypeptide) of at least about 96%, preferably at least about 97%, more preferably at least about 98%, even more preferably at least about 99%, which have alpha-amylase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 1 to 485 of SEQ ID NO: 24 or SEQ ID NO: 26. It is to be noted that SEQ ID NO: 24 and SEQ ID NO: 26 are identical. However, the DNA sequences, i.e., SEQ ID NO: 23 and SEQ ID NO: 25, respectively, encoding the alpha-amylase of the invention shown in SEQ ID NO: 24 and SEQ ID NO: 26 are not identical.

The amino acid sequence homology may be determined as the degree of identity between the two sequences indicating a derivation of the first sequence from the second. The homology may suitably be determined by means of computer programs known in the art. Thus, GAP provided in GCG version 8 (Needleman, S. B. and Wunsch, C. D., (1970), Journal of Molecular Biology, 48, 443-453) may be used for a pairwise alignment of the sequences and calculation of the degree of identity or degree of homology using the default settings. Alternatively, Gap from GCG version 9 may be used with a translated version 8 peptide scoring matrix, a gap creation penalty of 30, a gap extension penalty of 1 using ntol's matrix (http://plasmid/~bioweb/matrix/) without end gap penalty.
Homology (Identity) of the Novel Alpha-Amylase to Known *Bacillus* Sp. Alpha-Amylases A homology search of known sequences showed homologies for the sequences of the invention with a number of *Bacillus* amylases in the range 65-95% on amino acid basis determined as described above.

Specifically, the most homologous alpha-amylases found are SP690 (SEQ ID NO: 1 of U.S. Pat. No. 5,856,164 which is about 87% homologous), SP722 (SEQ ID NO: 2 of U.S. Pat. No. 5,856,164 which is about 87% homologous), the mature part (i.e., amino acids no. 31-516) of the alpha-amylase obtained from *Bacillus* sp. KSM-AP1378 disclosed as SEQ ID NO: 2 of WO 97/00324 which is about 86% homologous, and the alpha-amylase disclosed in Tsukamoto et. al., (1988), Biochem. Biophys. Res Commun. 151, p. 25-33) which is about 95% homologous to SEQ ID NO: 24 and SEQ ID NO: 26 determined as describe above.

Preferably, the polypeptides of the present invention comprise the amino acid sequence of SEQ ID NO: 24 or SEQ ID NO: 26 or allelic variants thereof; or fragments thereof that has alpha-amylase activity. SEQ ID NO: 24 and SEQ ID NO: 26 show the mature part of the alkaline alpha-amylase of the invention.

A fragment of SEQ ID NO: 24 or SEQ ID NO: 26 are polypeptides having one or more amino acids deleted from the amino and/or carboxyl terminus of this amino acid sequence.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the homologous polypeptides may differ from the amino acid sequence of SEQ ID NO: 24 or SEQ ID NO: 26 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a second embodiment, the present invention relates to isolated polypeptides having alpha-amylase activity which are encoded by nucleic acid sequences which hybridize under medium stringency conditions, preferably medium-high stringency conditions, more preferably high stringency conditions, and most preferably very high stringency conditions with a nucleic acid probe which hybridizes under the same conditions with (i) the nucleic acid sequence of SEQ ID NO: 23 or SEQ ID NO: 25, (ii) the cDNA sequence of SEQ ID NO: 23 or SEQ ID NO: 25, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). The subsequence of SEQ ID NO: 23 or SEQ ID NO: 25 may be at least 100 nucleotides or preferably at least 200 nucleotides. Moreover, the subsequence may encode a polypeptide fragment which has alpha-amylase activity. The polypeptides may also be allelic variants or fragments of the polypeptides that have alpha-amylase activity.

The nucleic acid sequence of SEQ ID NO: 23 or SEQ ID NO: 25 or a subsequence thereof, as well as the amino acid sequence of SEQ ID NO: 24 or SEQ ID NO: 26 or a fragment thereof, may be used to design a nucleic acid probe to identify and clone DNA encoding polypeptides having alpha-amylase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA which hybridizes with the probes described above and which encodes a polypeptide having alpha-amylase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 23 or SEQ ID NO: 25 or subsequences thereof, the carrier material is used in a Southern blot.

For purposes of the present invention, hybridization indicates that the nucleic acid sequence hybridizes to a nucleic acid probe corresponding to the nucleic acid sequence shown in SEQ ID NO: 23 or SEQ ID NO: 25, its complementary strand, or subsequences thereof, under medium to very high stringency conditions. Molecules to which the nucleic acid probe hybridizes under these conditions are detected using X-ray film.

In another preferred embodiment, the nucleic acid probe is the nucleic acid sequence contained in plasmids pLiH1274 (AA349) or pTVB299 (AA560) which are contained in *Escherichia coli* DSM12761 or *Escherichia coli* DSM12764, respectively, or, wherein the nucleic acid sequence encodes a polypeptide having acid alpha-amylase activity of the invention and shown in SEQ ID NO: 24 and SEQ ID NO: 26, respectively.

For long probes of at least 100 nucleotides in length, medium to very high stringency conditions are defined as prehybridization and hybridization at 42° C. in 5×SSPE, 0.3% SDS, 200 ig/ml sheared and denatured salmon sperm DNA, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 55° C. (medium stringency), preferably at least at 60° C. (medium-high stringency), more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third embodiment, the present invention relates to isolated polypeptides, i.e., the polypeptides shown in SEQ ID NO: 24 or SEQ ID NO: 26, having the following physico-chemical properties:

A pH optimum (see FIG. 2) determined using the Phadebas method (37° C.) was found to be in the range between pH 8 and 9, more precisely at about 8.5.

A temperature optimum (See FIG. 3) determined using the Phasebas method (pH 9.0) was found to be in the range between 55 and 65° C., more precisely about 60° C.

A pI between 7-8 (See Table 1 in Example 11) was determined by isoelectric focusing (Pharmacia, Ampholine, pH 3.5-9.3).

A specific activity (see Table 1 of Example 11) of 35,000 NU/ml was determined using the Phadebas method and 6,000 NU/ml using the pNPG7 method.

The alpha-amylase of the present invention have at least 20%, preferably at least 40%, more preferably at least 60%, even more preferably at least 80%, even more preferably at least 90%, and most preferably at least 100% of the alpha-amylase activity of the mature alpha-amylase shown in SEQ ID NO: 24 and SEQ ID NO: 26.

An alpha-amylase of the present invention may be obtained from microorganisms of any genus. For purposes of the present invention, the term "obtained from" as used herein in connection with a given source shall mean that the alpha-amylase encoded by the nucleic acid sequence is produced by the source or by a cell in which the nucleic acid sequence from the source has been inserted.

An alpha-amylase of the present invention is a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans,*

*Bacillus lautus, Bacillus lentus, Bacillus licheniformis, Bacillus megaterium, Bacillus stearothermophilus, Bacillus subtilis*, or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

In another preferred embodiment, the polypeptide is a *Bacillus* sp. polypeptide, more preferred embodiment, the polypeptide is a *Bacillus* sp. DSM 12648 or *Bacillus* sp. DSM 12649 polypeptide, e.g., the polypeptides with the amino acid sequence of SEQ ID NO: 24 and SEQ ID NO: 26, respectively.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-alpha-amylase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Mutants of the Novel Alpha-Amylase

Specifically contemplated mutants of the novel alpha-amylase shown in SEQ ID NO: 24 (or SEQ ID NO: 26) are described in the following. A mutant alpha-amylase of the invention is characterized by the fact that one or more of the methionine amino acid residues is exchanged with any amino acid residue except for Cys and Met. Thus, according to the invention the amino acid residues to replace the methionine amino acid residue are the following: Ala, Arg, Asn, Asp, Gln, Glu, Gly, His, Ile, Leu, Lys, Phe, Pro, Ser, Thr, Trp, Tyr, and Val.

A preferred embodiment of the mutant alpha-amylase of the invention is characterized by the fact that one or more of the methionine amino acid residues is (are) exchanged with a Leu, Thr, Ala, Gly, Ser, Ile, or Val amino acid residue, preferably a Leu, Thr, Ala, or Gly amino acid residue. In this embodiment a very satisfactory activity level and stability in the presence of oxidizing agents is obtained. Specifically this means that one or more of the methiones in the following position may be replaced or deleted using any suitable technique known in the art, including especially site directed mutagenesis and gene shuffling. Contemplated position, using the SEQ ID NO: 24 numbering, are: 9, 10, 105, 116, 202, 208, 261, 309, 323, 382, 430, 440.

In a preferred embodiment of the mutant alpha-amylase of the invention is characterized by the fact that the methionine amino acid residue at position 202 is exchanged with any of amino acid residue expect for Cys and Met, preferably with a Leu, Thr, Ala, Gly, Ser, Ile, or Asp.

Other contemplated preferred mutations include deletion of one, two or more residues of amino acids R181, G182, D183 or G184, K185, G186 or substitution of one or more of these residues. A preferred mutation is the deletion of D183-G184. Particularly relevant mutations are substitutions of G186 with Ala, Arg, Asn, Asp, Cys, Gln, Glu, His, Ile, Leu, Lys, Met, Phe, Pro, Ser, Thr, Trp, Tyr, and Val. A particularly preferred substitution is G186R.

Also contemplated is substitution of N195 with Ala, Arg, Asn, Asp, Cys, Gln, Glu, Gly, His, Ile, Leu, Lys, Met, Phe, Pro, Ser, Thr, Trp, Tyr, and Val. A particularly interesting substitution is N195F.

The following combinations of the above mentioned mutations include: deletion of D183-G184+N195F, deletion of D183-G184+G186R, deletion of D183-G184+G186R+N195F and G186R+N195F.

Nucleic Acid Sequences

The present invention also relates to isolated nucleic acid sequences which encode a polypeptide of the present invention. In a preferred embodiment, the nucleic acid sequence is set forth in SEQ ID NO: 23 or SEQ ID NO: 25. In another more preferred embodiment, the nucleic acid sequence is the sequence contained in plasmid pLiHl274 (AA349) or plasmid pTVB299 (AA560) that is contained in *Escherichia coli* DSM12761 and *Escherichia coli* DSM12764, respectively. In another preferred embodiment, the nucleic acid sequence is the mature polypeptide coding region of SEQ ID NO: 23 or SEQ ID NO: 25. The present invention also encompasses nucleic acid sequences which encode a polypeptide having the amino acid sequence of SEQ ID NO: 24 which differ from SEQ ID NO: 23 or SEQ ID NO: 25 by virtue of the degeneracy of the genetic code. The present invention also relates to subsequences of SEQ ID NO: 23 or SEQ ID NO: 25 which encode fragments of SEQ ID NO: 24 or SEQ ID NO: 26, respectively, that have alpha-amylase activity.

Subsequences of SEQ ID NO: 23 or SEQ ID NO: 25 are nucleic acid sequences encompassed by SEQ ID NO: 23 or SEQ ID NO: 25 except that one or more nucleotides from the 5' and/or 3' end have been deleted.

The present invention also relates to mutant nucleic acid sequences comprising at least one mutation in the mature polypeptide coding sequence of SEQ ID NO:1 or SEQ ID NO: 3, in which the mutant nucleic acid sequence encodes a polypeptide which consists of amino acids 1 to 485 of SEQ ID NO: 24 or SEQ ID NO: 26.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of *Bacillus*, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

Homology of DNA Sequence Encoding the Enzyme

The present invention also relates to nucleic acid sequences which have a degree of homology to the mature polypeptide coding sequence of SEQ ID NO: 23 (i.e., nucleotides 1 to 1458) or SEQ ID NO: 25 (i.e., nucleotide 1 to 1458) of at least about 96% homology on DNA level, preferably about 97%, preferably about 98%, more preferably about 99% homology, which encode an active polypeptide.

The DNA sequence homology may be determined as the degree of identity between the two sequences indicating a derivation of the first sequence from the second. The homology may suitably be determined by means of computer programs known in the art such as GAP provided in the GCG program package (described above). Thus, Gap GCGv8 may be used with the following default parameters: GAP creation penalty of 5.0 and GAP extension penalty of 0.3, default scoring matrix. GAP uses the method of Needleman/Wunsch/Sellers to make alignments.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO: 23 or SEQ ID NO: 25, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for [enzyme] activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to isolated nucleic acid sequences encoding a polypeptide of the present invention, which hybridize under medium stringency conditions, preferably medium-high stringency conditions, more preferably high stringency conditions, and most preferably very high stringency conditions with a nucleic acid probe which hybridizes under the same conditions with the nucleic acid sequence of SEQ ID NO:1 or SEQ ID NO: 3 or its complementary strand; or allelic variants and subsequences thereof (Sambrook et al., 1989, supra), as defined herein.

The present invention also relates to isolated nucleic acid sequences produced by (a) hybridizing a DNA under medium, medium-high, high, or very high stringency conditions with the sequence of SEQ ID NO: 23 or SEQ ID NO: 25, or their complementary strands, or a subsequence thereof; and (b) isolating the nucleic acid sequence. The subsequence is preferably a sequence of at least 100 nucleotides such as a sequence which encodes a polypeptide fragment which has alpha-amylase activity.

Methods for Producing Mutant Nucleic Acid Sequences

The present invention further relates to methods for producing a mutant nucleic acid sequence, comprising introducing at least one mutation into the mature polypeptide coding sequence of SEQ ID NO: 23 or SEQ ID NO: 25 or a subsequence thereof, wherein the mutant nucleic acid sequence encodes a polypeptide which consists of 1 to 485 of SEQ ID NO: 24 or SEQ ID NO: 26 or a fragment thereof which has alpha-amylase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used. These other procedures include gene shuffling, e.g., as described in WO 95/22625 (from Affymax Technologies N.V.) and WO 96/00343 (from Novo Nordisk A/S).

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

Promoter Sequence

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Terminator Sequence

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Signal Peptide

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Regulatory System

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell genome or autonomous replication of the vector in the cell independent of the genome of the cell.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus* or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

Methods of Production

The present invention also relates to methods for producing an alpha-amylase of the present invention comprising (a) cultivating a strain, which in its wild-type form is capable of producing the polypeptide, to produce a supernatant comprising the polypeptide; and (b) recovering the polypeptide. Preferably, the strain is of the genus *Bacillus* sp The present invention also relates to methods for producing an alpha-amylase of the present invention comprising (a) cultivating a host cell under conditions conducive for production of the polypeptide; and (b) recovering the polypeptide.

The present invention also relates to methods for producing an alpha-amylase of the present invention comprising (a) cultivating a host cell under conditions conducive for production of the polypeptide, wherein the host cell comprises a mutant nucleic acid sequence having at least one mutation in the mature polypeptide coding region of SEQ ID NO: 23 or SEQ ID NO: 25, wherein the mutant nucleic acid sequence encodes a polypeptide which consists of amino acids 1 to 485 of SEQ ID NO: 24 or SEQ ID NO: 26, and (b) recovering the polypeptide.

Mutant Alpha-Amylase

The present invention also relates to alpha-amylase mutants.

The Termamyl-Like Alpha-Amylase

It is well known that a number of alpha-amylases produced by *Bacillus* spp. are highly homologous on the amino acid level. For instance, the *B. licheniformis* alpha-amylase comprising the amino acid sequence shown in SEQ ID NO: 4 (commercially available as Termamyl™) has been found to be about 89% homologous with the *B. amyloliquefaciens* alpha-amylase comprising the amino acid sequence shown in SEQ ID NO: 5 and about 79% homologous with the *B. stearothermophilus* alpha-amylase comprising the amino acid sequence shown in SEQ ID NO: 3. Further homologous alpha-amylases include an alpha-amylase derived from a strain of the *Bacillus* sp. NCIB 12289, NCIB 12512, NCIB 12513 or DSM 9375, all of which are described in detail in WO 95/26397, and the alpha-amylase described by Tsukamoto et al., Biochemical and Biophysical Research Communications, 151 (1988), pp. 25-31. Also the novel alpha-amylase of the invention, of which a specific embodiment is shown in SEQ ID NO: 24 (and SEQ ID NO: 26), is contemplated as the parent alpha-amylase to be mutated according to the invention.

Still further homologous alpha-amylases include the alpha-amylase produced by the *B. licheniformis* strain described in EP 0252666 (ATCC 27811), and the alpha-amylases identified in WO 91/00353 and WO 94/18314. Other commercial Termamyl-like *B. licheniformis* alpha-amylases are Duramyl™ from Novo Nordisk, Optitherm™ and Takatherm™ (available from Solvay), Maxamyl™ (available from Gist-brocades/Genencor), Spezym AA™ and Spezyme Delta AA™ (available from Genencor), and Keistase™ (available from Daiwa).

Because of the substantial homology found between these alpha-amylases, they are considered to belong to the same class of alpha-amylases, namely the class of "Termamyl-like alpha-amylases".

Accordingly, in the present context, the term "Termamyl-like alpha-amylase" is intended to indicate an alpha-amylase which, at the amino acid level, exhibits a substantial homology to Termamyl™, i.e., the *B. licheniformis* alpha-amylase having the amino acid sequence shown in SEQ ID NO: 4 herein. In other words, a Termamyl-like alpha-amylase is an alpha-amylase which has the amino acid sequence shown in SEQ ID NOS: 1, 2, 3, 4, 5, 6, 7 or 8 herein, and the amino acid sequence shown in SEQ ID NO: 1 of WO 95/26397 (the same as the amino acid sequence shown as SEQ ID NO: 7 herein) or in SEQ ID NO: 2 of WO 95/26397 (the same as the amino acid sequence shown as SEQ ID NO: 8 herein) or in Tsukamoto et al., 1988, (which amino acid sequence is shown in SEQ ID NO: 6 herein) or i) which displays at least 60%, preferred at least 70%, more preferred at least 75%, even more preferred at least 80%, especially at least 85%, especially preferred at least 90%, even especially more preferred at least 95% homology with at least one of said amino acid sequences shown in SEQ ID NOS: 1 or 2 or 3 or 4 or 5 or 6 or 7 or 8 and/or ii) displays immunological cross-reactivity with an antibody raised against at least one of said alpha-amylases, and/or iii) is encoded by a DNA sequence which hybridizes to the DNA sequences encoding the above-specified alpha-amylases which are apparent from SEQ ID NOS: 9, 10, 11, 12 or 13 of the present application (which encoding sequences encode the amino acid sequences shown in SEQ ID NOS: 1, 2, 3, 4 and 5 herein, respectively), from SEQ ID NO: 4 of WO 95/26397 (which DNA sequence, together with the stop codon TAA, is shown in SEQ ID NO: 14 herein and encodes the amino acid sequence shown in SEQ ID NO: 8 herein) and from SEQ ID NO: 5 of WO 95/26397 (shown in SEQ ID NO: 15 herein), respectively.

In connection with property i), the "homology" may be determined by use of any conventional algorithm, preferably by use of the GAP progamme from the GCG package version 7.3 (June 1993) using default values for GAP penalties, which is a GAP creation penalty of 3.0 and GAP extension penalty of 0.1, (Genetic Computer Group (1991) Programme Manual for the GCG Package, version 7, 575 Science Drive, Madison, Wis., USA 53711).

A structural alignment between Termamyl and a Termamyl-like alpha-amylase may be used to identify equivalent/corresponding positions in other Termamyl-like alpha-amylases. One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., (1987), FEBS LETTERS 224, pp. 149-155) and reverse threading (Huber, T; Torda, A E, PROTEIN SCIENCE Vol. 7, No. 1 pp. 142-149 (1998).

Property ii) of the alpha-amylase, i.e., the immunological cross reactivity, may be assayed using an antibody raised against, or reactive with, at least one epitope of the relevant Termamyl-like alpha-amylase. The antibody, which may either be monoclonal or polyclonal, may be pro-duced by methods known in the art, e.g. as described by Hudson et al., Practical Immunology, Third edition (1989), Blackwell Scientific Publications. The immunological cross-reactivity may be determined using assays known in the art, examples of which are Western Blotting or radial immunodiffusion assay, e.g., as described by Hudson et al., 1989. In this respect, immunological cross-reactivity between the alpha-amylases having the amino acid sequences SEQ ID NOS: 1, 2, 3, 4, 5, 6, 7, or 8 respectively, have been found.

The oligonucleotide probe used in the characterization of the Termamyl-like alpha-amylase in accordance with property iii) above may suitably be prepared on the basis of the full or partial nucleotide or amino acid sequence of the alpha-amylase in question.

Suitable conditions for testing hybridization involve pre-soaking in 5×SSC and prehybridizing for 1 hour at ~40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP for 18 hours at ~40° C., followed by three times washing of the filter in 2×SSC, 0.2% SDS at 40° C. for 30 minutes (low stringency), preferred at 50° C. (medium stringency), more preferably at 65° C. (high stringency), even more preferably at ~75° C. (very high stringency). More details about the hybridization method can be found in Sambrook et al., Molecular_Cloning: A Laboratory Manual, 2nd Ed., Cold Spring Harbor, 1989.

In the present context, "derived from" is intended not only to indicate an alpha-amylase produced or producible by a strain of the organism in question, but also an alpha-amylase encoded by a DNA sequence isolated from such strain and produced in a host organism transformed with said DNA sequence. Finally, the term is intended to indicate an alpha-amylase which is encoded by a DNA sequence of synthetic and/or cDNA origin and which has the identifying characteristics of the alpha-amylase in question. The term is also intended to indicate that the parent alpha-amylase may be a variant of a naturally occurring alpha-amylase, i.e., a variant which is the result of a modification (insertion, substitution, deletion) of one or more amino acid residues of the naturally occurring alpha-amylase.

Parent Hybrid Alpha-Amylases

The parent alpha-amylase may be a hybrid alpha-amylase, i.e., an alpha-amylase which comprises a combination of partial amino acid sequences derived from at least two alpha-amylases.

The parent hybrid alpha-amylase may be one which on the basis of amino acid homology and/or immunological cross-reactivity and/or DNA hybridization (as defined above) can be determined to belong to the Termamyl-like alpha-amylase family. In this case, the hybrid alpha-amylase is typically composed of at least one part of a Termamyl-like alpha-amylase and part(s) of one or more other alpha-amylases selected from Termamyl-like alpha-amylases or non-Termamyl-like alpha-amylases of microbial (bacterial or fungal) and/or mammalian origin.

Thus, the parent hybrid alpha-amylase may comprise a combination of partial amino acid sequences deriving from at least two Termamyl-like alpha-amylases, or from at least one Termamyl-like and at least one non-Termamyl-like bacterial alpha-amylase, or from at least one Termamyl-like and at least one fungal alpha-amylase. The Termamyl-like alpha-amylase from which a partial amino acid sequence derives may, e.g., be any of those specific Termamyl-like alpha-amylases referred to herein.

For instance, the parent alpha-amylase may comprise a C-terminal part of an alpha-amylase derived from a strain of B. licheniformis, and a N-terminal part of an alpha-amylase derived from a strain of B. amyloliquefaciens or from a strain of B. stearothermophilus. For instance, the parent alpha-amylase may comprise at least 430 amino acid residues of the C-terminal part of the B. licheniformis alpha-amylase, and may, e.g., comprise a) an amino acid segment corresponding to the 37 N-terminal amino acid residues of the B. amyloliquefaciens alpha-amylase having the amino acid sequence shown in SEQ ID NO: 5 and an amino acid segment corresponding to the 445 C-terminal amino acid residues of the B. licheniformis alpha-amylase having the amino acid sequence shown in SEQ ID NO: 4, or b) an amino acid segment corresponding to the 68 N-terminal amino acid residues of the B. stearothermophilus alpha-amylase having the amino acid sequence shown in SEQ ID NO: 3 and an amino acid segment corresponding to the 415 C-terminal amino acid residues of the B. licheniformis alpha-amylase having the amino acid sequence shown in SEQ ID NO: 4.

The non-Termamyl-like alpha-amylase may, e.g., be a fungal alpha-amylase, a mammalian or a plant alpha-amylase or a bacterial alpha-amylase (different from a Termamyl-like alpha-amylase). Specific examples of such alpha-amylases include the *Aspergillus oryzae* TAKA alpha-amylase, the *A. niger* acid alpha-amylase, the *Bacillus subtilis* alpha-amylase, the porcine pancreatic alpha-amylase and a barley alpha-amylase. All of these alpha-amylases have elucidated structures which are markedly different from the structure of a typical Termamyl-like alpha-amylase as referred to herein.

The fungal alpha-amylases mentioned above, i.e., derived from *A. niger* and *A. oryzae*, are highly homologous on the amino acid level and generally considered to belong to the same family of alpha-amylases. The fungal alpha-amylase derived from *Aspergillus oryzae* is commercially available under the tradename Fungamyl™.

Furthermore, when a particular variant of a Termamyl-like alpha-amylase (variant of the invention) is referred to—in a conventional manner—by reference to modification (e.g. deletion or substitution) of specific amino acid residues in the amino acid sequence of a specific Termamyl-like alpha-amylase, it is to be understood that variants of another Termamyl-like alpha-amylase modified in the equivalent position(s) (as determined from the best possible amino acid sequence alignment between the respective amino acid sequences) are encompassed thereby.

A preferred embodiment of a variant of the invention is one derived from a B. licheniformis alpha-amylase (as parent Termamyl-like alpha-amylase), e.g., one of those referred to above, such as the B. licheniformis alpha-amylase having the amino acid sequence shown in SEQ ID NO: 4.

Construction of Variants of the Invention

The construction of the variant of interest may be accomplished by cultivating a microorganism comprising a DNA sequence encoding the variant under conditions which are conducive for producing the variant. The variant may then subsequently be recovered from the resulting culture broth. This is described in detail further below.

Altered Properties of Variants of the Invention

The following discusses the relationship between mutations which may be present in variants of the invention, and desirable alterations in properties (relative to those a parent, Termamyl-like alpha-amylase) which may result therefrom.
Increased Thermostability at Acidic pH and/or at Low $Ca^{2+}$ Concentration Mutations of particular relevance in relation to obtaining variants according to the invention having increased thermostability at acidic pH and/or at low $Ca^{2+}$ concentration include mutations at the following positions (relative to B. licheniformis alpha-amylase, SEQ ID NO: 4):
H156, N172, A181, N188, N190, H205, D207, A209, A210, E211, Q264, N265.

In the context of the invention the term "acidic pH" means a pH below 7.0, especially below the pH range, in which industrial starch liquefaction processes are normally performed, which is between pH 5.5 and 6.2.

In the context of the present invention the term "low Calcium concentration" means concentrations below the normal level used in industrial starch liquefaction. Normal concentrations vary depending of the concentration of free $Ca^{2+}$ in the corn. Normally a dosage corresponding to 1 mM (40 ppm) is added which together with the level in corn gives between 40 and 60 ppm free $Ca^{2+}$.

In the context of the invention the term "high tempertatures" means temperatures between 95° C. and 160° C., especially the temperature range in which industrial starch liquefaction processes are normally performed, which is between 95° C. and 105° C.

The inventors have now found that the thermostability at acidic pH and/or at low $Ca^{2+}$ concentration may be increased even more by combining certain mutations including the above mentioned mutations and/or I201 with each other.

Said "certain" mutations are the following (relative to B. licheniformis alpha-amylase, SEQ ID NO: 4):
N190, D207, E211, Q264 and I201.

Said mutation may further be combined with deletions in one, preferably two or even three positions as described in WO 96/23873 (i.e., in positions R181, G182, T183, G184 in SEQ ID NO: 1 herein). According to the invention variants of a parent Termamyl-like alpha-amylase with alpha-amylase activity comprising mutations in two, three, four, five or six of the above positions are contemplated.

It should be emphasized that not only the Termamyl-like alpha-amylases mentioned specifically below are contemplated. Also other commercial Termamyl-like alpha-amylases are contemplated. An unexhaustive list of such alpha-amylases is the following:
alpha-amylases produced by the B. licheniformis strain described in EP 0252666 (ATCC 27811), and the alpha-amylases identified in WO 91/00353 and WO 94/18314. Other commercial Termamyl-like B. licheniformis alpha-amylases are Optitherm™ and Takatherm™ (available from Solvay), Maxamyl™ (available from Gist-brocades/Genencor), Spezym AA™ Spezyme Delta AA™ (available from Genencor), and Keistase™ (available from Daiwa).

It may be mentioned here that amino acid residues, respectively, at positions corresponding to N190, I201, D207 and E211, respectively, in SEQ ID NO: 4 constitute amino acid residues which are conserved in numerous Termamyl-like alpha-amylases. Thus, for example, the corresponding positions of these residues in the amino acid sequences of a number of Termamyl-like alpha-amylases which have already been mentioned (vide supra) are as follows:

TABLE 1

| Termamyl-like alpha-amylase | N | I | D | E | Q |
|---|---|---|---|---|---|
| licheniformis (SEQ ID NO: 4) | N190 | I201 | D207 | E211 | Q264 |
| B. amyloliquefaciens (SEQ ID NO: 5) | N190 | V201 | D207 | E211 | Q264 |
| B. stearothermophilus (SEQ ID NO: 3) | N193 | L204 | E210 | E214 | — |
| Bacillus WO 95/26397 (SEQ ID NO: 2) | N195 | V206 | E212 | E216 | — |
| Bacillus WO 95/26397 (SEQ ID NO: 1) | N195 | V206 | E212 | E216 | — |
| "Bacillus sp. #707" (SEQ ID NO: 6) | N195 | I206 | E212 | E216 | — |
| Bacillus sp. AA560 (SEQ ID NO: 24) | N195 | I206 | E212 | E216 | — |

Mutations of these conserved amino acid residues are very important in relation to improving thermostability at acidic pH and/or at low calcium concentration, and the following mutations are of particular interest in this connection (with reference to the numbering of the B. licheniformis amino acid sequence shown in SEQ ID NO: 4).

Pair-wise amino acid deletions at positions corresponding to R179-G182 in SEQ ID NO: 5 corresponding to a gap in SEQ ID NO: 4. when aligned with a numerous Termamyl-like alpha-amylases. Thus, for example, the corresponding positions of these residues in the amino acid sequences of a number of Termamyl-like alpha-amylases which have already been mentioned (vide supra) are as follows:

TABLE 2

| Termamyl-like alpha-amylase | Pair wise amino acid deletions among |
|---|---|
| B. amyloliquefaciens (SEQ ID NO: 5) | R176, G177, E178, G179 |
| B. stearothermophilus (SEQ ID NO: 3) | R179, G180, I181, G182 |
| Bacillus WO 95/26397 (SEQ ID NO: 2) | R181, G182, T183, G184 |
| Bacillus WO 95/26397 (SEQ ID NO: 1) | R181, G182, D183, G184 |
| Bacillus sp. #707" (SEQ ID NO: 6) | R181, G182, H183, G184 |
| Bacillus sp. (AA560) (SEQ ID NO: 24) | R181, G182, H183, G184 |

When using SEQ ID NO: 1-6 or SEQ ID NO: 24 (or SEQ ID NO: 26) as the backbone (i.e., as the parent Termamyl-like alpha-amylase) two, three, four, five or six mutations may according to the invention be made in the following regions/positions to increase the thermostability at acidic pH and/or at low $Ca^{2+}$ concentrations (relative to the parent):
(relative to SEQ ID NO: 1 herein):
1: R181*, G182*, T183*, G184*
2: N195A,R,D,C,E,Q,G,H,I,L,K,M,F,P,S,T,W,Y,V;
3: V206A,R,D,N,C,E,Q,G,H,I,L,K,M,F,P,S,T,W,Y;
4: E212A,R,D,N,C,Q,G,H,I,L,K,M,F,P,S,T,W,Y,V;
5: E216A,R,D,N,C,Q,G,H,I,L,K,M,F,P,S,T,W,Y,V;
6: K269A,R,D,N,C,E,Q,G,H,I,L,M,F,P,S,T,W,Y,V;
(relative to SEQ ID NO: 2 herein):
1: R181*,G182*,D183*,G184*
2: N195A,R,D,C,E,Q,G,H,I,L,K,M,F,P,S,T,W,Y,V;
3: V206A,R,D,N,C,E,Q,G,H,I,L,K,M,F,P,S,T,W,Y;
4: E212A,R,D,N,C,Q,G,H,I,L,K,M,F,P,S,T,W,Y,V;
5: E216A,R,D,N,C,Q,G,H,I,L,K,M,F,P,S,T,W,Y,V;
6: K269A,R,D,N,C,E,Q,G,H,I,L,M,F,P,S,T,W,Y,V;
(Relative to SEQ ID NO: 3 herein):
1: R179*,G180, I181*,G182*
2: N193A,R,D,C,E,Q,G,H,I,L,K,M,F,P,S,T,W,Y,V;
3: L204A,R,D,N,C,E,Q,G,H,I,K,M,F,P,S,T,W,Y,V;
4: E210A,R,D,N,C,Q,G,H,I,L,K,M,F,P,S,T,W,Y,V;
5: E214A,R,D,N,C,Q,G,H,I,L,K,M,F,P,S,T,W,Y,V;
6: S267A,R,D,N,C,E,Q,G,H,I,L,K,M,F,P,T,W,Y,V Relative to SEQ ID NO: 4 herein):
1: Q178*,G179*
2: N190A,R,D,C,E,Q,G,H,I,L,K,M,F,P,S,T,W,Y,V;
3: I201A,R,D,N,C,E,Q,G,H,I,L,K,M,F,P,S,T,W,Y,V;
4: D207A,R,N,C,E,Q,G,H,I,L,K,M,F,P,S,T,W,Y,V;
5: E211A,R,D,N,C,Q,G,H,I,L,K,M,F,P,S,T,W,Y,V;
6: Q264A,R,D,N,C,E,G,H,I,L,K,M,F,P,S,T,W,Y,V;
(relative to SEQ ID NO: 5 herein):
1: R176*,G177*,E178,G179*
2: N190A,R,D,C,E,Q,G,H,I,L,K,M,F,P,S,T,W,Y,V;
3: V201A,R,D,N,C,E,Q,G,H,I,L,K,M,F,P,S,T,W,Y;
4: D207A,R,N,C,E,Q,G,H,I,L,K,M,F,P,S,T,W,Y,V;
5: E211A,R,D,N,C,Q,G,H,I,L,K,M,F,P,S,T,W,Y,V;
6: Q264A,R,D,N,C,E,G,H,I,L,K,M,F,P,S,T,W,Y,V;
(relative to SEQ ID NO: 6 herein):
1: R181*,G182*,H183*,G184*
2: N195A,R,D,C,E,Q,G,H,I,L,K,M,F,P,S,T,W,Y,V;
3: I206A,R,D,N,C,E,Q,G,H,L,K,M,F,P,S,T,W,Y,V;
4: E212A,R,D,N,C,Q,G,H,I,L,K,M,F,P,S,T,W,Y,V;
5: E216A,R,D,N,C,Q,G,H,I,L,K,M,F,P,S,T,W,Y,V;
6: K269A,R,D,N,C,E,Q,G,H,I,L,M,F,P,S,T,W,Y,V; and
(relative to SEQ ID NO: 24)
1: R181*,G182*,H183*,G184*
2: N195A,R,D,C,E,Q,G,H,I,L,K,M,F,P,S,T,W,Y,V;
3: I206A,R,D,N,C,E,Q,G,H,L,K,M,F,P,S,T,W,Y,V;
4: E212A,R,D,N,C,Q,G,H,I,L,K,M,F,P,S,T,W,Y,V;
5: E216A,R,D,N,C,Q,G,H,I,L,K,M,F,P,S,T,W,Y,V;
6: K269A,R,D,N,C,E,Q,G,H,I,L,M,F,P,S,T,W,Y,V.

Contemplated according to the present invention is combining three, four, five or six mutation.

Specific double mutations for backbone SEQ ID NO: 1-6 and SEQ ID NO: 24 and SEQ ID NO: 26 are listed in the following.

Using SEQ ID NO: 1 as the backbone the following double mutations are contemplated according to the invention:
R181*/G182*/N195A,R,D,C,E,Q,G,H,I,L,K,M,F,P,S,T,W,Y,V;
G182*/T183*/N195A,R,D,C,E,Q,G,H,I,L,K,M,F,P,S,T,W,Y,V;
T183*/G184*/N195A,R,D,C,E,Q,G,H,I,L,K,M,F,P,S,T,W,Y,V;
R181*/G182*/V206A,R,D,N,C,E,Q,G,H,I,L,K,M,F,P,S,T,W,Y;
G182*/T183*/V206A,R,D,N,C,E,Q,G,H,I,L,K,M,F,P,S,T,W,Y;
T183*/G184*/V206A,R,D,N,C,E,Q,G,H,I,L,K,M,F,P,S,T,W,Y;
R181*/G182*/E212A,R,D,N,C,Q,G,H,I,L,K,M,F,P,S,T,W,Y,V;
G182*/T183*/E212A,R,D,N,C,Q,G,H,I,L,K,M,F,P,S,T,W,Y,V;
T183*/G184*/E212A,R,D,N,C,Q,G,H,I,L,K,M,F,P,S,T,W,Y,V;
R181*/G182*/E216A,R,D,N,C,Q,G,H,I,L,K,M,F,P,S,T,W,Y,V;
G182*/T183*/E216A,R,D,N,C,Q,G,H,I,L,K,M,F,P,S,T,W,Y,V;
T183*/G184*/E216A,R,D,N,C,Q,G,H,I,L,K,M,F,P,S,T,W,Y,V;
R181*/G182*/K269A,R,D,N,C,E,Q,G,H,I,L,M,F,P,S,T,W,Y,V;
G182*/T183*/K269A,R,D,N,C,E,Q,G,H,I,L,M,F,P,S,T,W,Y,V;
T183*/G184*/K269A,R,D,N,C,E,Q,G,H,I,L,M,F,P,S,T,W,Y,V;
N195A,R,D,C,E,Q,G,H,I,L,K,M,F,P,S,T,W,Y,V/V206A,R,D,N,C,E,Q,G,H,I,L,K,M,F,P,S,T,W,Y;
N195A,R,D,C,E,Q,G,H,I,L,K,M,F,P,S,T,W,Y,V/E212A,R,D,N,C,Q,G,H,I,L,K,M,F,P,S,T,W,Y,V;
N195A,R,D,C,E,Q,G,H,I,L,K,M,F,P,S,T,W,Y,V/E216A,R,D,N,C,Q,G,H,I,L,K,M,F,P,S,T,W,Y,V;
N195A,R,D,C,E,Q,G,H,I,L,K,M,F,P,S,T,W,Y,V/K269A,R,D,N,C,E,Q,G,H,I,L,M,F,P,S,T,W,Y,V;
V206A,R,D,N,C,E,Q,G,H,I,L,K,M,F,P,S,T,W,Y/E212A,R,D,N,C,Q,G,H,I,L,K,M,F,P,S,T,W,Y,V;
V206A,R,D,N,C,E,Q,G,H,I,L,K,M,F,P,S,T,W,Y/E216A,R,D,N,C,Q,G,H,I,L,K,M,F,P,S,T,W,Y,V;
V206A,R,D,N,C,E,Q,G,H,I,L,K,M,F,P,S,T,W,Y/K269A,R,D,N,C,E,Q,G,H,I,L,M,F,P,S,T,W,Y,V;
E212A,R,D,N,C,Q,G,H,I,L,K,M,F,P,S,T,W,Y,V/E216A,R,D,N,C,Q,G,H,I,L,K,M,F,P,S,T,W,Y,V;
E212A,R,D,N,C,Q,G,H,I,L,K,M,F,P,S,T,W,Y,V/K269A,R,D,N,C,E,Q,G,H,I,L,M,F,P,S,T,W,Y,V;
E216A,R,D,N,C,Q,G,H,I,L,K,M,F,P,S,T,W,Y,V/K269A,R,D,N,C,E,Q,G,H,I,L,M,F,P,S,T,W,Y,V;

Using SEQ ID NO: 2 as the backbone the following double mutations are contemplated according to the invention:
R181*/G182*/N195A,R,D,C,E,Q,G,H,I,L,K,M,F,P,S,T,W,Y,V;
G182*/D183*/N195A,R,D,C,E,Q,G,H,I,L,K,M,F,P,S,T,W,Y,V;
D183*/G184*/N195A,R,D,C,E,Q,G,H,I,L,K,M,F,P,S,T,W,Y,V;
R181*/G182*/V206A,R,D,N,C,E,Q,G,H,I,L,K,M,F,P,S,T,W,Y;
G182*/T183*/V206A,R,D,N,C,E,Q,G,H,I,L,K,M,F,P,S,T,W,Y;
T183*/G184*/V206A,R,D,N,C,E,Q,G,H,I,L,K,M,F,P,S,T,W,Y;
R181*/G182*/E212A,R,D,N,C,Q,G,H,I,L,K,M,F,P,S,T,W,Y,V;
G182*/T183*/E212A,R,D,N,C,Q,G,H,I,L,K,M,F,P,S,T,W,Y,V;
T183*/G184*/E212A,R,D,N,C,Q,G,H,I,L,K,M,F,P,S,T,W,Y,V;
R181*/G182*/E216A,R,D,N,C,Q,G,H,I,L,K,M,F,P,S,T,W,Y,V;
G182*/T183*/E216A,R,D,N,C,Q,G,H,I,L,K,M,F,P,S,T,W,Y,V;
T183*/G184*/E216A,R,D,N,C,Q,G,H,I,L,K,M,F,P,S,T,W,Y,V;
R181*/G182*/K269A,R,D,N,C,E,Q,G,H,I,L,M,F,P,S,T,W,Y,V;
G182*/T183*/K269A,R,D,N,C,E,Q,G,H,I,L,M,F,P,S,T,W,Y,V;
T183*/G184*/K269A,R,D,N,C,E,Q,G,H,I,L,M,F,P,S,T,W,Y,V;
N195 A,R,D,C,E,Q,G,H,I,L,K,M,F,P,S,T,W,Y,V/V206A,R,D,N,C,E,Q,G,H,I,L,K,M,F,P,S,T,W,Y;
N195A,R,D,C,E,Q,G,H,I,L,K,M,F,P,S,T,W,Y,V/E212A,R,D,N,C,Q,G,H,I,L,K,M,F,P,S,T,W,Y,V;
N195A,R,D,C,E,Q,G,H,I,L,K,M,F,P,S,T,W,Y,V/E216A,R,D,N,C,Q,G,H,I,L,K,M,F,P,S,T,W,Y,V;
N195A,R,D,C,E,Q,G,H,I,L,K,M,F,P,S,T,W,Y,V/K269A,R,D,N,C,E,Q,G,H,I,L,M,F,P,S,T,W,Y,V;
V206A,R,D,N,C,E,Q,G,H,I,L,K,M,F,P,S,T,W,Y/E212A,R,D,N,C,Q,G,H,I,L,K,M,F,P,S,T,W,Y,V;
V206A,R,D,N,C,E,Q,G,H,I,L,K,M,F,P,S,T,W,Y/E216A,R,D,N,C,Q,G,H,I,L,K,M,F,P,S,T,W,Y,V;
V206A,R,D,N,C,E,Q,G,H,I,L,K,M,F,P,S,T,W,Y/K269A,R,D,N,C,E,Q,G,H,I,L,M,F,P,S,T,W,Y,V;
E212A,R,D,N,C,Q,G,H,I,L,K,M,F,P,S,T,W,Y,V/E216A,R,D,N,C,Q,G,H,I,L,K,M,F,P,S,T,W,Y,V;

E212A,R,D,N,C,Q,G,H,I,L,K,M,F,P,S,T,W,Y,V/K269A, R,D,N,C,E,Q,G,H,I,L,M,F,P,S,T,W,Y,V;
E216A,R,D,N,C,Q,G,H,I,L,K,M,F,P,S,T,W,Y,V/K269A, R,D,N,C,E,Q,G,H,I,L,M,F,P,S,T,W,Y,V;

Using SEQ ID NO: 3 as the backbone the following double mutations are contemplated according to the invention:

R179*/G180*/N193A,R,D,C,E,Q,G,H,I,L,K,M,F,P,S,T,W,Y,V;
G180*/I181*/N193A,R,D,C,E,Q,G,H,I,L,K,M,F,P,S,T,W,Y,V;
I181*/G182*/N193A,R,D,C,E,Q,G,H,I,L,K,M,F,P,S,T,W,Y,V;
R179*/G180*/L204A,R,D,N,C,E,Q,G,H,I,K,M,F,P,S,T,W,Y,V;
G180*/I181*/L204A,R,D,N,C,E,Q,G,H,I,K,M,F,P,S,T,W,Y,V;
I181*/G182*/L204A,R,D,N,C,E,Q,G,H,I,K,M,F,P,S,T,W,Y,V;
R179*/G180*/E210A,R,D,N,C,Q,G,H,I,L,K,M,F,P,S,T,W,Y,V;
G180*/I181*/E210A,R,D,N,C,Q,G,H,I,L,K,M,F,P,S,T,W,Y,V;
I181*/G182*/E210A,R,D,N,C,Q,G,H,I,L,K,M,F,P,S,T,W,Y,V;
R179*/G180*/E214A,R,D,N,C,Q,G,H,I,L,K,M,F,P,S,T, W,Y,V;
G180*/I181*/E214A,R,D,N,C,Q,G,H,I,L,K,M,F,P,S,T, W,Y,V;
I181*/G182*/E214A,R,D,N,C,Q,G,H,I,L,K,M,F,P,S,T, W,Y,V;
R179*/G180*/S267A,R,D,N,C,E,Q,G,H,I,L,K,M,F,P,T, W,Y,V;
G180*/I181*/S267A,R,D,N,C,E,Q,G,H,I,L,K,M,F,P,T, W,Y,V;
I181*/G182*/S267A,R,D,N,C,E,Q,G,H,I,L,K,M,F,P,T, W,Y,V;
N193A,R,D,C,E,Q,G,H,I,L,K,M,F,P,S,T,W,Y,V/L204A, R,D,N,C,E,Q,G,H,I,K,M,F,P,S,T,W,Y,V;
N193A,R,D,C,E,Q,G,H,I,L,K,M,F,P,S,T,W,Y,V/E210A, R,D,N,C,Q,G,H,I,L,K,M,F,P,S,T,W,Y,V;
N193A,R,D,C,E,Q,G,H,I,L,K,M,F,P,S,T,W,Y,V/E214A, R,D,N,C,Q,G,H,I,L,K,M,F,P,S,T,W,Y,V;
N193A,R,D,C,E,Q,G,H,I,L,K,M,F,P,S,T,W,Y,V/S267A, R,D,N,C,E,Q,G,H,I,L,K,M,F,P,T,W,Y,V;
L204A,R,D,N,C,E,Q,G,H,I,K,M,F,P,S,T,W,Y,V/E210A, R,D,N,C,Q,G,H,I,L,K,M,F,P,S,T,W,Y,V;
L204A,R,D,N,C,E,Q,G,H,I,K,M,F,P,S,T,W,Y,V/E214A, R,D,N,C,Q,G,H,I,L,K,M,F,P,S,T,W,Y,V;
L204A,R,D,N,C,E,Q,G,H,I,K,M,F,P,S,T,W,Y,V/S267A, R,D,N,C,E,Q,G,H,I,L,K,M,F,P,T,W,Y,V;
E210A,R,D,N,C,Q,G,H,I,L,K,M,F,P,S,T,W,Y,V/E216A, R,D,N,C,Q,G,H,I,L,K,M,F,P,S,T,W,Y,V;
E210A,R,D,N,C,Q,G,H,I,L,K,M,F,P,S,T,W,Y,V/S267A, R,D,N,C,E,Q,G,H,I,L,K,M,F,P,T,W,Y,V;
E214A,R,D,N,C,Q,G,H,I,L,K,M,F,P,S,T,W,Y,V/S267A, R,D,N,C,E,Q,G,H,I,L,K,M,F,P,T,W,Y,V;

Using SEQ ID NO: 4 as the backbone the following double mutations are contemplated according to the invention:

Q178*/G179*/N190A,R,D,C,E,Q,G,H,I,L,K,M,F,P,S,T, W,Y,V;
Q178*/G179*/I201A,R,D,N,C,E,Q,G,H,L,K,M,F,P,S,T, W,Y,V;
Q178*/G 179*/D207A,R,N,C,E,Q,G,H,I,L,K,M,F,P,S,T, W,Y,V;
Q178*/G179*/E211A,R,D,N,C,Q,G,H,I,L,K,M,F,P,S,T, W,Y,V;
R179*/G180*/Q264A,R,D,N,C,E,G,H,I,L,K,M,F,P,S,T, W,Y,V;
N190/I201A,R,D,N,C,E,Q,G,H,L,K,M,F,P,S,T,W,Y,V;
N190/D207A,R,N,C,E,Q,G,H,I,L,K,M,F,P,S,T,W,Y,V;
N190/E211A,R,D,N,C,Q,G,H,I,L,K,M,F,P,S,T,W,Y,V;
N190/Q264A,R,D,N,C,E,G,H,I,L,K,M,F,P,S,T,W,Y,V;
I201/D207A,R,N,C,Q,E,G,H,I,L,K,M,F,P,S,T,W,Y,V;
I201/E211A,R,D,N,C,Q,G,H,I,L,K,M,F,P,S,T,W,Y,V;
I201/Q264A,R,D,N,C,E,G,H,I,L,K,M,F,P,S,T,W,Y,V;
D207/E211A,R,D,N,C,Q,G,H,I,L,K,M,F,P,S,T,W,Y,V;
D207/Q264A,R,D,N,C,E,G,H,I,L,K,M,F,P,S,T,W,Y,V;
E211/Q264A,R,D,N,C,E,G,H,I,L,K,M,F,P,S,T,W,Y,V;

Using SEQ ID NO: 5 as the backbone the following double mutations are contemplated according to the invention:

R176*/G177*/N190A,R,D,C,E,Q,G,H,I,L,K,M,F,P,S,T, W,Y,V;
G177*/E178*/N190A,R,D,C,E,Q,G,H,I,L,K,M,F,P,S,T, W,Y,V;
E178*/G179*/N190A,R,D,C,E,Q,G,H,I,L,K,M,F,P,S,T, W,Y,V;
R176*/G177*N201A,R,D,N,C,E,Q,G,H,I,L,K,M,F,P,S,T, W,Y;
G176*/E178*N201A,R,D,N,C,E,Q,G,H,I,L,K,M,F,P,S,T, W,Y;
E178*/G179*N201A,R,D,N,C,E,Q,G,H,I,L,K,M,F,P,S,T, W,Y;
R176*/G177*/D207A,R,N,C,E,Q,G,H,I,L,K,M,F,P,S,T, W,Y,V;
G177*/E178*/D207A,R,N,C,E,Q,G,H,I,L,K,M,F,P,S,T, W,Y,V;
E178*/G179*/D207A,R,N,C,E,Q,G,H,I,L,K,M,F,P,S,T, W,Y,V;
R176*/G177*/E211A,R,D,N,C,Q,G,H,I,L,K,M,F,P,S,T, W,Y,V;
G177*/E178*/E211A,R,D,N,C,Q,G,H,I,L,K,M,F,P,S,T, W,Y,V;
E178*/G179*/E211A,R,D,N,C,Q,G,H,I,L,K,M,F,P,S,T, W,Y,V;
R176*/G177*/Q264A,R,D,N,C,E,G,H,I,L,K,M,F,P,S,T, W,Y,V;
G177*/E178*/Q264A,R,D,N,C,E,G,H,I,L,K,M,F,P,S,T, W,Y,V;
E178*/G179*/Q264A,R,D,N,C,E,G,H,I,L,K,M,F,P,S,T, W,Y,V;
N190A,R,D,C,E,Q,G,H,I,L,K,M,F,P,S,T,W,Y,V/V201A, R,D,N,C,E,Q,G,H,I,L,K,M,F,P,S,T,W,Y;
N190A,R,D,C,E,Q,G,H,I,L,K,M,F,P,S,T,W,Y,V/D207A, R,N,C,E,Q,G,H,I,L,K,M,F,P,S,T,W,Y,V;
N190A,R,D,C,E,Q,G,H,I,L,K,M,F,P,S,T,W,Y,V/E211A, R,D,N,C,Q,G,H,I,L,K,M,F,P,S,T,W,Y,V;
N190A,R,D,C,E,Q,G,H,I,L,K,M,F,P,S,T,W,Y,V/Q264A, R,D,N,C,E,G,H,I,L,K,M,F,P,S,T,W,Y,V;
V201A,R,D,N,C,E,Q,G,H,I,L,K,M,F,P,S,T,W,Y/D207A, R,N,C,E,Q,G,H,I,L,K,M,F,P,S,T,W,Y,V;
V201A,R,D,N,C,E,Q,G,H,I,L,K,M,F,P,S,T,W,Y/E211A, R,D,N,C,Q,G,H,I,L,K,M,F,P,S,T,W,Y,V;
V201A,R,D,N,C,E,Q,G,H,I,L,K,M,F,P,S,T,W,Y/Q264A, R,D,N,C,E,G,H,I,L,K,M,F,P,S,T,W,Y,V;
D207A,R,N,C,E,Q,G,H,I,L,K,M,F,P,S,T,W,Y,V/E211A, R,D,N,C,Q,G,H,I,L,K,M,F,P,S,T,W,Y,V;
D207A,R,N,C,E,Q,G,H,I,L,K,M,F,P,S,T,W,Y,V/Q264A, R,D,N,C,E,G,H,I,L,K,M,F,P,S,T,W,Y,V;
E211A,R,D,N,C,Q,G,H,I,L,K,M,F,P,S,T,W,Y,V/Q264A, R,D,N,C,E,G,H,I,L,K,M,F,P,S,T,W,Y,V.

Using SEQ ID NO: 6 as the backbone the following double mutations are contemplated according to the invention:

R181*/G182*/N195A,R,D,C,E,Q,G,H,I,L,K,M,F,P,S,T,W,Y,V;
G182*/H183*/N195A,R,D,C,E,Q,G,H,I,L,K,M,F,P,S,T,W,Y,V;
H183*/G184*/N195A,R,D,C,E,Q,G,H,I,L,K,M,F,P,S,T,W,Y,V;
R181*/G182*/I206A,R,D,N,C,E,Q,G,H,L,K,M,F,P,S,T,W,Y,V;
G182*/H183*/I206A,R,D,N,C,E,Q,G,H,L,K,M,F,P,S,T,W,Y,V;
H183*/G184*/I206A,R,D,N,C,E,Q,G,H,L,K,M,F,P,S,T,W,Y,V;
R181*/G182*/E212A,R,D,N,C,Q,G,H,I,L,K,M,F,P,S,T,W,Y,V;
G182*/H183*/E212A,R,D,N,C,Q,G,H,I,L,K,M,F,P,S,T,W,Y,V;
H183*/G184*/E212A,R,D,N,C,Q,G,H,I,L,K,M,F,P,S,T,W,Y,V;
R181*/G182*/E216A,R,D,N,C,Q,G,H,I,L,K,M,F,P,S,T,W,Y,V;
G182*/H183*/E216A,R,D,N,C,Q,G,H,I,L,K,M,F,P,S,T,W,Y,V;
H183*/G184*/E216A,R,D,N,C,Q,G,H,I,L,K,M,F,P,S,T,W,Y,V;
R181*/G182*/K269A,R,D,N,C,E,Q,G,H,I,L,M,F,P,S,T,W,Y,V;
G182*/H183*/K269A,R,D,N,C,E,Q,G,H,I,L,M,F,P,S,T,W,Y,V;
H183*/G184*/K269A,R,D,N,C,E,Q,G,H,I,L,M,F,P,S,T,W,Y,V;
N195A,R,D,C,E,Q,G,H,I,L,K,M,F,P,S,T,W,Y,V/I206A,R,D,N,C,E,Q,G,H,L,K,M,F,P,S,T,W,Y,V;
N195A,R,D,C,E,Q,G,H,I,L,K,M,F,P,S,T,W,Y,V/E212A,R,D,N,C,Q,G,H,I,L,K,M,F,P,S,T,W,Y,V;
N195A,R,D,C,E,Q,G,H,I,L,K,M,F,P,S,T,W,Y,V/E216A,R,D,N,C,Q,G,H,I,L,K,M,F,P,S,T,W,Y,V;
N195A,R,D,C,E,Q,G,H,I,L,K,M,F,P,S,T,W,Y,V/K269A,R,D,N,C,E,Q,G,H,I,L,M,F,P,S,T,W,Y,V;
I206A,R,D,N,C,E,Q,G,H,L,K,M,F,P,S,T,W,Y,V/E212A,R,D,N,C,Q,G,H,I,L,K,M,F,P,S,T,W,Y,V;
I206A,R,D,N,C,E,Q,G,H,L,K,M,F,P,S,T,W,Y,V/E216A,R,D,N,C,Q,G,H,I,L,K,M,F,P,S,T,W,Y,V;
I206A,R,D,N,C,E,Q,G,H,L,K,M,F,P,S,T,W,Y,V/K269A,R,D,N,C,E,Q,G,H,I,L,M,F,P,S,T,W,Y,V;
E212A,R,D,N,C,Q,G,H,I,L,K,M,F,P,S,T,W,Y,V/E216A,R,D,N,C,Q,G,H,I,L,K,M,F,P,S,T,W,Y,V;
E212A,R,D,N,C,Q,G,H,I,L,K,M,F,P,S,T,W,Y,V/K269A,R,D,N,C,E,Q,G,H,I,L,M,F,P,S,T,W,Y,V;
E216A,R,D,N,C,Q,G,H,I,L,K,M,F,P,S,T,W,Y,V/K269A,R,D,N,C,E,Q,G,H,I,L,M,F,P,S,T,W,Y,V.

Using SEQ ID NO: 24 as the backbone the following double mutations are contemplated according to the invention:
R181*/G182*/N195A,R,D,C,E,Q,G,H,I,L,K,M,F,P,S,T,W,Y,V;
G182*/H183*/N195A,R,D,C,E,Q,G,H,I,L,K,M,F,P,S,T,W,Y,V;
H183*/G184*/N195A,R,D,C,E,Q,G,H,I,L,K,M,F,P,S,T,W,Y,V;
R181*/G182*/I206A,R,D,N,C,E,Q,G,H,L,K,M,F,P,S,T,W,Y,V;
G182*/H183*/I206A,R,D,N,C,E,Q,G,H,L,K,M,F,P,S,T,W,Y,V;
H183*/G184*/I206A,R,D,N,C,E,Q,G,H,L,K,M,F,P,S,T,W,Y,V;
R181*/G182*/E212A,R,D,N,C,Q,G,H,I,L,K,M,F,P,S,T,W,Y,V;
G182*/H183*/E212A,R,D,N,C,Q,G,H,I,L,K,M,F,P,S,T,W,Y,V;
H183*/G184*/E212A,R,D,N,C,Q,G,H,I,L,K,M,F,P,S,T,W,Y,V;
R181*/G182*/E216A,R,D,N,C,Q,G,H,I,L,K,M,F,P,S,T,W,Y,V;
G182*/H183*/E216A,R,D,N,C,Q,G,H,I,L,K,M,F,P,S,T,W,Y,V;
H183*/G184*/E216A,R,D,N,C,Q,G,H,I,L,K,M,F,P,S,T,W,Y,V;
R181*/G182*/K269A,R,D,N,C,E,Q,G,H,I,L,M,F,P,S,T,W,Y,V;
G182*/H183*/K269A,R,D,N,C,E,Q,G,H,I,L,M,F,P,S,T,W,Y,V;
H183*/G184*/K269A,R,D,N,C,E,Q,G,H,I,L,M,F,P,S,T,W,Y,V;
N195A,R,D,C,E,Q,G,H,I,L,K,M,F,P,S,T,W,Y,V/I206A,R,D,N,C,E,Q,G,H,L,K,M,F,P,S,T,W,Y,V;
N195A,R,D,C,E,Q,G,H,I,L,K,M,F,P,S,T,W,Y,V/E212A,R,D,N,C,Q,G,H,I,L,K,M,F,P,S,T,W,Y,V;
N195A,R,D,C,E,Q,G,H,I,L,K,M,F,P,S,T,W,Y,V/E216A,R,D,N,C,Q,G,H,I,L,K,M,F,P,S,T,W,Y,V;
N195A,R,D,C,E,Q,G,H,I,L,K,M,F,P,S,T,W,Y,V/K269A,R,D,N,C,E,Q,G,H,I,L,M,F,P,S,T,W,Y,V;
I206A,R,D,N,C,E,Q,G,H,L,K,M,F,P,S,T,W,Y,V/E212A,R,D,N,C,Q,G,H,I,L,K,M,F,P,S,T,W,Y,V;
I206A,R,D,N,C,E,Q,G,H,L,K,M,F,P,S,T,W,Y,V/E216A,R,D,N,C,Q,G,H,I,L,K,M,F,P,S,T,W,Y,V;
I206A,R,D,N,C,E,Q,G,H,L,K,M,F,P,S,T,W,Y,V/K269A,R,D,N,C,E,Q,G,H,I,L,M,F,P,S,T,W,Y,V;
E212A,R,D,N,C,Q,G,H,I,L,K,M,F,P,S,T,W,Y,V/E216A,R,D,N,C,Q,G,H,I,L,K,M,F,P,S,T,W,Y,V;
E212A,R,D,N,C,Q,G,H,I,L,K,M,F,P,S,T,W,Y,V/K269A,R,D,N,C,E,Q,G,H,I,L,M,F,P,S,T,W,Y,V;
E216A,R,D,N,C,Q,G,H,I,L,K,M,F,P,S,T,W,Y,V/K269A,R,D,N,C,E,Q,G,H,I,L,M,F,P,S,T,W,Y,V.

All Termamyl-like alpha-amylase defined above may suitably be used as backbone for preparing variants of the invention.

However, in a preferred embodiment the variant comprises the following mutations: N190F/Q264S in SEQ ID NO: 4 or in corresponding positions in another parent Termamyl-like alpha-amylases.

In another embodiment the variant of the invention comprises the following mutations: I181*/G182*/N193F in SEQ ID NO: 3 (TVB146) or in corresponding positions in another parent Termamyl-like alpha-amylases. Said variant may further comprise a substitution in position E214Q.

In a preferred embodiment of the invention the parent Termamyl-like alpha-amylase is a hybrid alpha-amylase of SEQ ID NO: 4 and SEQ ID NO: 5. Specifically, the parent hybrid Termamyl-like alpha-amylase may be a hybrid alpha-amylase comprising the 445 C-terminal amino acid residues of the *B. licheniformis* alpha-amylase shown in SEQ ID NO: 4 and the 37 N-terminal amino acid residues of the alpha-amylase derived from *B. amyloliquefaciens* shown in SEQ ID NO: 5, which may suitably further have the following mutations: H156Y+A181T+N190F+A209V+Q264S (using the numbering in SEQ ID NO: 4). The latter mentioned hybrid is used in the examples below and is referred to as LE174.

General Mutations of the Invention

It may be preferred that a variant of the invention comprises one or more modifications in addition to those outlined above. Thus, it may be advantageous that one or more proline residues present in the part of the alpha-amylase variant which is modified is/are replaced with a non-proline residue which may be any of the possible, naturally occurring non-proline residues, and which preferably is an alanine, glycine, serine, threonine, valine or leucine.

Analogously, it may be preferred that one or more cysteine residues present among the amino acid residues with which the parent alpha-amylase is modified is/are replaced with a non-cysteine residue such as serine, alanine, threonine, glycine, valine or leucine.

Furthermore, a variant of the invention may—either as the only modification or in combination with any of the above outlined modifications—be modified so that one or more Asp and/or Glu present in an amino acid fragment corresponding to the amino acid fragment 185-209 of SEQ ID NO: 4 is replaced by an Asn and/or Gln, respectively. Also of interest is the replacement, in the Termamyl-like alpha-amylase, of one or more of the Lys residues present in an amino acid fragment corresponding to the amino acid fragment 185-209 of SEQ ID NO: 4 by an Arg.

It will be understood that the present invention encompasses variants incorporating two or more of the above outlined modifications.

Furthermore, it may be advantageous to introduce point-mutations in any of the variants described herein.

Mutations with may suitably made include mutations in the following positions: H133, M15, M197, A209.

Cloning a DNA Sequence Encoding an Alpha-Amylase

The DNA sequence encoding a parent alpha-amylase may be isolated from any cell or microorganism producing the alpha-amylase in question, using various methods well known in the art. First, a genomic DNA and/or cDNA library should be constructed using chromosomal DNA or messenger RNA from the organism that produces the alpha-amylase to be studied. Then, if the amino acid sequence of the alpha-amylase is known, homologous, labelled oligonucleotide probes may be synthesized and used to identify alpha-amylase-encoding clones from a genomic library prepared from the organism in question. Alternatively, a labelled oligonucleotide probe containing sequences homologous to a known alpha-amylase gene could be used as a probe to identify alpha-amylase-encoding clones, using hybridization and washing conditions of lower stringency.

Yet another method for identifying alpha-amylase-encoding clones would involve inserting fragments of genomic DNA into an expression vector, such as a plasmid, transforming alpha-amylase-negative bacteria with the resulting genomic DNA library, and then plating the transformed bacteria onto agar containing a substrate for alpha-amylase, thereby allowing clones expressing the alpha-amylase to be identified.

Alternatively, the DNA sequence encoding the enzyme may be prepared synthetically by established standard methods, e.g. the phosphoroamidite method described by S. L. Beaucage and M. H. Caruthers (1981) or the method described by Matthes et al. (1984). In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. (1988).

Site-Directed Mutagenesis

Once an a-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the a-amylase-encoding sequence, is created in a vector carrying the a-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into a-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random Mutagenesis

Random mutagenesis is suitably performed either as localised or region-specific random mutagenesis in at least three parts of the gene translating to the amino acid sequence shown in question, or within the whole gene.

The random mutagenesis of a DNA sequence encoding a parent alpha-amylase may be conveniently performed by use of any method known in the art.

In relation to the above, a further aspect of the present invention relates to a method for generating a variant of a parent alpha-amylase, e.g. wherein the variant exhibits altered or increased thermal stability relative to the parent, the method comprising:

(a) subjecting a DNA sequence encoding the parent alpha-amylase to random mutagenesis, (b) expressing the mutated DNA sequence obtained in step (a) in a host cell, and (c) screening for host cells expressing analpha-amylase variant which has an altered property (i.e. thermal stability) relative to the parent alpha-amylase.

Step (a) of the above method of the invention is preferably performed using doped primers.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one which induces transitions, transversions, inversions, scrambling, deletions, and/or insertions.

Examples of a physical or chemical mutagenizing agent suitable for the present purpose include ultraviolet (UV) ir-radiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the alpha-amylase enzyme by any published technique, using e.g. PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints. The doping scheme may be made by using the DOPE program which, inter alia, ensures that introduction of stop codons is avoided.

When PCR-generated mutagenesis is used, either a chemically treated or non-treated gene encoding a parent alpha-amylase is subjected to PCR under conditions that increase the mis-incorporation of nucleotides (Deshler 1992; Leung et al., Technique, Vol. 1, 1989, pp. 11-15).

A mutator strain of *E. coli* (Fowler et al., Molec. Gen. Genet., 133, 1974, pp. 179-191), *S. cereviseae* or any other microbial organism may be used for the random mutagenesis of the DNA encoding the alpha-amylase by, e.g., transforming a plasmid containing the parent glycosylase into the mutator strain, growing the mutator strain with the plasmid and isolating the mutated plasmid from the mutator strain. The mutated plasmid may be subsequently transformed into the expression organism.

The DNA sequence to be mutagenized may be conveniently present in a genomic or cDNA library prepared from an organism expressing the parent alpha-amylase. Alternatively, the DNA sequence may be present on a suitable vector such as a plasmid or a bacteriophage, which as such may be incubated with or other-wise exposed to the mutagenising agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to performing the expression step b) or the screening step c). Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment.

Examples of suitable host cells are the following: gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus*; and gram-negative bacteria such as *E. coli*.

The mutated DNA sequence may further comprise a DNA sequence encoding functions permitting expression of the mutated DNA sequence.

Localized Random Mutagenesis

The random mutagenesis may be advantageously localized to a part of the parent alpha-amylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized, or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

Alternative Methods of Providing Alpha-Amylase Variants

Alternative methods for providing variants of the invention include gene shuffling method known in the art including the methods e.g. described in WO 95/22625 (from Affymax Technologies N. V.) and WO 96/00343 (from Novo Nordisk A/S).

Expression of Alpha-Amylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an alpha-amylase variant of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding an alpha-amylase variant of the invention, especially in a bacterial host, are the promoter of the lac operon of *E. coli*, the *Streptomyces coelicolor* agarase gene dagA promoters, the promoters of the

*Bacillus licheniformis* alpha-amylase gene (amyL), the promoters of the *Bacillus stearothermophilus* maltogenic amylase gene (amyM), the promoters of the *Bacillus amyloliquefaciens* alpha-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the alpha-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the *Bacillus* alpha-amylases mentioned herein comprise a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct of the invention encoding an alpha-amylase variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

The cell of the invention, either comprising a DNA construct or an expression vector of the invention as defined above, is advantageously used as a host cell in the recombinant production of an alpha-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a bacterial or a fungal (including yeast) cell.

Examples of suitable bacteria are grampositive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gram-negative bacteria such as *E. coli*. The transformation of the bacteria may, for instance, be effected by protoplast transformation or by using competent cells in a manner known per se.

The yeast organism may favourably be selected from a species of *Saccharomyces* or *Schizosaccharomyces*, e.g., *Saccharomyces cerevisiae*. The filamentous fungus may advantageously belong to a species of *Aspergillus*, e.g., *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells is described in EP 238 023.

In yet a further aspect, the present invention relates to a method of producing an alpha-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the alpha-amylase variant of the invention. Suitable media are available from commercial suppliers or may be prepared according to published recipes (e.g. as described in catalogues of the American Type Culture Collection).

The alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Compositions

In a still further aspect, the present invention relates to compositions comprising an alpha-amylase or alpha-amylase variant of the present invention. Preferably, the compositions are enriched in an alpha-amylase or alpha-amylase variant of the present invention. In the present context, the term "enriched" indicates that the alpha-amylase activity of the composition has been increased, e.g., with an enrichment factor of 1.1.

The composition may comprise an alpha-amylase or alpha-amylase variant of the invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be producible by means of a microorganism belonging to the genus *Aspergillus*, preferably *Aspergillus aculeatus, Aspergillus awamori, Aspergillus niger*, or *Aspergillus oryzae*, or *Trichoderma, Humicola*, preferably *Humicola insolens*, or *Fusarium*, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum.*

The alpha-amylase compositions may be prepared in accordance with methods known in the art and may be in the form of a liquid or a dry composition. For instance, the alpha-amylase composition may be in the form of a granulate or a microgranulate. The polypeptide to be included in the composition may be stabilized in accordance with methods known in the art.

Examples are given below of preferred uses of the alpha-amylase compositions of the invention. The dosage of the alpha-amylase composition of the invention and other conditions under which the composition is used may be determined on the basis of methods known in the art.

Further Compositions

The invention also relates to a composition comprising a mixture of one or more alpha-amylase or alpha-amylase variant of the invention derived from (as the parent Termamyl-like alpha-amylase) the *B. stearothermophilus* alpha-amylase having the sequence shown in SEQ ID NO: 3 and a Termamyl-like alpha-amylase derived from the *B. licheniformis* alpha-amylase having the sequence shown in SEQ ID NO: 4.

Further, the invention also relates to a composition comprising a mixture of one or more variants according the invention derived from (as the parent Termamyl-like alpha-amylase) the *B. stearothermophilus* alpha-amylase having the sequence shown in SEQ ID NO: 3 and a hybrid alpha-amylase comprising a part of the *B. amyloliquefaciens* alpha-amylase shown in SEQ ID NO: 5 and a part of the *B. licheniformis* alpha-amylase shown in SEQ ID NO: 4. The latter mentioned hybrid Termamyl-like alpha-amylase comprises the 445 C-terminal amino acid residues of the *B. licheniformis* alpha-amylase shown in SEQ ID NO: 4 and the 37 N-terminal amino acid residues of the α-amylase derived from *B. amyloliquefaciens* shown in SEQ ID NO: 5. Said latter mentioned hybrid alpha-amylase may suitably comprise the following mutations: H156Y+A181T+N190F+A209V+Q264S (using the numbering in SEQ ID NO: 4). In the examples below said hybrid parent Termamyl-like alpha-amylase, is used in combination with variants of the invention, which variants may be used in compositions of the invention.

In a specific embodiment of the invention the composition comprises a mixture of TVB146 and LE174, e.g., in a ratio of 2:1 to 1:2, such as 1:1.

An alpha-amylase or alpha-amylase variant of the invention or a composition of the invention may in an aspect of the invention be used for washing and/or dishwashing; for textile desizing or for starch liquefaction.

Detergent Compositions

The alpha-amylase or alpha-amylase variant of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase®, Savinase®, Primase®, Duralase®, Esperase®, and Kannase® (Novo Nordisk A/S), Maxatase®, Maxacal, Maxapem®, Properase®, Purafect®, Purafect OxP®, FN2®, and FN3® (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novo Nordisk A/S).

Amylases: Suitable amylases (alpha- and/or â-) include those of bacterial or fungal origin. Chemically modified or protein engineered mutants are included. Amylases include, for example, alpha-amylases obtained from *Bacillus*, e.g., a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novo Nordisk A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellu-lases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme®, and Carezyme® (Novo Nordisk A/S), Clazinase®, and Puradax HA® (Genencor International Inc.), and KAC-500 (B)® (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme® (Novo Nordisk A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated e.g, as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme pre-parations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, tripho-sphate, phosphonate, carbonate, citrate, nitrilotriacetic acid, ethylenediaminetetraacetic acid, diethylenetri-aminepen-taacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinyl-pyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers.

The detergent may contain a bleaching system which may comprise a H2O2 source such as perborate or percarbonate which may be combined with a peracid-forming bleach activator such as tetraacetylethylenediamine or nonanoyloxy-ben-zenesul-fonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202 which is hereby incorporated as reference.

Further Detergent Compositions

As mentioned above, variants of the invention may suitably be incorporated in detergent compositions. Increased thermostability at low calcium concentrations would be very beneficial for amylase performance in detergents, i.e., the alkaline region. Reference is made, for example, to WO 96/23874 and WO 97/07202 for further details concerning relevant ingredients of detergent compositions (such as laundry or dishwashing detergents), appropriate methods of formulating the variants in such detergent compositions, and for examples of relevant types of detergent compositions.

Detergent compositions comprising an alpha-amylase or alpha-amylase variant of the invention may additionally comprise one or more other enzymes, such as a lipase, cutinase, protease, cellulase, peroxidase or laccase, and/or another alpha-amylase.

An alpha-amylase or alpha-amylase variant of the invention may be incorporated in detergents at conventionally employed concentrations. It is at present contemplated that a variant of the invention may be incorporated in an amount corresponding to 0.00001-1 mg (calculated as pure, active enzyme protein) of alpha-amylase per liter of wash/dishwash liquor using conventional dosing levels of detergent.

Dishwash Detergent Compositions

The alpha-amylase or alpha-amylase variant of the invention may also be used in dishwash detergent compositions, including the following:

1) Powder Automatic Dishwashing Composition

| | |
|---|---|
| Nonionic surfactant | 0.4-2.5% |
| Sodium metasilicate | 0-20% |
| Sodium disilicate | 3-20% |
| Sodium triphosphate | 20-40% |
| Sodium carbonate | 0-20% |
| Sodium perborate | 2-9% |
| Tetraacetyl ethylene diamine (TAED) | 1-4% |
| Sodium sulphate | 5-33% |
| Enzymes | 0.0001-0.1% |

2) Powder Automatic Dishwashing Composition

| | |
|---|---|
| Nonionic surfactant (e.g. alcohol ethoxylate) | 1-2% |
| Sodium disilicate | 2-30% |
| Sodium carbonate | 10-50% |
| Sodium phosphonate | 0-5% |
| Trisodium citrate dihydrate | 9-30% |
| Nitrilotrisodium acetate (NTA) | 0-20% |
| Sodium perborate monohydrate | 5-10% |
| Tetraacetyl ethylene diamine (TAED) | 1-2% |
| Polyacrylate polymer (e.g. maleic acid/acrylic acid copolymer) | 6-25% |
| Enzymes | 0.0001-0.1% |
| Perfume | 0.1-0.5% |
| Water | 5-10 |

3) Powder Automatic Dishwashing Composition

| | |
|---|---|
| Nonionic surfactant | 0.5-2.0% |
| Sodium disilicate | 25-40% |
| Sodium citrate | 30-55% |
| Sodium carbonate | 0-29% |
| Sodium bicarbonate | 0-20% |
| Sodium perborate monohydrate | 0-15% |
| Tetraacetyl ethylene diamine (TAED) | 0-6% |
| Maleic acid/acrylic acid copolymer | 0-5% |
| Clay | 1-3% |
| Polyamino acids | 0-20% |
| Sodium polyacrylate | 0-8% |
| Enzymes | 0.0001-0.1% |

4) Powder Automatic Dishwashing Composition

| | |
|---|---|
| Nonionic surfactant | 1-2% |
| Zeolite MAP | 15-42% |
| Sodium disilicate | 30-34% |
| Sodium citrate | 0-12% |
| Sodium carbonate | 0-20% |
| Sodium perborate monohydrate | 7-15% |
| Tetraacetyl ethylene diamine (TAED) | 0-3% |
| Polymer | 0-4% |
| Maleic acid/acrylic acid copolymer | 0-5% |
| Organic phosphonate | 0-4% |
| Clay | 1-2% |
| Enzymes | 0.0001-0.1% |
| Sodium sulphate | Balance |

5) Powder Automatic Dishwashing Composition

| | |
|---|---|
| Nonionic surfactant | 1-7% |
| Sodium disilicate | 18-30% |
| Trisodium citrate | 10-24% |
| Sodium carbonate | 12-20% |
| Monopersulphate ($2KHSO_5 \cdot KHSO_4 \cdot K_2SO_4$) | 15-21% |
| Bleach stabilizer | 0.1-2% |
| Maleic acid/acrylic acid copolymer | 0-6% |
| Diethylene triamine pentaacetate, pentasodium salt | 0-2.5% |
| Enzymes | 0.0001-0.1% |
| Sodium sulphate, water | Balance |

6) Powder and Liquid Dishwashing Composition with Cleaning Surfactant System

| | |
|---|---|
| Nonionic surfactant | 0-1.5% |
| Octadecyl dimethylamine N-oxide dihydrate | 0-5% |
| 80:20 wt. C18/C16 blend of octadecyl dimethylamine N-oxide dihydrate and hexadecyldimethyl amine N-oxide dihydrate | 0-4% |
| 70:30 wt. C18/C16 blend of octadecyl bis (hydroxyethyl)amine N-oxide anhydrous and hexadecyl bis (hydroxyethyl)amine N-oxide anhydrous | 0-5% |
| $C_{13}$-$C_{15}$ alkyl ethoxysulfate with an average degree of ethoxylation of 3 | 0-10% |
| $C_{12}$-$C_{15}$ alkyl ethoxysulfate with an average degree of ethoxylation of 3 | 0-5% |
| $C_{13}$-$C_{15}$ ethoxylated alcohol with an average degree of ethoxylation of 12 | 0-5% |
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Citric acid | 0-29% |
| Sodium carbonate | 0-20% |
| Sodium perborate monohydrate | 0-11.5% |
| Tetraacetyl ethylene diamine (TAED) | 0-4% |
| Maleic acid/acrylic acid copolymer | 0-7.5% |
| Sodium sulphate | 0-12.5% |
| Enzymes | 0.0001-0.1% |

7) Non-Aqueous Liquid Automatic Dishwashing Composition

| | |
|---|---|
| Liquid nonionic surfactant (e.g. alcohol ethoxylates) | 2.0-10.0% |
| Alkali metal silicate | 3.0-15.0% |

-continued

| | |
|---|---|
| Alkali metal phosphate | 20.0-40.0% |
| Liquid carrier selected from higher glycols, polyglycols, polyoxides, glycolethers | 25.0-45.0% |
| Stabilizer (e.g. a partial ester of phosphoric acid and a $C_{16}$-$C_{18}$ alkanol) | 0.5-7.0% |
| Foam suppressor (e.g. silicone) | 0-1.5% |
| Enzymes | 0.0001-0.1% |

8) Non-Aqueous Liquid Dishwashing Composition

| | |
|---|---|
| Liquid nonionic surfactant (e.g. alcohol ethoxylates) | 2.0-10.0% |
| Sodium silicate | 3.0-15.0% |
| Alkali metal carbonate | 7.0-20.0% |
| Sodium citrate | 0.0-1.5% |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0.0-10.0% |
| Hydroxypropyl cellulose polymer | 0.0-0.6% |
| Enzymes | 0.0001-0.1% |
| Liquid carrier selected from higher lycols, polyglycols, polyoxides and glycol ethers | Balance |

9) Thixotropic Liquid Automatic Dishwashing Composition

| | |
|---|---|
| $C_{12}$-$C_{14}$ fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminium tristearate | 0-0.1% |
| Sodium cumene sulphonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulphonate | 0-4.0% |
| Monoethanol amine (MEA) | 0-1.86% |
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |

10) Liquid Automatic Dishwashing Composition

| | |
|---|---|
| Alcohol ethoxylate | 0-20% |
| Fatty acid ester sulphonate | 0-30% |
| Sodium dodecyl sulphate | 0-20% |
| Alkyl polyglycoside | 0-21% |
| Oleic acid | 0-10% |
| Sodium disilicate monohydrate | 18-33% |
| Sodium citrate dihydrate | 18-33% |
| Sodium stearate | 0-2.5% |
| Sodium perborate monohydrate | 0-13% |
| Tetraacetyl ethylene diamine (TAED) | 0-8% |
| Maleic acid/acrylic acid copolymer | 4-8% |
| Enzymes | 0.0001-0.1% |

11) Liquid Automatic Dishwashing Composition Containing Protected Bleach Particles

| | |
|---|---|
| Sodium silicate | 5-10% |
| Tetrapotassium pyrophosphate | 15-25% |
| Sodium triphosphate | 0-2% |
| Potassium carbonate | 4-8% |
| Protected bleach particles, e.g. chlorine | 5-10% |
| Polymeric thickener | 0.7-1.5% |
| Potassium hydroxide | 0-2% |
| Enzymes | 0.0001-0.1% |
| Water | Balance |

11) Automatic dishwashing compositions as described in 1), 2), 3), 4), 6) and 10), wherein perborate is replaced by percarbonate.

12) Automatic dishwashing compositions as described in 1)-6) which additionally contain a manganese catalyst. The manganese catalyst may, e.g., be one of the compounds described in "Efficient manganese catalysts for low-temperature bleaching", *Nature* 369, 1994, pp. 637-639.

Uses

The present invention is also directed to methods for using an alpha-amylase or alpha-amylase variant of the invention in detergents, in particular laundry detergent compositions and dishwash detergent compositions.

INDUSTRIAL APPLICATIONS

An alpha-amylase and alpha-amylase variant of the invention are well suited for use in a variety of industrial processes, in particular the enzymes of the invention finds potential applications as a component in detergents, e.g., laundry, dishwash and hard surface cleaning detergent compositions, but it may also be useful in the production of sweeteners and ethanol from starch. Thus, it may be used in conventional starch-converting processes, such as liquefaction and saccharification processes described in U.S. Pat. No. 3,912,590 and EP patent publications Nos. 252,730 and 63,909.

An alpha-amylase or alpha-amylase variant of the invention may also be used in the production of lignocellulosic materials, such as pulp, paper and cardboard, from starch reinforced waste paper and cardboard, especially where repulping occurs at pH above 7 and where amylases can facilitate the disintegration of the waste material through degradation of the reinforcing starch. The alpha-amylase of the invention is especially useful in a process for producing a papermaking pulp from starch-coated printed paper. The process may be performed as described in WO 95/14807, comprising the following steps:

a) disintegrating the paper to produce a pulp,
b) treating with a starch-degrading enzyme before, during or after step a), and
c) separating ink particles from the pulp after steps a) and b).

An alpha-amylase or alpha-amylase variant of the invention may also be very useful in modifying starch where enzymatically modified starch is used in papermaking together with alkaline fillers such as calcium carbonate, kaolin and clays. With the alkaline alpha-amylases of the invention it becomes possible to modify the starch in the presence of the filler thus allowing for a simpler integrated process.

An alpha-amylase or alpha-amylase variant of the invention may also be very useful in textile desizing. In the textile processing industry, alpha-amylases are traditionally used as auxiliaries in the desizing process to facilitate the removal of starch-containing size which has served as a protective coating on weft yarns during weaving. Complete removal of the size coating after weaving is import-ant to ensure optimum results in the subsequent processes, in which the fabric is scoured, bleached and dyed. Enzymatic starch break-down is preferred because it does not involve any harmful effect on the fiber material. In order to reduce processing cost and increase mill through-put, the desizing processing is sometimes combined with the scouring and bleaching steps. In such cases, non-enzymatic auxiliaries such as alkali or oxidation agents are typically used to break down the starch, because traditional a-amylases are not very compatible with high pH levels and bleaching agents. The non-enzymatic breakdown of the starch size does lead to some fiber damage because of the rather aggressive chemicals used. Accordingly, it would be desirable to use the alpha-amylases of the invention as they have an improved performance in alkaline solutions. The alpha-amylases may be used alone or in combination with a cellulase when desizing cellulose-containing fabric or textile.

The alpha-amylases of the invention may also be very useful in a beer-making process; the alpha-amylases will typically be added during the mashing process.

Production of Sweeteners from Starch

A "traditional" process for conversion of starch to fructose syrups normally consists of three consecutive enzymatic processes, viz., a liquefaction process followed by a saccharification process and an isomerization process. During the liquefaction process, starch is degraded to dextrins by an alpha-amylase (e.g., Termamyl™) at pH values between 5.5 and 6.2 and at temperatures of 95-160° C. for a period of approx. 2 hours. In order to ensure an optimal enzyme stability under these conditions, 1 mM of calcium is added (40 ppm free calcium ions).

After the liquefaction process the dextrins are converted into dextrose by addition of a glucoamylase (e.g. AMG™) and a debranching enzyme, such as an isoamylase or a pullulanase (e.g. Promozyme™). Before this step the pH is reduced to a value below 4.5, maintaining the high temperature (above 95° C.), and the liquefying alpha-amylase activity is denatured. The temperature is lowered to 60° C., and glucoamylase and debranching enzyme are added. The saccharification process proceeds for 24-72 hours.

After the saccharification process the pH is increased to a value in the range of 6-8, preferably pH 7.5, and the calcium is removed by ion exchange. The dextrose syrup is then converted into high fructose syrup using, e.g., an immobilized glucoseisomerase (such as Sweetzyme™).

At least 1 enzymatic improvements of this process could be envisaged. Reduction of the calcium dependency of the liquefying alpha-amylase. Addition of free calcium is required to ensure adequately high stability of the alpha-amylase, but free calcium strongly inhibits the activity of the glucoseisomerase and needs to be removed, by means of an expensive unit operation, to an extent which reduces the level of free calcium to below 3-5 ppm. Cost savings could be obtained if such an operation could be avoided and the liquefaction process could be performed without addition of free calcium ions.

To achieve that, a less calcium-dependent Termamyl-like alpha-amylase which is stable and highly active at low concentrations of free calcium (<40 ppm) is required. Such a Termamyl-like alpha-amylase should have a pH optimum at a pH in the range of 4.5-6.5, preferably in the range of 4.5-5.5.

Materials and Methods

Chemicals used as buffers and substrates were commercial products of at least reagent grade.

Enzymes:
SP690: alpha-amylase shown in SEQ ID NO: 1
SP722: alpha-amylase shown in SEQ ID NO: 2
Termamyl®: alpha-amylase from *Bacillus licheniformis* shown in SEQ ID NO: 4.

AA560: alpha-amylase of the invention shown in SEQ ID NO: 24 encoded by the DNA sequence shown in SEQ ID NO: 23.
AA360: alpha-amylase shown in SEQ ID NO: 26 being identical to the AA560 alpha-amylase encoded by the DNA sequence shown in SEQ ID NO: 25.
BSG alpha-amylase: *B. stearothermophilus* alpha-amylase depicted in SEQ ID NO: 3.
TVB146 alpha-amylase variant: *B. stearothermophilus* alpha-amylase variant depicted in SEQ ID NO: 3 with the following mutations: with the deletion in positions I181-G182+N193F.
LE174 hybrid alpha-amylase variant:
LE174 is a hybrid Termamyl-like alpha-amylase being identical to the Termamyl sequence, i.e., the *Bacillus licheniformis* alpha-amylase shown in SEQ ID NO: 4, except that the N-terminal 35 amino acid residues (of the mature protein) has been replaced by the N-terminal 33 residues of BAN (mature protein), i.e., the *Bacillus amyloliquefaciens* alpha-amylase shown in SEQ ID NO: 5, which further have the following mutations: H156Y+A181T+N190F+A209V+Q264S (using the numbering in SEQ ID NO: 4). LE174 was constructed by SOE-PCR (Higuchi et al. 1988, Nucleic Acids Research 16:7351).

Model Detergent:

A/P (Asia/Pacific) Model Detergent has the following composition: 20% STPP (sodium tripolyphosphate), 25% $Na_2SO_4$, 15% $Na_2CO_3$, 20% LAS (linear alkylbenzene sulfonate, Nansa 80S), 5% $C_{12}$-$C_{15}$ alcohol ethoxylate (Dobanol 25-7), 5% $Na_2Si_2O_5$, 0.3% NaCl.

Omo Multi Acao (Brazil),
Omo concentrated powder (Europe) (product of Unilever)
Ariel Futur liquid (Europe) (product of Procter and Gamble)

Deposit of Biological Material

The following biological material has been deposited under the terms of the Budapest Treaty with the Deutshe Sammmlung von Microorganismen und Zellkulturen GmbH (DSMZ), Mascheroder Weg 1b, D-38124 Braunschweig DE, and given the following accession number:

| Deposit | Accession Number | Date of Deposit |
|---------|-----------------|-----------------|
| NN017557 | DSM 12648 | 25 Jan. 1999 |
| NN017560 | DSM 12649 | 25 Jan. 1999 |
| NN049467 | DSM12761 | $7^{th}$ April 1999 |
| NN049470 | DSM12764 | $7^{th}$ April 1999 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

Host Organism

*Bacillus subtilis* strain SHa273 is disclosed in WO 95/10603
*E. coli* strain SJ2 (Diderichsen et al. (1990)).
Plasmids: The gene bank vector pSJ1678 is disclosed in WO 94/19454 which is hereby incorporated by reference. Error! Bookmark not defined.

pTVB110 is a plasmid replicating in *Bacillus subtilis* by the use of origin of replication from pUB110 (Gryczan, T. J. (1978) J. Bact. 134:318-329). The plasmid further encodes the cat gene, conferring resistance towards chlorampenicol, obtained from plasmid pC194 (Horinouchi, S, and Weisblum, B. (1982), J. Bact. 150: 815-825). The plasmid harbors a truncated version of the *Bacillus licheniformis* alpha-amylase gene, amyL, such that the amyL promoter, signal sequence and transcription terminator are present, but the plasmid does not provide an amy-plus phenotype (halo formation on starch containing agar).

Methods

General Molecular Biology Methods:

Unless otherwise mentioned the DNA manipulations and transformations were performed using standard methods of molecular biology (Sambrook et al. (1989); Ausubel et al. (1995); Harwood and Cutting (1990).

Fermentation and Purification of Alpha-Amylase Variants

Fermentation may be performed by methods well known in the art or as follows.

A *B. subtilis* strain harbouring the relevant expression plasmid is streaked on a LB-agar plate with 10 ìg/ml kanamycin from −80° C. stock, and grown overnight at 37° C.

The colonies are transferred to 100 ml BPX media supplemented with 10 ìg/ml kanamycin in a 500 ml shaking flask.

Composition of BPX Medium:

| | |
|---|---|
| Potato starch | 100 g/l |
| Barley flour | 50 g/l |
| BAN 5000 SKB | 0.1 g/l |
| Sodium caseinate | 10 g/l |
| Soy Bean Meal | 20 g/l |
| Na$_2$HPO$_4$,12H$_2$O | 9 g/l |
| Pluronic ™ | 0.1 g/l |

The culture is shaken at 37° C. at 270 rpm for 5 days.

Cells and cell debris are removed from the fermentation broth by centrifugation at 4500 rpm in 20-25 minutes. Afterwards the supernatant is filtered to obtain a completely clear solution. The filtrate is concentrated and washed on a UF-filter (10000 cut off membrane) and the buffer is changed to 20 mM Acetate pH 5.5. The UF-filtrate is applied on a S-sepharose F. F. and elution is carried out by step elution with 0.2M NaCl in the same buffer. The eluate is dialysed against 10 mM Tris, pH 9.0 and applied on a Q-sepharose F. F. and eluted with a linear gradient from 0-0.3M NaCl over 6 column volumes. The fractions which contain the activity (measured by the Phadebas assay) are pooled, pH was adjusted to pH 7.5 and remaining color was removed by a treatment with 0.5% W/vol. active coal in 5 minutes.

Assays for Determining Alpha-Amylase Activity

Activity determination—(KNU) Error! Bookmark not defined.

One Kilo alpha-amylase Unit (1 KNU) is the amount of enzyme which breaks down 5.26 g starch (Merck, Amylum Solubile, Erg. B 6, Batch 9947275) per hour in Novo Nordisk's standard method for determination of alpha-amylase based upon the following condition:

| | |
|---|---|
| Substrate | soluble starch |
| Calcium content in solvent | 0.0043 M |
| Reaction time | 7-20 minutes |
| Temperature | 37° C. |
| pH | 5.6 |

Detailed description of Novo Nordisk's analytical method (AF 9) is available on request.

BS-Amylase Activity Determination—KNU(S)

1. Application Field

This method is used to determine alpha-amylase activity in fermentation and recovery samples and formulated and granulated products.

2. Principle

BS-amylase breaks down the substrate (4,6-ethylidene (G$_7$)-p-nitrophenyl(G$_1$)-alpha,D-maltoheptaoside (written as ethylidene-G$_7$-PNP) into, among other things, G$_2$-PNP and G$_3$-PNP, where G denoted glucose and PNP p-nitrophenol.

G2-PNP and G3-PNP are broken down by alpha-glucosidase, which is added in excess, into glucose and the yellow-coloured p-nitrophenol.

The colour reaction is monitored in situ and the change in absorbance over time calculated as an expression of the spread of the reaction and thus of the activity of the enzyme. See the Boehringer Mannheim 1442 309 guidelines for further details.

2.1 Reaction Conditions

Reaction:

| | |
|---|---|
| Temperature: | 37° C. |
| pH: | 7.1 |
| Pre-incubation time: | 2 minutes |

Detection:

| | |
|---|---|
| Wavelength: | 405 nm |
| Measurement time | 3 minutes |

3. Definition of Units

*Bacillus stearothermophius* alpha-amylase (BS-amylase) activity is determined relative to a standard of declared activity and stated in Kilo Novo Units (Stearothermophilus) or KNU(S)).

4. Specificity and Sensitivity

| | |
|---|---|
| Limit of determination: | approx. 0.4 KNU(s)/g |

5. Apparatus

Cobas Fara analyser

Diluted (e.g. Hamilton Microlab 1000)

Analytical balance (e.g. Mettler AE 100)

Stirrer plates

6. Reagents/Substrates

A ready-made kit is used in this analysis to determine alpha-amylase activity. Note that the reagents specified for the substrate and alpha-glucosidase are not used as described in the Boehringer Mannheim guidelines. However, the designations "buffer", "glass 1", glass 1a" and Glass 2" are those referred to in those guidelines.

6.1. Substrate 4,6-ethylidene(G$_7$)-p-nitrophenyl(G$_1$)-alpha,D-maltoheptaoside (written as ethylidene-G$_7$-PNP) e.g. Boehringer Mannheim 1442 309

6.2 Alpha-Glucosidase Help Reagent alpha-glucosidase, e.g. Boehringer Mannheim 1442 309

6.3 BRIJ 35 Solution

| | |
|---|---|
| BRIJ 35 (30% W/V Sigma 430 AG-6) | 1000 mL |
| Demineralized water | up to 2,000 mL |

6.4 Stabiliser

| | |
|---|---|
| Brij 35 solution | 33 mL |
| $CaCl_2 \cdot 2H_2O$ (Merck 2382) | 882 g |
| Demineralized water | up to 2,000 mL |

7. Samples and Standards
7.1 Standard Curve

Example: Preparation of Bs-Amylase Standard Curve

The relevant standard is diluted to 0.60 KNU(s)/mL as follows. A calculated quantity of standard is weighed out and added to 200 mL volumetric flask, which is filled to around the ⅔ mark with demineralized water. Stabiliser corresponding to 1% of the volume of the flask is added and the flask is filled to the mark with demineralized water.

A Hamilton Microlab 1000 is used to produce the dilutions shown below. Demineralized water with 1% stabiliser is used as the diluent.

| Dilution No. | Enzyme stock solution | 1% stabiliser | KNU(s)/mL |
|---|---|---|---|
| 1 | 20iL | 580iL | 0.02 |
| 2 | 30iL | 570iL | 0.03 |
| 3 | 40iL | 560iL | 0.04 |
| 4 | 50iL | 550iL | 0.05 |
| 5 | 60iL | 540iL | 0.06 |

7.2 Level Control

A Novo Nordisk A/S BS amylase level control is included in all runs using the Cobas Fara. The control is diluted with 1% stabiliser so that the final dilution is within the range of the standard curve. All weights and dilutions are noted on the worklist

7.3 Sample Solutions

Single Determination

Fermentation samples (not final samples) from production, all fermentation samples from pilot plants and storage stability samples are weighed out and analyzed once only.

Double Determination Over 1 Run:

Process samples, final fermentation samples from production, samples from GLP studies and R&D samples are weighed out and analyzed twice.

Double Determinations Over 2 Runs:

Finished product samples are weighed out and analyzed twice over two separate runs. Maximum concentration of samples in powder form: 5%

Test samples are diluted with demineralized water with 1% stabiliser to approx. 0.037 KNU(S)/mL on the basis of their expected activity. The final dilution is made direct into the sample cup.

8. Procedure
8.1 Cobas Menu Program

The Cobas Menu Program is used to suggest the weight/dilutions of samples and level control to be used.

The samples are entered into the program with a unique identification code and a worklist is printed out The samples and control are weighed out and diluted as stated on the worklist with hand-written weight data is inserted into the BS-amylase analysis logbook The results are computed automatically by the Cobas Fara as described in item 9 and printed out along with the standard curve.

Worklists and results printouts are inserted into the BS-amylase analysis logbook.

8.2 Cobas Fara Set-Up

The samples are placed in the sample rack

The five standards are placed in the calibration rack at position 1 to 5 (strongest standard at position 5), and control placed in the same rack at position 10.

The substrate is transferred to a 30 mL reagent container and placed in that reagent rack at position 2 (holder 1).

The alpha-glucosidase help reagent is transferred to a 50 mL reagent container and placed in the reagent rack at position 2 (holder C)

8.3 Cobas Fare Analysis

The main principles of the analysis are as follows:

20 iL sample and 10 iL rinse-water are pipetted into the cuvette along with 250iL alpha-glucosidase help reagent. The cuvette rotates for 10 seconds and the reagents are thrown out into the horizontal cuvettes. 25 iL substrate and 20iL rinse-water are pipetted off. After a 1 second wait to ensure that the temperature is 37° C., the cuvette rotates again and the substrate is mixed into the horizontal cuvettes. Absorbance is measured for the first time after 120 seconds and then every 5 seconds. Absorbance is measured a total of 37 times for each sample.

9. Calculations

The activity of the samples is calculated relative to Novo Nordisk A/S standard.

The standard curve is plotted by the analyzer. The curve is to be gently curved, rising steadily to an absorbance of around 0.25 for standard no. 5.

The activity of the samples in KNU(S)/mL is read off the standard curve by the analyzer.

The final calculations to allow for the weights/dilutions used employ the following formula:

$$\text{Activity in KNU}(S)/g = S \times V \times F/W$$

S=analysis result read off (KNU(S)/mL
V=volume of volumetric flask used in mL
F=dilution factor for second dilution
W=weight of enzyme sample in g

9.2 Calculation of Mean Values

Results are stated with 3 significant digits. However, for sample activity<10 KNU(S)/g, only 2 significant digits are given.

The following rules apply on calculation of mean values:
1. Data which deviates more than 2 standard deviations from the mean value is not included in the calculation.
2. Single and double determination over one run:
The mean value is calculated on basis of results lying within the standard curve's activity area.
3. Double determinations over two runs: All values are included in the mean value. Outliers are omitted.

10. Accuracy and Precision

The coefficient of variation is 2.9% based on retrospective validation of analysis results for a number of finished products and the level control.

Phadebas Assay (for Alpha-Amylase Activity Determination)
alpha-amylase activity is determined by a method employing Phadebas® tablets as substrate. Phadebas tablets (Phadebas® Amylase Test, supplied by Pharmacia Diagnostic) contain a cross-linked insoluble blue-colored starch polymer which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given alpha-amylase will hydrolyze a certain amount of substrate and a blue colour will be produced. The colour intensity is measured at 620 nm. The measured absorbance is directly proportional to the specific activity (activity/mg of pure alpha-amylase protein) of the alpha-amylase in question under the given set of conditions.

Alternative Alpha-Amylase Activity Method (PNP-G7 Assay)

alpha-amylase activity is determined by a method employing the PNP-G7 substrate. PNP-G7 which is a abbreviation for p-nitrophenyl-alpha,D-maltoheptaoside is a blocked oligosaccharide which can be cleaved by an endo-amylase. Following the cleavage, the alpha-Glucosidase included in the kit digest the substrate to liberate a free PNP molecule which has a yellow colour and thus can be measured by visible spectophometry at ë=405 nm. (400-420 nm.). Kits containing PNP-G7 substrate and alpha-Glucosidase is manufactured by Boehringer-Mannheim (cat. No. 1054635).

To prepare the substrate one bottle of substrate (BM 1442309) is added to 5 ml buffer (BM1442309). To prepare the alpha-Glucosidase one bottle of alpha-Glucosidase (BM 1462309) is added to 45 ml buffer (BM1442309). The working solution is made by mixing 5 ml alpha-Glucosidase solution with 0.5 ml substrate.

The assay is performed by transforming 20 µl enzyme solution to a 96 well microtitre plate and incubating at 25° C. 200 µl working solution, 25° C. is added. The solution is mixed and pre-incubated 1 minute and absorption is measured every 15 sec. over 3 minutes at OD 405 nm.

The slope of the time dependent absorption-curve is directly proportional to the specific activity (activity per mg enzyme) of the alpha-amylase in question under the given set of conditions.

EXAMPLES

Example 1

Construction of Variants of BSG Alpha-Amylase (SEQ ID NO: 3)

The gene encoding BSG, amyS, is located in plasmid pPL1117. This plasmid contains also the gene conferring resistance towards kanamycin and an origin of replication, both obtained from plasmid pUB110 (Gryczan, T. J. et al (1978) J. Bact 134:318-329).

The DNA sequence of the mature part of amyS is shown as SEQ ID NO: 11 and the amino acid sequence of the mature protein is shown as SEQ ID NO: 3

BSG variant TVB145, which contains a deletion of 6 nucleotides corresponding to amino acids I181-G182 in the mature protein, is constructed as follows:

Polymerase Chain Reaction (PCR) is utilized to amplify the part of the amyS gene (from plasmid pPL1117), located between DNA primers BSG1 (SEQ ID NO: 16) and BSGM2 (SEQ ID NO: 19). BSG1 is identical to a part of the amyS gene whereas BSGM2 contains the 6 bp nucleotide deletion. A standard PCR reaction is carried out: 94° C. for 5 minutes, 25 cycles of (94° C. for 45 seconds, 50° C. for 45 seconds, 72° C. for 90 seconds), 72° C. for 7 minutes using the Pwo polymerase under conditions as recommended by the manufacturer, Boehringer Mannheim Gmbh.

The resulting approximately 550 bp amplified band was used as a megaprimer (Barik, S and Galinski, M S (1991): Biotechniques 10: 489-490) together with primer BSG3 in a second PCR with pPL1117 as template resulting in a DNA fragment of approximately 1080 bp.

This DNA fragment is digested with restriction endonucleases Acc651 and SalI and the resulting approximately 550 bp fragment is ligated into plasmid pPL1117 digested with the same enzymes and transformed into the protease- and amylase-deleted Bacillus subtilis strain SHA273 (described in WO 92/11357 and WO 95/10603).

Kanamycin resistant and starch degrading transformants were analysed for the presence of the desired mutations (restriction digest to verify the introduction of a HindIII site in the gene). The DNA sequence between restriction sites Acc651 and SalI was verified by DNA sequencing to ensure the presence of only the desired mutations.

BSG variant TVB146 which contains the same 6 nucleotide deletion as TVB145 and an additional substitution of asparagine 193 for a phenylalanine, N193F, was constructed in a similar way as TVB145 utilizing primer BSGM3 (SEQ ID NO: 20) in the first PCR.

BSG variant TVB161, containing the deletion of I181-G182, N193F, and L204F, is constructed in a similar way as the two previous variants except that the template for the PCR reactions is plasmid pTVB146 (pPL1117 containing the TVB146-mutations within amyS and the mutagenic oligonucleotide for the first PCR is BSGM3.

BSG variant TVB162, containing the deletion of I181-G182, N193F, and E210H, is constructed in a similar way as TVB161 except that the mutagenic oligonucleotide is BSGM4 (SEQ ID NO: 21).

BSG variant TVB163, containing the deletion of I181-G182, N193F, and E214Q, is constructed in a similar way as TVB161 except that the mutagenic oligonucleotide is BSGM5 (SEQ ID NO: 22).

The above constructed BSG variants were then fermented and purified as described above in the "Material and Methods" section.

Example 2

Measurement of the Calcium- and pH-Dependent Stability

Normally, the industrial liquefaction process runs using pH 6.0-6.2 as liquefaction pH and an addition of 40 ppm free calcium in order to improve the stability at 95° C.-105° C. Some of the herein proposed substitutions have been made in order to improve the stability at
1. lower pH than pH 6.2 and/or
2. at free calcium levels lower than 40 ppm free calcium.

Two different methods have been used to measure the improvements in stability obtained by the different substitutions in the alpha-amylase from *B. stearothermophilus*:

Method 1. One assay which measures the stability at reduced pH, pH 5.0, in the presence of 5 ppm free calcium. 10 ig of the variant were incubated under the following conditions: A 0.1 M acetate solution, pH adjusted to pH 5.0, containing 5 ppm calcium and 5% w/w common corn starch (free of calcium). Incubation was made in a water bath at 95° C. for 30 minutes.

Method 2. One assay which measure the stability in the absence of free calcium and where the pH is maintained at pH 6.0. This assay measures the decrease in calcium sensitivity: 10 ig of the variant were incubated under the following conditions: A 0.1 M acetate solution, pH adjusted to pH 6.0, containing 5% w/w common corn starch (free of calcium). Incubation was made in a water bath at 95° C. for 30 minutes.

Stability Determination

All the stability trials 1, 2 have been made using the same set up. The method was:

The enzyme was incubated under the relevant conditions (1-4). Samples were taken at 0, 5, 10, 15 and 30 minutes and diluted 25 times (same dilution for all taken samples) in assay buffer (0.1M 50 mM Britton buffer pH 7.3) and the activity was measured using the Phadebas assay (Pharmacia) under standard conditions pH 7.3, 37° C.

The activity measured before incubation (0 minutes) was used as reference (100%). The decline in percent was calculated as a function of the incubation time. The table shows the residual activity after 30 minutes of incubation.

Stability Method 1./Low pH Stability Improvement

| MINUTES OF INCUBATION | WT. SEQ. ID. NO: 3 AMYLASE (BSG) | SEQ. ID NO: 3 VARIANT WITH DELETION IN POS. I181-G182 (TVB145) | SEQ. ID NO: 3 VARIANT WITH DELETION IN POS. I181-G182 + N193F (TVB146) | SEQ. ID NO: 3 VARIANT WITH DELETION IN POS. I181-G182 + N193F + E214Q (TVB163) |
|---|---|---|---|---|
| 0 | 100 | 100 | 100 | 100 |
| 5 | 29 | 71 | 83 | 77 |
| 10 | 9 | 62 | 77 | 70 |
| 15 | 3 | 50 | 72 | 67 |
| 30 | 1 | 33 | 62 | 60 |

Stability Method 1./Low pH Stability Improvement

The temperature described in method 1 has been reduced from 95° C. to 70° C. since the amylases mentioned for SEQ ID NO: 1 and 2 have a lower thermostability than the one for SEQ ID NO: 3.

| MINUTES OF INCUBATION | WT. SEQ. ID. NO: 2 AMYLASE | SEQ. ID NO: 2 VARIANT WITH DELETION IN POS. D183-G184 | SEQ. ID NO: 1 AMYLASE | SEQ. ID NO: 1 VARIANT WITH DELETION IN POS. T183-G184 |
|---|---|---|---|---|
| 0 | 100 | 100 | 100 | 100 |
| 5 | 73 | 92 | 41 | 76 |
| 10 | 59 | 88 | 19 | 69 |
| 15 | 48 | 91 | 11 | 62 |
| 30 | 28 | 92 | 3 | 59 |

Stability Method 2./Low Calcium Sensitivity

| MINUTES OF INCUBATION | WT. SEQ ID NO: 3 AMYLASE (BSG) | SEQ ID NO: 3 VARIANT WITH DELETION IN POS. I181-G182 (TVB145) | SEQ ID NO: 3 VARIANT WITH DELETION IN POS. I181-G182 + N193F (TVB146) | SEQ ID NO: 3 VARIANT WITH DELETION IN POS. I181-G182 + N193F + E214Q (TVB163) |
|---|---|---|---|---|
| 0 | 100 | 100 | 100 | 100 |
| 5 | 60 | 82 | 81 | 82 |
| 10 | 42 | 76 | 80 | 83 |
| 15 | 31 | 77 | 81 | 79 |
| 30 | 15 | 67 | 78 | 79 |

Specific Activity Determination.

The specific activity was determined using the Phadebas assay (Pharmacia) as activity/mg enzyme. The activity was determined using the alpha-amylase assay described in the Materials and Methods section herein.

The specific activity of the parent enzyme and a single and a double mutation was determined to:

| | |
|---|---|
| BSG: SEQ ID NO: 3 (Parent enzyme) | 20000 NU/mg |
| TVB145: SEQ ID NO: 3 with the deletion in positions I181-G182: (Single mutation) | 34600 NU/mg |
| TVB146: SEQ ID NO: 3 with the deletion in positions I181-G182 + N193F: (Double mutation) | 36600 NU/mg |
| TVB163: SEQ ID NO: 3 with the deletion in positions I181-G182 + N193F + E214Q: (Triple mutation) | 36300 NU/mg |

Example 3

Pilot Plant Jet Cook and Liquefaction with Alpha-Amylase Variant TVB146

Pilot plant liquefaction experiments were run in the mini-jet system using a dosage of 50 NU (S)/g DS at pH 5.5 with 5 ppm added $Ca^{++}$, to compare the performance of formulated BSG alpha-amylase variant TVB146 (SEQ ID NO: 3 with deletion in positions I181-G182+N193F) with that of parent BSG alpha-amylase (SEQ ID NO: 3). The reaction was monitored by measuring the DE increase (Neocuproine method) as a function of time.

Corn starch slurries were prepared by suspending 11.8 kg Cerestar C*Pharm GL 03406 (89% starch) in deionized water and making up to 30 kg. The pH was adjusted to 5.5 at ambient temperature, after the addition of 0.55 g $CaCl_2 \cdot 2H_2O$.

The following enzymes were used:

| | |
|---|---|
| TVB146 | 108 KNU(S)/g, 146 KNU(SM9)/g |
| BSG amylase | 101 KNU(S)/g, 98 KNU(SM9)/g |

An amount of enzyme corresponding to 50 NU (SM9)/g DS was added, and the conductivity adjusted to 300 mS using NaCl. The standard conditions were as follows:

| | |
|---|---|
| Substrate concentration | 35% w/w (initial) |
| | 31.6-31.9% w/w (final) |
| Temperature | 105° C., 5 minutes (Primary liquefaction) |
| | 95° C., 90 minutes (Secondary liquefaction) |
| pH (initial) | 5.5 |

After jetting, the liquefied starch was collected and transported in sealed thermos-flasks from the pilot plant to the laboratory, where secondary liquefaction was continued at 95° C.

10 ml samples were taken at 15 minute intervals from 15-90 minutes. 2 drops of 1 N HCl were added to inactivate the enzyme. From these samples, 0.3-0.1 g (according to the expected DE) were weighed out and diluted to 100 ml. Reducing sugars were then determined according to the Neocuproine method (Determination of reducing sugar with improved precision. Dygert, Li, Florida and Thomas (1965). Anal. Biochem 13, 368) and DE values determined. The development of DE as a function of time is given in the following table:

| Time (min.) | TVB146 | BSG |
|---|---|---|
| | DE (neocuproine) | |
| 15 | 2.80 | 2.32 |
| 30 | 4.88 | 3.56 |
| 45 | 6.58 | 4.98 |
| 60 | 8.17 | 6.00 |
| 75 | 9.91 | 7.40 |
| 90 | 11.23 | 8.03 |

As can be seen the alpha-amylase variant TVB146 performed significantly better under industrially relevant application conditions at low levels of calcium than the parent BSG alpha-amylase.

Example 4

Jet Cook and Liquefaction with a Combination of Alpha-Amylase Variants (TVB146 and LE174)

Jet cook and liquefaction using a combination of the alpha-amylase variants, TVB146 and LE174 (ratio 1:1) were carried out at the following conditions:
Substrate A.E. Staley food grade powdered corn starch (100 lbs)
D.S. 35% using DI water
Free $Ca^2$+2.7 ppm at pH 5.3 (none added, from the starch only)
Initial pH 5.3
Dose AF9 units (AF9 is available on request) for each enzyme variant was 28 NU/g starch db for a total dose of 56 NU/g
Temperature in primary liquefaction 105° C.
Hold time in primary liquefaction 5 minutes
Temperature in secondary liquefaction 95° C.

At 15 minutes into secondary liquefaction 1.5 gms of hydrolyzate was added to a tared one liter volumetric containing 500 cc of DI water and 1 ml of one normal HCl and the exact wt. added was recorded. This was repeated at 15 minute intervals out to 90 minutes with an additional point at 127 minutes. These were diluted to one liter and determined for dextrose equivalence via Neocuproine method as described by Dygert, Li, Florida and Thomas. Determination of reducing sugar with improved precision (1965). Anal. Biochem 13, 368.

The results were as follows:

| Time | DE |
|---|---|
| 15 | 3.2 |
| 30 | 4.8 |
| 45 | 6.3 |
| 60 | 7.8 |
| 75 | 9.4 |
| 90 | 10.4 |
| 127 | 13.1 |

Example 5

Isolation of Genomic DNA from DSM 12648 and DSM 12649

The strains *Bacillus* sp. DSM 12649 (the AA560 alpha-amylase) and *Bacillus* sp. DSM 12648 (the AA349 alpha-amylase) were propagated in liquid TY medium (as described in Ausubel et al. (1995)). After 16 hours incubation at 37° C.

and 300 rpm, the cells were harvested, and genomic DNA isolated by the method described by Pitcher et al. (1989).

Genomic Library Construction

Genomic DNA of strain DSM 12649 was partially digested with restriction enzyme Sau3A, and size-fractionated by electrophoresis on a 0.7% agarose gel. Fragments between 2 and 10 kb in size was isolated by electrophoresis onto DEAE-cellulose paper (Dretzen et al. (1981).

Isolated DNA fragments were ligated to BamHI digested pSJ1678 plasmid DNA, and the ligation mixture was used to transform *E. coli* SJ2.

Transformation

*E. coli* SJ2 host cells were prepared for and transformed by electroporation using a gene PULSER™ electroporator from BIO-RAD as described by the supplier.

Identification of Positive Transformant:

A DNA library in *E. coli* SJ2, constructed as described above, was screened on LB agar plates (described in Ausbel et al. (1995)) containing 0.5% AZCL-amylose (Megazyme) and 10 ig/ml Chloramphenicol and incubated overnight at 37° C. Clones expressing amylase activity appeared with blue diffusion haloes. One such clone was named LiH1274. The DNA was further characterized by DNA sequencing of part of the cloned Sau3A DNA fragment.

Example 6

Determination of the DNA Sequence of the Gene Encoding Alpha-Amylase from Strain DSM 12648 (AA349)

The clone constituting a large chromosomal fragment containing the gene encoding the amylolytic activity inserted into plasmid pSJ1678, pLiH1247, was used as template to specifically PCR amplify internal DNA fragments of the alpha-amylase encoding gene by the use of degenerate primers directed towards the conserved regions in known *Bacillus* alpha-amylases.

The degenerate primers were directed towards the following regions/amino acid sequences:

```
For36:   GITA(L/V/I)W(I/L)          (SEQ ID NO: 27)

For97:   VY(G/A)D(V/F/L)V(M/L/I/F)NH (SEQ ID NO: 28)

For227:  DG(F/I)R(F/L/I/V)DA(A/V)KH  (SEQ ID NO: 29)

Rev235:  DG(F/I)R(F/L/I/V)DA(A/V)KH  (SEQ ID NO: 30)

Rev328:  VTFV(D/E)NHD               (SEQ ID NO: 31)

Rev410:  GWTREG                     (SEQ ID NO: 32)
```

The various combinations of forward (For) and reverse (Rev) primers were used in PCR and internal DNA fragments could be amplified.

The DNA fragments were purified by QIAquick spin columns (QUIGEN) and sequenced utilizing the same degenerate primers.

From sequence the DNA sequence (SEQ ID NO: 23) of the complete coding region encoding the mature AA349 alpha-amylase (SEQ ID NO: 26) was determined by a standard primers-walking approach.

Example 7

Determination of the DNA Sequence of the Gene Encoding Alpha Amylase from Strain DSM 12649 (AA560)

A preparation of chromosomal DNA from strain DSM 12649 was utilized as template in a similar experiment to the one described above in Example 7 in order to determine the DNA sequence of the AA560 alpha-amylase (SEQ ID NO: 24).

Example 8

Subcloning of the AA349 Alpha-Amylase into pTVB110 pTVB110 is a plasmid replicating in *Bacillus subtilis* by the use of origin of replication from pUB110 (Gryczan, T. J. (1978) J. Bact. 134:318-329). The plasmid further encodes the cat gene, conferring resistance towards chlorampenicol, obtained from plasmid pC194 (Horinouchi, S. and Weisblum, B. (1982), J. Bact. 150: 815-825). The plasmid harbors a truncated version of the *Bacillus licheniformis* alpha-amylase gene, amyL, such that the amyL promoter, signal sequence and transcription terminator are present, but the plasmid does not provide an amy-plus phenotype (halo formation on starch containing agar).

In order to express high amount of the AA349 alpha-amylase the mature gene was fused precisely to the amyL signal sequence so that transcription is initiated by the amyL promoter and translocation is directed by the amyL signal sequence.

A PstI site is found within the mature AA349 alpha-amylase. Since the cloning of the gene into pTVB110 would utilize the PstI site in pTVB110, the PstI site located within the AA349 alpha-amylase gene was destroyed during the cloning (by introduction of a silent mutation for amino acid Alanine 88 (GCA to GCG).

Primers 188cloningN and 188(Pst-) were used to amplify an approximately 280 bp fragment by PCR on plasmid pLiH1247 using the Pwo polymerase under conditions recommended by the manufacturer (Boehringer Mannheim). This fragment was purified from agarose gel and used as a megaprimer (G. Sarkar and S. S. Sommer (1990) Biotechniques 8: 404-407) together with primer 188cloningC to amplify the full length gene encoding the mature amylase in a second PCR.

The resulting approximately 1480 bp fragment was digested with restriction endonucleases PstI and SfiI and ligated with plasmid pTVB110 digested with the same enzymes.

Protease and amylase deleted *Bacillus subtilis* strain SHa273 (mentioned in WO 95/10603) was transformed with the ligation mixture and the DNA sequence of an amy-plus transformant was verified. This plasmid is denoted pTVB231.

Oligonucleotides:

```
188(Pst-):
                                        (SEQ ID NO: 33)
5' GGC GTT AAC CGC AGC TTG TAA C

188cloningC:
                                        (SEQ ID NO: 34)
5' CCG AGC TCG GCC GGC TGG GCC GTC GAC TTA TTT
GTT TAC CCA AAT AGA AAC 188cloningN:
                                        (SEQ ID NO: 35)
5' CAT TCT GCA GCA GCG GCG CAC CAT AAT GGT ACG
AAC G
```

Example 9

Subcloning of the AA560 Alpha-Amylase into pTVB110

DNA sequencing revealed a high DNA identity between alpha-amylases from stains DSM12648 (AA349) and DSM 12649 (AA560). Consequently the same oligonucleotides and strategy was utilized for the cloning of AA560 alpha-amylase into expression vector pTVB110 resulting in plasmid pTVB232, which was then fermented using standard techniques.

Example 10

Purification of the AA560 Alpha-Amylase

The culture broth was flocculated by adding 0.01 ml 50% (w/w) $CaCl_2$, $2H_2O$, 0.0125 ml 12% (w/w) Sodium aluminate, 0.025 ml 10% C521 and 0.075 ml 0.1% A130 pr. ml culture broth. A clear solution was obtained after centrifugation. The enzyme solution was added ammonium sulphate to a final concentration of 1.2 M and applied on a Butyl Toyo Pearl column (100 ml) previously equilibrated in 1.2 M ammonium sulphate, 10 mM Tris-HCl, pH 7.0. The amylase was eluted using 5 mM Tris-HCl, pH 7.0 and the eluted pool was dialysed against 5 mM Tris-HCl over night. The fraction was then subjected to ion exchange chromatography using a Q-Sepharose column (200 ml) previously equilibrated in 20 mM Tris-HCl, pH 9.0. Unbound material was washed out with the equilibration buffer, and the amylase was eluted using a linear gradient 0-1 M NaCl, 20 mM Tris-HCl, pH 9.0. Purity of the amylase preparation was above 95% judged by SDS-PAGE.

Example 11

Characterization of the AA560 Alpha-Amylase

The alpha-amylase activity was measured using both the Phadebas assay (37° C., pH 7.3) and the Alternative pNPG7 Assay (25° C., pH 7.1) described above. pH- and temperature profiles were made at selected pH- and temperature values. The pH-profile was measured at 37° C. and the temperature profile was measured at pH 9.0

Isoelectric Point was determined using isoelectric focusing (Pharmacia, Ampholine, pH 3.5-9.3).

TABLE 1

Specific activity and pI.

| Enzyme | Specific activity NU/ml Phadebas | Specific activity NU/ml pNPG7 | pI |
|---|---|---|---|
| AA560 (SEQ ID NO: 4) | 35000 | 6000 | 7-8 |
| SP722 (SEQ ID NO: 2) | 35000 | 6000 | 7-9 |
| SP690 (SEQ ID NO: 1) | 35000 | 7000 | 5-6 |

$E = 3.2\ cm^{-1} * (g/l)^{-1}$ for AA560, SP722 and SP690

The result of the pH-optimum determination and temperature optimum determination is shown in FIG. 2 and FIG. 3, respectively.

Example 12

Washing Test

Washing performance was evaluated by washing soiled test swatches for 15 and 30 minutes at 25° C. and 40° C., respectively, in detergent solutions with the AA560 alpha-amylase of the invention.

The detergents used are disclosed in Table 2 below. The A/P Model Detergent is described in the Materials section above. The other detergents are commercially available detergents. Commercial detergents containing amylase were inactivated by microwaves before wash.

The purified recombinant AA560 alpha-amylase of Example 6 was added to the detergent solutions at the concentration indicated below. The test swatches were soiled with orange rice starch (CS-28 swatches available from CFT, Center for Test Material, Holland). After washing, the swatches were evaluated by measuring the remission at 460 nm using a Elrepho Remission Spectrophotometer. The results are expressed as ÄR=remission of the swatch washed with the alpha-amylase minus the remission of a swatch washed at the same conditions without the alpha-amylase.

TABLE 2

Detergents and wash conditions.

| Area | Detergent | Det. Dose g/l | Inactivation | Enzyme dose mg/l | Temp. ° C. | Time min | pH | Water hardness °dH | Ca:Mg |
|---|---|---|---|---|---|---|---|---|---|
| A/P | Model detergent 97 | 3 | – | 1 | 25 | 15 | 10.5 | 6 | 2:1 |
| Latin America | Omo Multi Acao | 3 | – | 1 | 25 | 15 | 10.6 | 6 | 2:1 |
| Europe | Omo conc. Powder | 4 | + | 0.2 | 40 | 30 | 10.2 | 15 | 4:1 |
| Europe | Ariel Futur liquid | 5 | + | 0.2 | 40 | 30 | 9.0 | 15 | 4:1 |

The results are shown in FIGS. 4-7. The results demonstrate that the alpha-amylase of the invention is effective in both detergents at highly alkaline pH.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

REFERENCES CITED

Klein, C., et al., *Biochemistry* 1992, 31, 8740-8746.
Mizuno, H., et al., *J. Mol. Biol.* (1993) 234, 1282-1283.
Chang, C., et al, *J. Mol. Biol.* (1993) 229, 235-238.
Larson, S. B., *J. Mol. Biol.* (1994) 235, 1560-1584.
Lawson, C. L., *J. Mol. Biol.* (1994) 236, 590-600.
Qian, M., et al., *J. Mol. Biol.* (1993) 231, 785-799.
Brady, R. L., et al., *Acta Crystallogr. sect. B*, 47, 527-535.
Swift, H. J., et al., *Acta Crystallogr. sect. B*, 47, 535-544.
A. Kadziola, Ph.D. Thesis: "An alpha-amylase from Barley and its Complex with a Substrate Analogue Inhibitor Studied by X-ray Crystallography", Department of Chemistry University of Copenhagen 1993.
MacGregor, E. A., Food Hydrocolloids, 1987, Vol. 1, No. 5-6.
B. Diderichsen and L. Christiansen, Cloning of a maltogenic alpha-amylase from *Bacillus stearothermophilus*, FEMS Microbiol. letters: 56: pp. 53-60 (1988).
Hudson et al., Practical Immunology, Third edition (1989), Blackwell Scientific Publications.
Sambrook et al., *Molecular Cloning: A Laboratory Manual*, 2nd Ed., Cold Spring Harbor, 1989.
S. L. Beaucage and M. H. Caruthers, *Tetrahedron Letters* 22, 1981, pp. 1859-1869
Matthes et al., *The EMBO J.* 3, 1984, pp. 801-805.
R. K. Saiki et al., *Science* 239, 1988, pp. 487-491.
Morinaga et al., (1984, Biotechnology 2:646-639)
Nelson and Long, *Analytical Biochemistry* 180, 1989, pp. 147-151
Hunkapiller et al., 1984, Nature 310:105-111
R. Higuchi, B. Krummel, and R. K. Saiki (1988). A general method of in vitro preparation and specific mutagenesis of DNA fragments: study of protein and DNA interactions. *Nucl. Acids Res.* 16:7351-7367.
Dubnau et al., 1971, *J. Mol. Biol.* 56, pp. 209-221.
Gryczan et al., 1978, *J. Bacteriol.* 134, pp. 318-329.
S. D. Erlich, 1977, *Proc. Natl. Acad. Sci.* 74, pp. 1680-1682.
Boel et al., 1990, *Biochemistry* 29, pp. 6244-6249.
Ausubel, F. M. et al. (eds.); *Current protocols in Molecular Biology*; 1995; John Wiley and Sons.
Harwood C. R., and Cutting S. M. (eds.); *Molecular Biological Methods for Bacillus;* 1990; John Wiley and Sons.
Diderichsen B., Wedsted U., Hedegaard L., Jensen B. R., Sjøholm C.; Cloning of aldB, which encodes alpha-acetolactate decarboxylase, an exoenzyme from *Bacillus brevis;* J. Bacteriol., 1990, vol. 172, pp. 4315-4321.
Pitcher D. G., Saunders N. A., Owen R. J.; Rapid extraction of bacterial genomic DNA with guanidium thiocyanate; *Lett. Appl. Microbiol.;* 1989; vol. 8; pp. 151-156.
Dretzen G., Bellard M., Sassone-Corsi P., Chambon P.; A reliable method for the recovery of DNA fragments from agarose and acrylamide gels; *Anal. Biochem.;* 1981; vol. 112; pp. 295-298.

---

The invention claimed is:

1. A variant alpha-amylase comprising a mutation at a position corresponding to position 193 and a substitution at a position corresponding to position 267, wherein
   (a) the variant alpha-amylase has at least 90% sequence identity with any of SEQ ID NOS: 1-6;
   (b) each position corresponds to the amino acid sequence of relative to SEQ ID NO: 3; and
   (c) the variant alpha-amylase has alpha-amylase activity.

2. The variant alpha-amylase of claim 1, wherein the mutation at a position corresponding to position 193 is a substitution with A, R, D, C, E, Q, G, H, I, L, K, M, F, P, S, T, W, Y, or V.

3. The variant alpha-amylase of claim 1, wherein the mutation at a position corresponding to position 193 is a substitution with F.

4. The variant alpha-amylase of claim 1, wherein the substitution at a position corresponding to position 267 is a substitution with A,R,D,N,C,E,Q,G,H,I,L,K,M,F,P,T,W,Y,V.

5. The variant alpha-amylase of claim 1, which has at least 95% sequence identity with the amino acid sequence of SEQ ID NO: 1, 2, 3, 4, 5, or 6.

6. The variant alpha-amylase of claim 1, which further comprises a substitution at a position corresponding to position 204.

7. The variant alpha-amylase of claim 6, wherein the mutation at a position corresponding to position 204 is a substitution with A,R,D,N,C,E,Q,G,H,I,K,M,F,P,S,T,W,Y,V.

8. The variant alpha-amylase of claim 1, which further comprises a substitution at a position corresponding to position 210.

9. The variant alpha-amylase of claim 8, wherein the substitution at a position corresponding to position 210 is a substitution with A,R,D,N,C,Q,G,H,I,L,K,M,F,P,S,T,W,Y,V.

10. The variant alpha-amylase of claim 1, which further comprises a substitution at a position corresponding to position 214.

11. The variant alpha-amylase of claim 10, wherein the substitution at a position corresponding to position 214 is a substitution with A,R,D,N,C,Q,G,H,I,L,K,M,F,P,S,T,W,Y,V.

12. The variant alpha-amylase of claim 1, further comprising a mutation at a position corresponding to position 181, 182, 183 or 184.

13. The variant alpha-amylase of claim 12, wherein the mutation at a position corresponding to position 181, 182, 183 or 184 is a deletion.

14. The variant alpha-amylase of claim 1, further comprising a deletion at the positions corresponding to positions 181 and 182.

15. A detergent composition, comprising the variant alpha-amylase of claim 1 and a surfactant.

16. The detergent composition of claim 15, further comprising one or more enzymes selected from the group consisting of cellulose, lipase, peroxidase and protease.

17. A method of liquefying starch, comprising treating a starch with the variant alpha-amylase of claim 1.

18. A method of desizing a textile, comprising treating a sized textile with the variant alpha-amylase of claim 1.

* * * * *

UNITED STATES PATENT AND TRADEMARK OFFICE
CERTIFICATE OF CORRECTION

| | | |
|---|---|---|
| PATENT NO. | : 8,263,368 B2 | Page 1 of 1 |
| APPLICATION NO. | : 12/493860 | |
| DATED | : September 11, 2012 | |
| INVENTOR(S) | : Svendsen et al. | |

It is certified that error appears in the above-identified patent and that said Letters Patent is hereby corrected as shown below:

ON THE TITLE PAGE:

Please amend Item (62) Related U.S. Application Data as follows:

Division of application No. 10/327,837, filed on Dec. 23, 2002, now Pat. No. 7,566,561, which is a division of application No. 09/545,586, filed on Apr. 7, 2000, now Pat. No. 6,528,298, which is a division of application No. 09/290,734, filed on Apr. 13, 1999, now Pat. No. 6,361,989, which is a ~~division~~ continuation-in-part of application No. 09/170,670, filed on Oct. 13, 1998, now Pat. No. 6,187,576.

Signed and Sealed this
Nineteenth Day of March, 2013

Teresa Stanek Rea
*Acting Director of the United States Patent and Trademark Office*

SEQUENCE LISTING

<160> NUMBER OF SEQ ID NOS: 37

<210> SEQ ID NO 1
<211> LENGTH: 485
<212> TYPE: PRT
<213> ORGANISM: Bacillus sp.

<400> SEQUENCE: 1

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
        115                 120                 125

Gln Glu Thr Ser Gly Glu Tyr Ala Ile Glu Ala Trp Thr Lys Phe Asp
            130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile His Glu Leu Arg Asn Trp Gly Val Trp Tyr
        210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Gly Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                325                 330                 335

Gly Glu Ala Leu Glu Ser Phe Val Gln Gln Trp Phe Lys Pro Leu Ala
            340                 345                 350

Tyr Ala Leu Val Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
                405                 410                 415

Gly Asn Ser Ser His Pro Asn Ser Gly Leu Ala Thr Ile Met Ser Asp
            420                 425                 430

Gly Pro Gly Gly Asn Lys Trp Met Tyr Val Gly Lys Asn Lys Ala Gly
        435                 440                 445

Gln Val Trp Arg Asp Ile Thr Gly Asn Arg Thr Gly Thr Val Thr Ile
        450                 455                 460

Asn Ala Asp Gly Trp Gly Asn Phe Ser Val Asn Gly Gly Ser Val Ser
465                 470                 475                 480

Val Trp Val Lys Gln
                485

<210> SEQ ID NO 2
<211> LENGTH: 485
<212> TYPE: PRT
<213> ORGANISM: Bacillus sp.

<400> SEQUENCE: 2

His His Asn Gly Thr Asn Gly Thr Met Met Gln Tyr Phe Glu Trp His
1               5                   10                  15

```
Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
 50                  55                  60

Asp Leu Gly Glu Phe Asn Gln Lys Gly Thr Val Arg Thr Lys Tyr Gly
 65                  70                  75                  80

Thr Arg Ser Gln Leu Glu Ser Ala Ile His Ala Leu Lys Asn Asn Gly
            85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
            115                 120                 125

Gln Glu Ile Ser Gly Asp Tyr Thr Ile Glu Ala Trp Thr Lys Phe Asp
            130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
            165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
            195                 200                 205

Asp His Pro Glu Val Val Asn Glu Leu Arg Arg Trp Gly Glu Trp Tyr
            210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
            245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
            275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
            325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
            355                 360                 365

Gly Asp Tyr Tyr Gly Ile Pro Thr His Ser Val Pro Ala Met Lys Ala
 370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
            405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
```

```
                    435                 440                 445
Gln Val Trp His Asp Ile Thr Gly Asn Lys Pro Gly Thr Val Thr Ile
450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 3
<211> LENGTH: 514
<212> TYPE: PRT
<213> ORGANISM: B. stearothermophilus

<400> SEQUENCE: 3

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
50                  55                  60

Leu Gly Glu Phe Asn Gln Lys Gly Ala Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Ser Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Asp Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Met Lys Thr Asn Gly Thr Met Ser Leu Phe Asp
        275                 280                 285

Ala Pro Leu His Asn Lys Phe Tyr Thr Ala Ser Lys Ser Gly Gly Thr
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
```

```
                      325                 330                 335
Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
        370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Trp Ser Ile Thr Thr
                485                 490                 495

Arg Pro Trp Thr Asp Glu Phe Val Arg Trp Thr Glu Pro Arg Leu Val
            500                 505                 510

Ala Trp

<210> SEQ ID NO 4
<211> LENGTH: 483
<212> TYPE: PRT
<213> ORGANISM: B. licheniformis

<400> SEQUENCE: 4

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190
```

Tyr Asp Tyr Leu Met Tyr Ala Asp Ile Asp Tyr Asp His Pro Asp Val
            195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg

<210> SEQ ID NO 5
<211> LENGTH: 480
<212> TYPE: PRT
<213> ORGANISM: B. amyloliquefaciens

<400> SEQUENCE: 5

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

```
Leu Gln Asp Ala Ile Gly Ser Leu His Ser Arg Asn Val Gln Val Tyr
                85                  90                  95

Gly Asp Val Val Leu Asn His Lys Ala Gly Asp Ala Thr Glu Asp
            100                 105                 110

Val Thr Ala Val Glu Val Asn Pro Ala Asn Arg Asn Gln Glu Thr Ser
            115                 120                 125

Glu Glu Tyr Gln Ile Lys Ala Trp Thr Asp Phe Arg Phe Pro Gly Arg
        130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Gly Tyr Asp Met
290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Thr Ser Pro Lys Glu Ile Pro Ser Leu Lys Asp Asn Ile
370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
        450                 455                 460

Asp Gly Trp Gly Glu Phe His Val Asn Asp Gly Ser Val Ser Ile Tyr
465                 470                 475                 480

<210> SEQ ID NO 6
<211> LENGTH: 485
<212> TYPE: PRT
<213> ORGANISM: Bacillus sp.
```

<400> SEQUENCE: 6

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415
```

-continued

Gly Asn Thr Ala His Pro Asn Ser Gly Leu Ala Thr Ile Met Ser Asp
                420                 425                 430

Gly Ala Gly Gly Ser Lys Trp Met Phe Val Gly Arg Asn Lys Ala Gly
            435                 440                 445

Gln Val Trp Ser Asp Ile Thr Gly Asn Arg Thr Gly Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 7
<211> LENGTH: 485
<212> TYPE: PRT
<213> ORGANISM: Bacillus sp.

<400> SEQUENCE: 7

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
        115                 120                 125

Gln Glu Thr Ser Gly Glu Tyr Ala Ile Glu Ala Trp Thr Lys Phe Asp
    130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile His Glu Leu Arg Asn Trp Gly Val Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Gly Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
    290                 295                 300

```
Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
            325                 330                 335

Gly Glu Ala Leu Glu Ser Phe Val Gln Gln Trp Phe Lys Pro Leu Ala
            340                 345                 350

Tyr Ala Leu Val Leu Thr Arg Glu Gln Gly Tyr Pro Ser Val Phe Tyr
            355                 360                 365

Gly Asp Tyr Tyr Gly Ile Pro Thr His Gly Val Pro Ala Met Lys Ser
        370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
                405                 410                 415

Gly Asn Ser Ser His Pro Asn Ser Gly Leu Ala Thr Ile Met Ser Asp
            420                 425                 430

Gly Pro Gly Gly Asn Lys Trp Met Tyr Val Gly Lys Asn Lys Ala Gly
        435                 440                 445

Gln Val Trp Arg Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Val Trp Val Lys Gln
                485

<210> SEQ ID NO 8
<211> LENGTH: 485
<212> TYPE: PRT
<213> ORGANISM: Bacillus sp.

<400> SEQUENCE: 8

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190
```

Ser Glu Asn Gly Asn Tyr Asp Tyr Leu Met Tyr Ala Asp Val Asp Met
    195                 200                 205

Asp His Pro Glu Val Val Asn Glu Leu Arg Arg Trp Gly Glu Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
    290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
    370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
    450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 9
<211> LENGTH: 1455
<212> TYPE: DNA
<213> ORGANISM: Bacillus sp.

<400> SEQUENCE: 9
catcataatg gaacaaatgg tactatgatg caatatttcg aatggtatt  gccaaatgac      60 gggaatcatt ggaacaggtt gagggatgac gcagctaact taaagagtaa agggataaca     120
gctgtatgga tcccacctgc atggaagggg acttcccaga atgatgtagg ttatggagcc     180
tatgatttat atgatcttgg agagtttaac cagaaggggc cggttcgtac aaaatatgga     240
acacgcaacc agctacaggc tgcggtgacc tcttttaaaa ataacggcat tcaggtatat     300
ggtgatgtcg tcatgaatca taaaggtgga gcagatggta cggaaattgt aaatgcggta     360
gaagtgaatc ggagcaaccg aaaccaggaa acctcaggag agtatgcaat agaagcgtgg     420

```
acaaagtttg attttcctgg aagaggaaat aaccattcca gctttaagtg gcgctggtat        480
cattttgatg ggacagattg ggatcagtca cgccagcttc aaaacaaaat atataaattc        540
aggggaacag gcaaggcctg ggactgggaa gtcgatacag agaatggcaa ctatgactat        600
cttatgtatg cagacgtgga tatggatcac ccagaagtaa tacatgaact tagaaactgg        660
ggagtgtggt atacgaatac actgaacctt gatggattta aatagatgc agtgaaacat         720 ataaaatata gctttacgag agattggctt acacatgtgc gtaacaccac aggtaaacca        780
atgtttgcag tggctgagtt ttggaaaaat gaccttggtg caattgaaaa ctatttgaat        840
aaaacaagtt ggaatcactc ggtgtttgat gttcctctcc actataattt gtacaatgca       900
tctaatagcg gtggttatta tgatatgaga aatattttaa atggttctgt ggtgcaaaaa       960
catccaacac atgccgttac ttttgttgat aaccatgatt ctcagcccgg ggaagcattg       1020
gaatcctttg ttcaacaatg gtttaaacca cttgcatatg cattggttct gacaagggaa      1080
caaggttatc cttccgtatt ttatggggat tactacggta tcccaaccca tggtgttccg       1140
gctatgaaat ctaaaataga ccctcttctg caggcacgtc aaacttttgc ctatggtacg       1200
cagcatgatt actttgatca tcatgatatt atcggttgga caagagaggg aaatagctcc       1260
catccaaatt caggccttgc caccattatg tcagatggtc caggtggtaa caaatggatg      1320
tatgtgggga aaaataaagc gggacaagtt tggagagata ttaccggaaa taggacaggc      1380
accgtcacaa ttaatgcaga cggatggggt aatttctctg ttaatggagg gtccgtttcg      1440
gtttgggtga agcaa                                                                                1455

<210> SEQ ID NO 10
<211> LENGTH: 1455
<212> TYPE: DNA
<213> ORGANISM: Bacillus sp.

<400> SEQUENCE: 10
catcataatg ggacaaatgg gacgatgatg caatactttg aatggcactt gcctaatgat         60
gggaatcact ggaatagatt aagagatgat gctagtaatc taagaaatag aggtataacc       120
gctatttgga ttccgcctgc ctggaaaggg acttcgcaaa atgatgtggg gtatggagcc       180
tatgatcttt atgatttagg ggaatttaat caaaagggga cggttcgtac taagtatggg       240
acacgtagtc aattggagtc tgccatccat gctttaaaga ataatggcgt tcaagtttat       300
ggggatgtag tgatgaacca taaaggagga gctgatgcta cagaaaacgt tcttgctgtc       360
gaggtgaatc caaataaccg gaatcaagaa atatctgggg actacacaat tgaggcttgg       420
actaagtttg attttccagg gaggggtaat acatactcag actttaaatg gcgttggtat       480
catttcgatg gtgtagattg ggatcaatca cgacaattcc aaaatcgtat ctacaaattc       540
cgaggtgatg gtaaggcatg ggattgggaa gtagattcgg aaaatggaaa ttatgattat       600
ttaatgtatg cagatgtaga tatggatcat ccggaggtag taaatgagct tagaagatgg       660
ggagaatggt atacaaatac attaaatctt gatggattta ggatcgatgc ggtgaagcat       720
attaaatata gctttacacg tgattggttg acccatgtaa gaaacgcaac gggaaaagaa       780
atgtttgctg ttgctgaatt ttggaaaaat gatttaggtg ccttggagaa ctatttaaat       840
aaaacaaact ggaatcattc tgtctttgat gtccccttc attataatct ttataacgcg        900
tcaaatagtg gaggcaacta tgacatggca aaacttctta tggaacggt tgttcaaaag       960 catccaatgc atgccgtaac ttttgtggat aatcacgatt ctcaacctgg ggaatcatta      1020
gaatcatttg tacaagaatg gtttaagcca cttgcttatg cgcttatttt aacaagagaa       1080
```

```
caaggctatc cctctgtctt ctatggtgac tactatggaa ttccaacaca tagtgtccca    1140
gcaatgaaag ccaagattga tccaatctta gaggcgcgtc aaaattttgc atatggaaca    1200
caacatgatt attttgacca tcataatata atcggatgga cacgtgaagg aaataccacg    1260
catcccaatt caggacttgc gactatcatg tcggatgggc caggggggaga gaaatggatg    1320 tacgtagggc aaaataaagc aggtcaagtt tggcatgaca taactggaaa taaaccagga    1380
acagttacga tcaatgcaga tggatgggct aatttttcag taaatggagg atctgtttcc    1440
atttgggtga aacga                                                      1455

<210> SEQ ID NO 11
<211> LENGTH: 1548
<212> TYPE: DNA
<213> ORGANISM: B. stearothermophilus

<400> SEQUENCE: 11
gccgcaccgt ttaacggcac catgatgcag tattttgaat ggtacttgcc ggatgatggc      60
acgttatgga ccaaagtggc caatgaagcc aacaacttat ccagccttgg catcaccgct     120
ctttggctgc cgcccgctta caaggaaca agccgcagcg acgtagggta cggagtatac       180
gacttgtatg acctcggcga attcaatcaa aaagggaccg tccgcacaaa atacggaaca     240
aaagctcaat atcttcaagc cattcaagcc gcccacgccg ctggaatgca agtgtacgcc     300
gatgtcgtgt tcgaccataa aggcggcgct gacggcacgg aatgggtgga cgccgtcgaa     360
gtcaatccgt ccgaccgcaa ccaagaaatc tcgggcacct atcaaatcca agcatggacg     420
aaatttgatt tccccgggcg gggcaacacc tactccagct ttaagtggcg ctggtaccat     480
tttgacggcg ttgattggga cgaaagccga aaattgagcc gcatttacaa attccgcggc     540
atcggcaaag cgtgggattg ggaagtagac acggaaaacg gaaactatga ctacttaatg     600
tatgccgacc ttgatatgga tcatcccgaa gtcgtgaccg agctgaaaaa ctgggggaaa     660
tggtatgtca acacaacgaa cattgatggg ttccggcttg atgccgtcaa gcatattaag     720
ttcagttttt ttcctgattg gttgtcgtat gtgcgttctc agactggcaa gccgctattt     780
accgtcgggg aatattggag ctatgacatc aacaagttgc acaattacat tacgaaaaca     840
gacggaacga tgtctttgtt tgatgccccg ttacacaaca aattttatac cgcttccaaa     900 tcaggggggcg catttgatat cgcacgttta atgaccaata ctctcatgaa agatcaaccg     960
acattggccg tcaccttcgt tgataatcat gacaccgaac ccggccaagc gctgcagtca    1020
tgggtcgacc catggttcaa accgttggct tacgccttta ttctaactcg gcaggaagga    1080
tacccgtgcg tcttttatgg tgactattat ggcattccac aatataacat tccttcgctg    1140
aaaagcaaaa tcgatccgct cctcatcgcg cgcagggatt atgcttacgg aacgcaacat    1200
gattatcttg atcactccga catcatcggg tggacaaggg aaggggcac tgaaaaacca     1260 ggatccggac tggccgcact gatcaccgat gggccgggag aagcaaatg gatgtacgtt      1320 ggcaaacaac acgctggaaa agtgttctat gaccttaccg caaccggag tgacaccgtc     1380 accatcaaca gtgatggatg gggggaattc aaagtcaatg cggttcggt ttcggttttgg     1440 gttcctagaa aaacgaccgt ttctaccatc gctcggccga tcacaacccg accgtggact    1500
ggtgaattcg tccgttggac cgaaccacgg ttggtggcat ggccttga                 1548

<210> SEQ ID NO 12
<211> LENGTH: 1920
<212> TYPE: DNA
<213> ORGANISM: B. licheniformis
```

<400> SEQUENCE: 12

```
cggaagattg gaagtacaaa aataagcaaa agattgtcaa tcatgtcatg agccatgcgg      60
gagacggaaa aatcgtctta atgcacgata tttatgcaac gttcgcagat gctgctgaag     120
agattattaa aaagctgaaa gcaaaaggct atcaattggt aactgtatct cagcttgaag     180
aagtgaagaa gcagagaggc tattgaataa atgagtagaa gcgccatatc ggcgcttttc     240
ttttggaaga aaatataggg aaaatggtac ttgttaaaaa ttcggaatat ttatacaaca     300
tcatatgttt cacattgaaa ggggaggaga atcatgaaac aacaaaaacg gctttacgcc     360
cgattgctga cgctgttatt tgcgctcatc ttcttgctgc ctcattctgc agcagcggcg     420
gcaaatctta atgggacgct gatgcagtat tttgaatggt acatgcccaa tgacggccaa     480
cattggaggc gtttgcaaaa cgactcggca tatttggctg aacacggtat tactgccgtc     540
tggattcccc cggcatataa gggaacgagc caagcggatg tgggctacgg tgcttacgac     600
ctttatgatt tagggagtt tcatcaaaaa gggacggttc ggacaaagta cggcacaaaa     660
ggagagctgc aatctgcgat caaaagtctt cattcccgcg acattaacgt ttacggggat     720
gtggtcatca accacaaagg cggcgctgat gcgaccgaag atgtaaccgc ggttgaagtc     780
gatcccgctg accgcaaccg cgtaatttca ggagaacacc taattaaagc ctggacacat     840
tttcattttc cggggcgcgg cagcacatac agcgatttta aatggcattg gtaccatttt     900
gacggaaccg attgggacga gtcccgaaag ctgaaccgca tctataagtt tcaaggaaag     960
gcttgggatt gggaagtttc caatgaaaac ggcaactatg attatttgat gtatgccgac    1020
atcgattatg accatcctga tgtcgcagca gaaattaaga gatggggcac ttggtatgcc    1080
aatgaactgc aattggacgg tttccgtctt gatgctgtca aacacattaa attttctttt    1140
ttgcgggatt gggttaatca tgtcagggaa aaaacgggga aggaaatgtt tacggtagct    1200
gaatattggc agaatgactt gggcgcgctg gaaaactatt tgaacaaaac aaattttaat    1260
cattcagtgt ttgacgtgcc gcttcattat cagttccatg ctgcatcgac acagggaggc    1320
ggctatgata tgaggaaatt gctgaacggt acggtcgttt ccaagcatcc gttgaaatcg    1380
gttacatttg tcgataacca tgatacacag ccggggcaat cgcttgagtc gactgtccaa    1440
acatggttta agccgcttgc ttacgctttt attctcacaa gggaatctgg ataccctcag    1500
gttttctacg gggatatgta cgggacgaaa ggagactccc agcgcgaaat tcctgccttg    1560
aaacacaaaa ttgaaccgat cttaaaagcg agaaacagt atgcgtacgg agcacagcat    1620
gattatttcg accaccatga cattgtcggc tggacaaggg aaggcgacag ctcggttgca    1680
aattcaggtt tggcggcatt aataacagac ggacccggtg gggcaaagcg aatgtatgtc    1740
ggccggcaaa acgccggtga gacatggcat gacattaccg gaaaccgttc ggagccggtt    1800
gtcatcaatt cggaaggctg gggagagttt cacgtaaacg gcgggtcggt ttcaatttat    1860
gttcaaagat agaagagcag agaggacgga tttcctgaag gaaatccgtt ttttatttt    1920
```

<210> SEQ ID NO 13
<211> LENGTH: 2084
<212> TYPE: DNA
<213> ORGANISM: B. amyloliquefaciens

<400> SEQUENCE: 13

```
gccccgcaca tacgaaaaga ctggctgaaa acattgagcc tttgatgact gatgatttgg      60
ctgaagaagt ggatcgattg tttgagaaaa gaagaagacc ataaaaatac cttgtctgtc     120
atcagacagg gtatttttta tgctgtccag actgtccgct gtgtaaaaat aaggaataaa     180
```

-continued

```
gggggggttgt tattattttta ctgatatgta aaatataatt tgtataagaa aatgagaggg      240
agaggaaaca tgattcaaaa acgaaagcgg acagtttcgt tcagacttgt gcttatgtgc       300
acgctgttat ttgtcagttt gccgattaca aaacatcag ccgtaaatgg cacgctgatg        360
cagtattttg aatggtatac gccgaacgac ggccagcatt ggaaacgatt gcagaatgat       420
gcggaacatt tatcggatat cggaatcact gccgtctgga ttcctcccgc atacaaagga      480
ttgagccaat ccgataacgg atacggacct tatgatttgt atgatttagg agaattccag      540
caaaaaggga cggtcagaac gaaatacggc acaaaatcag agcttcaaga tgcgatcggc     600
tcactgcatt cccggaacgt ccaagtatac ggagatgtgg ttttgaatca taaggctggt      660
gctgatgcaa cagaagatgt aactgccgtc gaagtcaatc cggccaatag aaatcaggaa     720
acttcggagg aatatcaaat caaagcgtgg acggattttc gttttccggg ccgtggaaac     780
acgtacagtg attttaaatg gcattggtat catttcgacg gagcggactg ggatgaatcc     840
cggaagatca gccgcatctt taagtttcgt ggggaaggaa aagcgtggga ttgggaagta    900
tcaagtgaaa acggcaacta tgactatttta atgtatgctg atgttgacta cgaccaccct    960
gatgtcgtgg cagagacaaa aaaatggggt atctggtatg cgaatgaact gtcattagac     1020
ggcttccgta ttgatgccgc caaacatatt aaattttcat ttctgcgtga ttgggttcag     1080
gcggtcagac aggcgacggg aaaagaaatg tttacggttg cggagtattg cagaataat     1140 gccgggaaac tcgaaaacta cttgaataaa acaagcttta atcaatccgt gtttgatgtt     1200
ccgcttcatt tcaatttaca gcggcttcc tcacaaggag gcggatatga tatgaggcgt    1260
ttgctggacg gtaccgttgt gtccaggcat ccggaaaagg cggttacatt tgttgaaaat    1320
catgacacac agccgggaca gtcattggaa tcgacagtcc aaacttggtt taaaccgctt    1380
gcatacgcct ttattttgac aagagaatcc ggttatcctc aggtgttcta tgggatatg    1440 tacgggacaa aagggacatc gccaaaggaa attccctcac tgaaagataa tatagagccg    1500 atttaaaag cgcgtaagga gtacgcatac gggccccagc acgattatat tgaccacccg     1560
gatgtgatcg gatggacgag ggaaggtgac agctccgccg ccaaatcagg tttggccgct    1620
ttaatcacgg acggacccgg cggatcaaag cggatgtatg ccggcctgaa aaatgccggc    1680
gagacatggt atgacataac gggcaaccgt tcagatactg taaaaatcgg atctgacggc    1740
tggggagagt tcatgtaaa cgatgggtcc gtctccattt atgttcagaa ataaggtaat     1800
aaaaaaacac ctccaagctg agtgcgggta tcagcttgga ggtgcgttta ttttttcagc    1860
cgtatgacaa ggtcggcatc agtgtgtgaca aatacggtat gctggctgtc ataggtgaca    1920
aatccgggtt ttgcgccgtt tggcttttttc acatgtctga ttttttgtata atcaacaggc    1980 acggagccga aatctttcgc cttggaaaaa taagcggcga tcgtagctgc ttccaatatg    2040
gattgttcat cgggatcgct gctttttaatc acaacgtggg atcc                      2084
```

<210> SEQ ID NO 14
<211> LENGTH: 1395
<212> TYPE: DNA
<213> ORGANISM: Bacillus sp.

<400> SEQUENCE: 14

```
gggaatcatt ggaacaggtt gagggatgac gcagctaact taaagagtaa agggataaca      60
gctgtatgga tcccacctgc atggaagggg acttcccaga atgatgtagg ttatggagcc     120
tatgatttat atgatcttgg agagtttaac cagaagggga cggttcgtac aaaatatgga    180
acacgcaacc agctacaggc tgcggtgacc tcttaaaaa ataacggcat tcaggtatat     240
```

```
ggtgatgtcg tcatgaatca taaaggtgga gcagatggta cggaaattgt aaatgcggta      300
gaagtgaatc ggagcaaccg aaaccaggaa acctcaggag agtatgcaat agaagcgtgg      360
acaaagtttg atttcctgg aagaggaaat aaccattcca gctttaagtg gcgctggtat       420
cattttgatg ggacagattg ggatcagtca cgccagcttc aaaacaaaat atataaattc      480
aggggaacag gcaaggcctg ggactgggaa gtcgatacag agaatggcaa ctatgactat      540
cttatgtatg cagacgtgga tatggatcac ccagaagtaa tacatgaact agaaactgg       600
ggagtgtggt atacgaatac actgaacctt gatggattta aatagatgc agtgaaacat       660
ataaaatata gctttacgag agattggctt acacatgtgc gtaacaccac aggtaaacca      720
atgtttgcag tggctgagtt ttggaaaaat gaccttggtg caattgaaaa ctatttgaat      780
aaaacaagtt ggaatcactc ggtgtttgat gttcctctcc actataattt gtacaatgca      840
tctaatagcg gtggttatta tgatatgaga atatttttaa atggttctgt ggtgcaaaaa      900
catccaacac atgccgttac ttttgttgat aaccatgatt ctcagcccgg ggaagcattg      960
gaatcctttg ttcaacaatg gtttaaacca cttgcatatg cattggttct gacaagggaa     1020
caaggttatc cttccgtatt ttatgggat tactacggta tcccaaccca tggtgttccg      1080
gctatgaaat ctaaaataga ccctcttctg caggcacgtc aaacttttgc ctatggtacg     1140
cagcatgatt actttgatca tcatgatatt atcggttgga caagagggg aaatagctcc      1200
catccaaatt caggccttgc caccattatg tcagatggtc caggtggtaa caaatggatg     1260
tatgtgggga aaaataaagc gggacaagtt tggagagata ttaccggaaa taggacaggc     1320
accgtcacaa ttaatgcaga cggatggggt aatttctctg ttaatggagg gtccgtttcg     1380
gtttgggtga agcaa                                                     1395

<210> SEQ ID NO 15
<211> LENGTH: 1455
<212> TYPE: DNA
<213> ORGANISM: Bacillus sp.

<400> SEQUENCE: 15
catcataatg ggacaaatgg gacgatgatg caatactttg aatggcactt gcctaatgat       60
gggaatcact ggaatagatt aagagatgat gctagtaatc taagaaatag aggtataacc      120
gctatttgga ttccgcctgc ctggaaaggg acttcgcaaa atgatgtggg gtatggagcc      180
tatgatcttt atgatttagg ggaatttaat caaaggggga cggttcgtac taagtatggg      240
acacgtagtc aattggagtc tgccatccat gctttaaaga ataatggcgt tcaagtttat      300
ggggatgtag tgatgaacca taaaggagga gctgatgcta cagaaaacgt tcttgctgtc      360
gaggtgaatc caaataaccg gaatcaagaa atatctgggg actacacaat tgaggcttgg      420
actaagtttg atttccagg gagggtaat acatactcag actttaaatg gcgttggtat       480
catttcgatg gtgtagattg ggatcaatca cgacaattcc aaaatcgtat ctacaaattc      540
cgaggtgatg gtaaggcatg ggattgggaa gtagattcgg aaaatggaaa ttatgattat      600
ttaatgtatg cagatgtaga tatggatcat ccggaggtag taaatgagct tagaagatgg     660
ggagaatggt atacaaatac attaaatctt gatggattta ggatcgatgc ggtgaagcat      720
attaaatata gctttacacg tgattggttg acccatgtaa gaacgcaac gggaaaagaa      780
atgtttgctg ttgctgaatt ttggaaaaat gatttaggtg ccttggagaa ctatttaaat      840
aaaacaaact ggaatcattc tgtctttgat gtccccttc attataatct ttataacgcg       900
tcaaatagtg gaggcaacta tgacatggca aaacttctta atggaacggt tgttcaaaag      960
```

```
catccaatgc atgccgtaac ttttgtggat aatcacgatt ctcaacctgg ggaatcatta    1020
gaatcatttg tacaagaatg gtttaagcca cttgcttatg cgcttatttt aacaagagaa    1080
caaggctatc cctctgtctt ctatggtgac tactatggaa ttccaacaca tagtgtccca    1140
gcaatgaaag ccaagattga tccaatctta gaggcgcgtc aaaattttgc atatggaaca    1200
caacatgatt attttgacca tcataatata atcggatgga cacgtgaagg aaataccacg    1260
catcccaatt caggacttgc gactatcatg tcggatgggc caggggggaga gaaatggatg    1320 tacgtagggc aaaataaagc aggtcaagtt tggcatgaca taactggaaa taaaccagga    1380
acagttacga tcaatgcaga tggatgggct aattttccag taaatggagg atctgtttcc    1440
atttgggtga aacga                                                     1455
```

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16

```
ccatgatgca gtattttgaa tgg                                              23
```

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17

```
gtcaccataa aagacgcacg gg                                               22
```

<210> SEQ ID NO 18
<211> LENGTH: 68
<212> TYPE: DNA
<213> ORGANISM: Artificial Sequence
<220> FEATURE:
<223> OTHER INFORMATION: Primer

<400> SEQUENCE: 18

```
gtcatagttt ccgaattccg tgtctacttc ccaatcccaa tcccaagctt tgccgcggaa     60
tttgtaaa                                                              68
```

<210> SEQ ID NO 19
<211> LENGTH: 41
<212> TYPE: DNA
<213> ORGANISM: Artificial Sequence
<220> FEATURE:
<223> OTHER INFORMATION: Primer

<400> SEQUENCE: 19

```
ctacttccca atcccaagct tgccgcggga atttgtaaat g                         41
```

<210> SEQ ID NO 20
<211> LENGTH: 27
<212> TYPE: DNA
<213> ORGANISM: Artificial Sequence
<220> FEATURE:
<223> OTHER INFORMATION: Primer

<400> SEQUENCE: 20

```
ggatgatcca tgtcaaagtc ggcatac                                         27
```

<210> SEQ ID NO 21
<211> LENGTH: 25
<212> TYPE: DNA
<213> ORGANISM: Artificial Sequence
<220> FEATURE:
<223> OTHER INFORMATION: Primer

<400> SEQUENCE: 21
ctcggtcacc acgtggggat gatcc                                         25

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22 ccagttttc agctgggtca cgac                                           24

<210> SEQ ID NO 23
<211> LENGTH: 1458
<212> TYPE: DNA
<213> ORGANISM: Bacillus sp
<220> FEATURE:
<221> NAME/KEY: mat_peptide
<222> LOCATION: (1)..(1455)
<220> FEATURE:
<221> NAME/KEY: CDS
<222> LOCATION: (1)..(1455)

<400> SEQUENCE: 23

```
cac cat aat ggt acg aac ggc aca atg atg cag tac ttt gaa tgg tat    48
His His Asn Gly Thr Asn Gly Thr Met Met Gln Tyr Phe Glu Trp Tyr
1               5                   10                  15 cta cca aat gac gga aac cat tgg aat aga tta agg tct gat gca agt    96
Leu Pro Asn Asp Gly Asn His Trp Asn Arg Leu Arg Ser Asp Ala Ser
            20                  25                  30 aac cta aaa gat aaa ggg atc tca gcg gtt tgg att cct cct gca tgg   144
Asn Leu Lys Asp Lys Gly Ile Ser Ala Val Trp Ile Pro Pro Ala Trp
        35                  40                  45 aag ggt gcc tct caa aat gat gtg ggg tat ggt gct tat gat ctg tat   192
Lys Gly Ala Ser Gln Asn Asp Val Gly Tyr Gly Ala Tyr Asp Leu Tyr
    50                  55                  60 gat tta gga gaa ttc aat caa aaa gga acc att cgt aca aaa tat gga   240
Asp Leu Gly Glu Phe Asn Gln Lys Gly Thr Ile Arg Thr Lys Tyr Gly
65                  70                  75                  80 acg cgc aat cag tta caa gct gca gtt aac gcc ttg aaa agt aat gga   288
Thr Arg Asn Gln Leu Gln Ala Ala Val Asn Ala Leu Lys Ser Asn Gly
                85                  90                  95 att caa gtg tat ggc gat gtt gta atg aat cat aaa ggg gga gca gac   336
Ile Gln Val Tyr Gly Asp Val Val Met Asn His Lys Gly Gly Ala Asp
            100                 105                 110 gct acc gaa atg gtt agg gca gtt gaa gta aac ccg aat aat aga aat   384
Ala Thr Glu Met Val Arg Ala Val Glu Val Asn Pro Asn Asn Arg Asn
        115                 120                 125 caa gaa gtg tcc ggt gaa tat aca att gag gct tgg aca aag ttt gac   432
Gln Glu Val Ser Gly Glu Tyr Thr Ile Glu Ala Trp Thr Lys Phe Asp
    130                 135                 140 ttt cca gga cga ggt aat act cat tca aac ttc aaa tgg aga tgg tat   480
Phe Pro Gly Arg Gly Asn Thr His Ser Asn Phe Lys Trp Arg Trp Tyr
145                 150                 155                 160 cac ttt gat gga gta gat tgg gat cag tca cgt aag ctg aac aat cga   528
His Phe Asp Gly Val Asp Trp Asp Gln Ser Arg Lys Leu Asn Asn Arg
```

```
                         165                 170                 175
att tat aaa ttt aga ggt gat gga aaa ggg tgg gat tgg gaa gtc gat    576
Ile Tyr Lys Phe Arg Gly Asp Gly Lys Gly Trp Asp Trp Glu Val Asp
        180                 185                 190 aca gaa aac ggt aac tat gat tac cta atg tat gca gat att gac atg    624
Thr Glu Asn Gly Asn Tyr Asp Tyr Leu Met Tyr Ala Asp Ile Asp Met
            195                 200                 205 gat cac cca gag gta gtg aat gag cta aga aat tgg ggt gtt tgg tat    672
Asp His Pro Glu Val Val Asn Glu Leu Arg Asn Trp Gly Val Trp Tyr
210                 215                 220 acg aat aca tta ggc ctt gat ggt ttt aga ata gat gca gta aaa cat    720
Thr Asn Thr Leu Gly Leu Asp Gly Phe Arg Ile Asp Ala Val Lys His
225                 230                 235                 240 ata aaa tac agc ttt act cgt gat tgg att aat cat gtt aga agt gca    768
Ile Lys Tyr Ser Phe Thr Arg Asp Trp Ile Asn His Val Arg Ser Ala
                245                 250                 255 act ggc aaa aat atg ttt gcg gtt gcg gaa ttt tgg aaa aat gat tta    816
Thr Gly Lys Asn Met Phe Ala Val Ala Glu Phe Trp Lys Asn Asp Leu
            260                 265                 270 ggt gct att gaa aac tat tta aac aaa aca aac tgg aac cat tca gtc    864
Gly Ala Ile Glu Asn Tyr Leu Asn Lys Thr Asn Trp Asn His Ser Val
        275                 280                 285 ttt gat gtt ccg ctg cac tat aac ctc tat aat gct tca aaa agc gga    912
Phe Asp Val Pro Leu His Tyr Asn Leu Tyr Asn Ala Ser Lys Ser Gly
290                 295                 300 ggg aat tat gat atg agg caa ata ttt aat ggt aca gtc gtg caa aga    960
Gly Asn Tyr Asp Met Arg Gln Ile Phe Asn Gly Thr Val Val Gln Arg
305                 310                 315                 320 cat cca atg cat gct gtt aca ttt gtt gat aat cat gat tcg caa cct   1008
His Pro Met His Ala Val Thr Phe Val Asp Asn His Asp Ser Gln Pro
                325                 330                 335 gaa gaa gct tta gag tct ttt gtt gaa gaa tgg ttc aaa cca tta gcg   1056
Glu Glu Ala Leu Glu Ser Phe Val Glu Glu Trp Phe Lys Pro Leu Ala
            340                 345                 350 tat gct ttg aca tta aca cgt gaa caa ggc tac cct tct gta ttt tat   1104
Tyr Ala Leu Thr Leu Thr Arg Glu Gln Gly Tyr Pro Ser Val Phe Tyr
        355                 360                 365 gga gat tat tat ggc att cca acg cat ggt gta cca gcg atg aaa tcg   1152
Gly Asp Tyr Tyr Gly Ile Pro Thr His Gly Val Pro Ala Met Lys Ser
370                 375                 380 aaa att gac ccg att cta gaa gcg cgt caa aag tat gca tat gga aga   1200
Lys Ile Asp Pro Ile Leu Glu Ala Arg Gln Lys Tyr Ala Tyr Gly Arg
385                 390                 395                 400 caa aat gac tac tta gac cat cat aat atc atc ggt tgg aca cgt gaa   1248
Gln Asn Asp Tyr Leu Asp His His Asn Ile Ile Gly Trp Thr Arg Glu
                405                 410                 415 ggg aat aca gca cac ccc aac tcc ggt tta gct act atc atg tcc gat   1296
Gly Asn Thr Ala His Pro Asn Ser Gly Leu Ala Thr Ile Met Ser Asp
            420                 425                 430 ggg gca gga gga aat aag tgg atg ttt gtt ggg cgt aat aaa gct ggt   1344
Gly Ala Gly Gly Asn Lys Trp Met Phe Val Gly Arg Asn Lys Ala Gly
        435                 440                 445 caa gtt tgg acc gat atc act gga aat cgt gca ggt act gtt acg att   1392
Gln Val Trp Thr Asp Ile Thr Gly Asn Arg Ala Gly Thr Val Thr Ile
450                 455                 460 aat gct gat gga tgg ggt aat ttt tct gta aat gga gga tca gtt tct   1440
Asn Ala Asp Gly Trp Gly Asn Phe Ser Val Asn Gly Gly Ser Val Ser
465                 470                 475                 480 att tgg gta aac aaa taa                                           1458
Ile Trp Val Asn Lys
```

485

```
<210> SEQ ID NO 24
<211> LENGTH: 485
<212> TYPE: PRT
<213> ORGANISM: Bacillus sp

<400> SEQUENCE: 24
```

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser

```
                370            375            380
Lys Ile Asp Pro Ile Leu Glu Ala Arg Gln Lys Tyr Ala Tyr Gly Arg
385                390                395                400

Gln Asn Asp Tyr Leu Asp His His Asn Ile Ile Gly Trp Thr Arg Glu
                405                410                415

Gly Asn Thr Ala His Pro Asn Ser Gly Leu Ala Thr Ile Met Ser Asp
                420                425                430

Gly Ala Gly Gly Asn Lys Trp Met Phe Val Gly Arg Asn Lys Ala Gly
                435                440                445

Gln Val Trp Thr Asp Ile Thr Gly Asn Arg Ala Gly Thr Val Thr Ile
                450                455                460

Asn Ala Asp Gly Trp Gly Asn Phe Ser Val Asn Gly Gly Ser Val Ser
465                470                475                480

Ile Trp Val Asn Lys
                485

<210> SEQ ID NO 25
<211> LENGTH: 1458
<212> TYPE: DNA
<213> ORGANISM: Bacillus sp.
<220> FEATURE:
<221> NAME/KEY: mat_peptide
<222> LOCATION: (1)..(1455)
<220> FEATURE:
<221> NAME/KEY: CDS
<222> LOCATION: (1)..(1455)

<400> SEQUENCE: 25 cac cat aat ggt acg aac ggc aca atg atg cag tac ttt gaa tgg tat        48
His His Asn Gly Thr Asn Gly Thr Met Met Gln Tyr Phe Glu Trp Tyr
1               5                   10                  15 cta cca aat gac gga aac cat tgg aat aga tta agg tct gat gca agt        96
Leu Pro Asn Asp Gly Asn His Trp Asn Arg Leu Arg Ser Asp Ala Ser
            20                  25                  30 aac cta aaa gat aaa ggg atc tca gcg gtt tgg att cct cct gca tgg       144
Asn Leu Lys Asp Lys Gly Ile Ser Ala Val Trp Ile Pro Pro Ala Trp
        35                  40                  45 aag ggt gcc tct caa aat gat gtg ggg tat ggt gct tat gat ctg tat       192
Lys Gly Ala Ser Gln Asn Asp Val Gly Tyr Gly Ala Tyr Asp Leu Tyr
    50                  55                  60 gat tta gga gaa ttc aat caa aaa gga acc att cgt aca aaa tat gga       240
Asp Leu Gly Glu Phe Asn Gln Lys Gly Thr Ile Arg Thr Lys Tyr Gly
65                  70                  75                  80 acg cgc aat cag tta caa gct gca gtt aac gcc ttg aaa agt aat gga       288
Thr Arg Asn Gln Leu Gln Ala Ala Val Asn Ala Leu Lys Ser Asn Gly
                85                  90                  95 att caa gtg tat ggc gat gtt gta atg aat cat aaa ggg gga gca gac       336
Ile Gln Val Tyr Gly Asp Val Val Met Asn His Lys Gly Gly Ala Asp
            100                 105                 110 gct acc gaa atg gtt agg gcg gtt gaa gta aac ccg aat aat aga aat       384
Ala Thr Glu Met Val Arg Ala Val Glu Val Asn Pro Asn Asn Arg Asn
        115                 120                 125 caa gaa gtg tcc ggt gaa tat aca att gag gct tgg aca aag ttt gac       432
Gln Glu Val Ser Gly Glu Tyr Thr Ile Glu Ala Trp Thr Lys Phe Asp
    130                 135                 140 ttt cct gga cga ggt aat acc cat tca aac ttc aaa tgg aga tgg tat       480
Phe Pro Gly Arg Gly Asn Thr His Ser Asn Phe Lys Trp Arg Trp Tyr
145                 150                 155                 160 cac ttt gat gga gta gat tgg gat cag tca cgt aag ctg aac aat cga       528
His Phe Asp Gly Val Asp Trp Asp Gln Ser Arg Lys Leu Asn Asn Arg
                165                 170                 175
```

| | | |
|---|---|---|
| att tat aaa ttt aga ggt gat gga aaa ggg tgg gat tgg gaa gtc gat<br>Ile Tyr Lys Phe Arg Gly Asp Gly Lys Gly Trp Asp Trp Glu Val Asp<br>        180                        185                    190 | | 576 |
| aca gaa aac ggt aac tat gat tac cta atg tat gca gat att gac atg<br>Thr Glu Asn Gly Asn Tyr Asp Tyr Leu Met Tyr Ala Asp Ile Asp Met<br>195                        200                        205 | | 624 |
| gat cac cca gag gta gtg aat gag cta aga aat tgg ggt gtt tgg tat<br>Asp His Pro Glu Val Val Asn Glu Leu Arg Asn Trp Gly Val Trp Tyr<br>        210                        215                    220 | | 672 |
| acg aat aca tta ggc ctt gat ggt ttt aga ata gat gca gta aaa cat<br>Thr Asn Thr Leu Gly Leu Asp Gly Phe Arg Ile Asp Ala Val Lys His<br>225                        230                        235                    240 | | 720 |
| ata aaa tac agc ttt act cgt gat tgg atc aat cat gtt aga agt gca<br>Ile Lys Tyr Ser Phe Thr Arg Asp Trp Ile Asn His Val Arg Ser Ala<br>                      245                        250                    255 | | 768 |
| act ggc aaa aat atg ttt gcg gtt gcg gaa ttt tgg aaa aat gat tta<br>Thr Gly Lys Asn Met Phe Ala Val Ala Glu Phe Trp Lys Asn Asp Leu<br>260                        265                        270 | | 816 |
| ggt gct att gaa aac tat tta aac aaa aca aac tgg aac cat tca gtc<br>Gly Ala Ile Glu Asn Tyr Leu Asn Lys Thr Asn Trp Asn His Ser Val<br>        275                        280                    285 | | 864 |
| ttt gat gtt ccg ctg cac tat aac ctc tat aat gct tca aaa agc gga<br>Phe Asp Val Pro Leu His Tyr Asn Leu Tyr Asn Ala Ser Lys Ser Gly<br>290                        295                        300 | | 912 |
| ggg aat tat gat atg agg caa ata ttt aat ggt aca gtc gtg caa aga<br>Gly Asn Tyr Asp Met Arg Gln Ile Phe Asn Gly Thr Val Val Gln Arg<br>305                        310                        315                    320 | | 960 |
| cat cca atg cat gct gtt aca ttt gtt gat aat cat gat tcg caa cct<br>His Pro Met His Ala Val Thr Phe Val Asp Asn His Asp Ser Gln Pro<br>                          325                        330                    335 | | 1008 |
| gaa gaa gct tta gag tct ttt gtt gaa gaa tgg ttc aaa cca tta gcg<br>Glu Glu Ala Leu Glu Ser Phe Val Glu Glu Trp Phe Lys Pro Leu Ala<br>                340                        345                    350 | | 1056 |
| tat gct ttg aca tta aca cgt gaa caa ggc tac cct tct gta ttt tat<br>Tyr Ala Leu Thr Leu Thr Arg Glu Gln Gly Tyr Pro Ser Val Phe Tyr<br>        355                        360                    365 | | 1104 |
| gga gat tat tat ggc att cca acg cat ggt gta cca gcg atg aaa tcg<br>Gly Asp Tyr Tyr Gly Ile Pro Thr His Gly Val Pro Ala Met Lys Ser<br>370                        375                        380 | | 1152 |
| aaa att gac ccg att cta gaa gcg cgt caa aag tat gca tat gga aga<br>Lys Ile Asp Pro Ile Leu Glu Ala Arg Gln Lys Tyr Ala Tyr Gly Arg<br>385                        390                        395                    400 | | 1200 |
| caa aat gac tac tta gac cat cat aat atc att ggt tgg aca cgt gaa<br>Gln Asn Asp Tyr Leu Asp His His Asn Ile Ile Gly Trp Thr Arg Glu<br>                          405                        410                    415 | | 1248 |
| ggg aat aca gca cac ccc aac tct ggt tta gct act atc atg tcc gat<br>Gly Asn Thr Ala His Pro Asn Ser Gly Leu Ala Thr Ile Met Ser Asp<br>                420                        425                    430 | | 1296 |
| gga gca gga gga aat aag tgg atg ttt gtt ggg cgt aat aaa gct ggt<br>Gly Ala Gly Gly Asn Lys Trp Met Phe Val Gly Arg Asn Lys Ala Gly<br>        435                        440                    445 | | 1344 |
| caa gtt tgg acc gat atc act gga aat cgt gca ggt act gtt acg att<br>Gln Val Trp Thr Asp Ile Thr Gly Asn Arg Ala Gly Thr Val Thr Ile<br>450                        455                        460 | | 1392 |
| aat gct gat gga tgg ggt aat ttt tct gta aat gga gga tca gtt tct<br>Asn Ala Asp Gly Trp Gly Asn Phe Ser Val Asn Gly Gly Ser Val Ser<br>465                        470                        475                    480 | | 1440 |
| att tgg gta aac aaa taa<br>Ile Trp Val Asn Lys<br>        485 | | 1458 |

```
<210> SEQ ID NO 26
<211> LENGTH: 485
<212> TYPE: PRT
<213> ORGANISM: Bacillus sp.

<400> SEQUENCE: 26

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
370                 375                 380
```

```
Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
            405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
        435                 440                 445

Gln Val Trp Thr Asp Ile Thr Gly Asn Arg Ala Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
            485

<210> SEQ ID NO 27
<211> LENGTH: 7
<212> TYPE: PRT
<213> ORGANISM: Artificial Sequence
<220> FEATURE:
<223> OTHER INFORMATION: Primer
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 27

Gly Ile Thr Ala Xaa Trp Xaa
1               5

<210> SEQ ID NO 28
<211> LENGTH: 9
<212> TYPE: PRT
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 28

Val Tyr Xaa Asp Xaa Val Xaa Asn His
1               5

<210> SEQ ID NO 29
<211> LENGTH: 10
<212> TYPE: PRT
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: Xaa can be any naturally occurring amino acid
<220> FEATURE:
```

```
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 29

Asp Gly Xaa Arg Xaa Asp Ala Xaa Lys His
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 30

Asp Gly Xaa Arg Xaa Asp Ala Xaa Lys His
1               5                   10

<210> SEQ ID NO 31
<211> LENGTH: 8
<212> TYPE: PRT
<213> ORGANISM: Artificial Sequence
<220> FEATURE:
<223> OTHER INFORMATION: Primer
<220> FEATURE:
<221> NAME/KEY: misc_feature
<222> LOCATION: (5)..(5)
<223> OTHER INFORMATION: Xaa can be any naturally occurring amino acid

<400> SEQUENCE: 31

Val Thr Phe Val Xaa Asn His Asp
1               5

<210> SEQ ID NO 32
<211> LENGTH: 6
<212> TYPE: PRT
<213> ORGANISM: Artificial Sequence
<220> FEATURE:
<223> OTHER INFORMATION: Primer

<400> SEQUENCE: 32

Gly Trp Thr Arg Glu Gly
1               5

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
ggcgttaacc gcagcttgta ac                                            22
```

-continued

<210> SEQ ID NO 34
<211> LENGTH: 51
<212> TYPE: DNA
<213> ORGANISM: Artificial Sequence
<220> FEATURE:
<223> OTHER INFORMATION: Primer

<400> SEQUENCE: 34
ccgagctcgg ccggctgggc cgtcgactta tttgtttacc caaatagaaa c    51

<210> SEQ ID NO 35
<211> LENGTH: 37
<212> TYPE: DNA
<213> ORGANISM: Artificial Sequence
<220> FEATURE:
<223> OTHER INFORMATION: Primer

<400> SEQUENCE: 35
cattctgcag cagcggcgca ccataatggt acgaacg    37

<210> SEQ ID NO 36
<211> LENGTH: 400
<212> TYPE: PRT
<213> ORGANISM: Artificial Sequence
<220> FEATURE:
<223> OTHER INFORMATION: Partial Alpha-Amylase

<400> SEQUENCE: 36

```
Asn Gly Thr Asn Gly Thr Met Met Gln Tyr Phe Glu Trp Tyr Leu Pro
1               5                   10                  15

Asn Asp Gly Asn His Trp Asn Arg Leu Arg Ser Asp Ala Ser Asn Leu
            20                  25                  30

Lys Asp Lys Gly Ile Ser Ala Val Trp Ile Pro Pro Ala Trp Lys Gly
        35                  40                  45

Ala Ser Gln Asn Asp Val Gly Tyr Gly Ala Tyr Asp Leu Tyr Asp Leu
    50                  55                  60

Gly Glu Phe Asn Gln Lys Gly Thr Ile Arg Thr Lys Tyr Gly Thr Arg
65                  70                  75                  80

Asn Gln Leu Gln Ala Ala Val Asn Ala Leu Lys Ser Asn Gly Ile Gln
                85                  90                  95

Val Tyr Gly Asp Val Val Met Asn His Lys Gly Gly Ala Asp Ala Thr
            100                 105                 110

Glu Met Val Arg Ala Val Glu Val Asn Pro Asn Asn Arg Asn Gln Glu
        115                 120                 125

Val Ser Gly Glu Tyr Thr Ile Glu Ala Trp Thr Lys Phe Asp Phe Pro
    130                 135                 140

Gly Arg Gly Asn Thr His Ser Asn Phe Lys Trp Arg Trp Tyr His Phe
145                 150                 155                 160

Asp Gly Val Asp Trp Asp Gln Ser Arg Lys Leu Asn Asn Arg Ile Tyr
                165                 170                 175

Lys Phe Arg Gly Asp Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Ser Ile His Val Arg Ser Ala Thr Gly
```

```
                        245                 250                 255
Lys Asn Met Phe Ala Val Ala Glu Phe Trp Lys Asn Asp Leu Gly Ala
            260                 265                 270

Ile Glu Asn Tyr Leu Asn Lys Thr Asn Trp Asn His Ser Val Phe Asp
            275                 280                 285

Val Pro Leu His Tyr Asn Phe Tyr Asn Ala Ser Lys Ser Gly Gly Asn
            290                 295                 300

Tyr Asp Met Arg Gln Ile Phe Asn Gly Thr Val Val Gln Arg His Pro
305                 310                 315                 320

Met His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
                340                 345                 350

Leu Thr Leu Thr Arg Glu Gln Gly Tyr Pro Ser Val Phe Tyr Gly Asp
            355                 360                 365

Tyr Tyr Gly Ile Pro Thr His Gly Val Pro Ala Met Lys Ser Lys Ile
            370                 375                 380

Asp Pro Ile Leu Glu Ala Arg Gln Lys Tyr Ala Tyr Gly Arg Gln Asn
385                 390                 395                 400

<210> SEQ ID NO 37
<211> LENGTH: 485
<212> TYPE: PRT
<213> ORGANISM: Bacillus sp.

<400> SEQUENCE: 37

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Gly Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Met Val Asn Ala Val Glu Val Asn Arg Ser Asn Arg Asn
        115                 120                 125

Gln Glu Ile Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Ile Glu Asn Gly Asn Tyr Asp Tyr Leu Met Tyr Ala Asp Ile Asp Met
        195                 200                 205

Asp His Pro Glu Val Ile Asn Glu Leu Arg Asn Trp Gly Val Trp Tyr
    210                 215                 220

Thr Asn Thr Leu Asn Leu Asp Gly Phe Arg Ile Asp Ala Val Lys His
```

```
                225                 230                 235                 240

Ile Lys Tyr Ser Tyr Thr Arg Asp Trp Leu Thr His Val Arg Asn Thr
                245                 250                 255

Thr Gly Lys Pro Met Phe Ala Val Ala Glu Phe Trp Lys Asn Asp Leu
                260                 265                 270

Ala Ala Ile Glu Asn Tyr Leu Asn Lys Thr Ser Trp Asn His Ser Val
                275                 280                 285

Phe Asp Val Pro Leu His Tyr Asn Leu Tyr Asn Ala Ser Asn Ser Gly
                290                 295                 300

Gly Tyr Phe Asp Met Arg Asn Ile Leu Asn Gly Ser Val Val Gln Lys
305                 310                 315                 320

His Pro Ile His Ala Val Thr Phe Val Asp Asn His Asp Ser Gln Pro
                325                 330                 335

Gly Glu Ala Leu Glu Ser Phe Val Gln Ser Trp Phe Lys Pro Leu Ala
                340                 345                 350

Tyr Ala Leu Ile Leu Thr Arg Glu Gln Gly Tyr Pro Ser Val Phe Tyr
                355                 360                 365

Gly Asp Tyr Tyr Gly Ile Pro Thr His Gly Val Pro Ser Met Lys Ser
    370                 375                 380

Lys Ile Asp Pro Leu Leu Gln Ala Arg Gln Thr Tyr Ala Tyr Gly Thr
385                 390                 395                 400

Gln His Asp Tyr Phe Asp His His Asp Ile Ile Gly Trp Thr Arg Glu
                405                 410                 415

Gly Asp Ser Ser His Pro Asn Ser Gly Leu Ala Thr Ile Met Ser Asp
                420                 425                 430

Gly Pro Gly Gly Asn Lys Trp Met Tyr Val Gly Lys His Lys Ala Gly
                435                 440                 445

Gln Val Trp Arg Asp Ile Thr Gly Asn Arg Ser Gly Thr Val Thr Ile
    450                 455                 460

Asn Ala Asp Gly Trp Gly Asn Phe Thr Val Asn Gly Gly Ala Val Ser
465                 470                 475                 480

Val Trp Val Lys Gln
                485
```